United States Patent
Boven et al.

(10) Patent No.: US 10,786,518 B2
(45) Date of Patent: Sep. 29, 2020

(54) COMPOSITIONS AND METHODS OF TREATING HIV

(71) Applicants: Janssen Sciences Ireland UC, Little Island, Co. Cork (IE); Gilead Sciences, Inc., Foster City, CA (US)

(72) Inventors: Katia Boven, Titusville, NJ (US); Goedele De Smedt, Geel (BE); Regina Driesen, Kessel (BE); Dominiek Henrist, Zoersel (BE); Greet Kauwenberghs, Schoten (BE); Sandeep Mathur, Furlong, PA (US); Scott McCallister, San Francisco, CA (US); Roel Mertens, Balen (BE); Richard Nettles, New Hope, PA (US); Magda Opsomer, Sint-Pieters-Leeuw (BE); William Pyrz, Belmont, CA (US); Vahid Zia, Palo Alto, CA (US)

(73) Assignees: Janssen Sciences Ireland UC, Co Cork (IE); Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/040,324

(22) Filed: Jul. 19, 2018

(65) Prior Publication Data
US 2019/0022113 A1 Jan. 24, 2019

Related U.S. Application Data

(60) Provisional application No. 62/665,339, filed on May 1, 2018, provisional application No. 62/623,174, filed
(Continued)

(51) Int. Cl.
*A61K 31/36* (2006.01)
*A61K 31/54* (2006.01)
(Continued)

(52) U.S. Cl.
CPC .......... *A61K 31/675* (2013.01); *A61K 9/2054* (2013.01); *A61K 31/513* (2013.01);
(Continued)

(58) Field of Classification Search
CPC .. A61K 9/2054; A61K 31/513; A61K 31/675; A61K 31/506; A61K 31/34; A61K 31/18; A61P 31/18
(Continued)

(56) References Cited

U.S. PATENT DOCUMENTS

2014/0037724 A1* 2/2014 Dahl .................... A61K 9/2054
424/464
2014/0142070 A1* 5/2014 Delaet .................. A61K 9/2054
514/158

FOREIGN PATENT DOCUMENTS

WO 2013/004816 A1 1/2013
WO 2013/004818 A1 1/2013
(Continued)

OTHER PUBLICATIONS

Birkus, et al., Activation of 9-[(R)-2-[[(S)-[[(S)-1-(Isopropoxycarbonyl)ethyl]amino] phenoxyphosphinyl]-methoxy] propyl]adenine (GS-7340) and Other Tenofovir Phosphonoamidate Prodrugs by Human Proteases, Molecular Pharmacology, 2008, pp. 92-100, vol. 74 Issue 1.
(Continued)

*Primary Examiner* — Shengjun Wang

(57) ABSTRACT

The disclosure is directed to methods of treating subjects infected with HIV, once daily, with single unit dosage forms that include darunavir (or a hydrate or solvate thereof), cobicistat, emtricitabine, and a tenofovir prodrug, or salt thereof.

25 Claims, 14 Drawing Sheets

Related U.S. Application Data on Jan. 29, 2018, provisional application No. 62/571,384, filed on Oct. 12, 2017, provisional application No. 62/534,885, filed on Jul. 20, 2017.

(51) Int. Cl.
| | |
|---|---|
| *A61K 31/505* | (2006.01) |
| *A61K 31/675* | (2006.01) |
| *A61K 9/36* | (2006.01) |
| *A61K 9/20* | (2006.01) |
| *A61K 31/7068* | (2006.01) |
| *A61K 31/683* | (2006.01) |
| *A61P 31/18* | (2006.01) |
| *A61K 31/513* | (2006.01) |
| *A61K 31/5377* | (2006.01) |
| *A61K 31/635* | (2006.01) |

(52) U.S. Cl.
CPC ........ *A61K 31/5377* (2013.01); *A61K 31/635* (2013.01); *A61K 31/683* (2013.01); *A61K 31/7068* (2013.01); *A61P 31/18* (2018.01)

(58) Field of Classification Search
USPC .................. 514/466, 236.8, 274, 86; 424/480
See application file for complete search history.

(56) References Cited

FOREIGN PATENT DOCUMENTS

| | | |
|---|---|---|
| WO | 2013/115916 A1 | 8/2013 |
| WO | WO2016/108205 A1 * | 7/2016 |

OTHER PUBLICATIONS

Birkus, et al., Cathepsin A Is the Major Hydrolase Catalyzing the Intracellular Hydrolysis of the Antiretroviral Nucleotide Phosphonoamidate Prodrugs GS-7340 and GS-9131, Antimicrobial Agents and Chemotherapy, 2007, pp. 543-530, vol. 51 Issue 2.
Blum, et al., Steady-State Pharmacokinetics of Emtricitabine and Tenofovir Disoproxil Fumarate Administered Alone and in Combination in Healthy Volunteers, Journal of Clinical Pharmacology, 2007, pp. 751-759, vol. 47.
Cahn, et al., Week 48 analysis of once-daily vs. twice-daily darunavir/ritonavir in treatment-experienced HIV-1-infected patients, AIDS, 2011, pp. 929-939, vol. 25 Issue 7.
Clay, et al., Meta-Analysis of Studies Comparing Single and Multi-Tablet Fixed Dose Combination HIV Treatment Regimens, Medicine, 2015, pp. 1-14, vol. 94 Issue 42.
ClinicalTrials.gov NCT02269917, Study to Evaluate Efficacy and Safety of Darunavir/Cobicistat/Emtricitabine/Tenofovir Alafenamide (D/C/F/TAF) Regimen Versus Boosted Protease Inhibitor (bPI) Along With Emtricitabine/Tenofovir Disoproxil Fumarate (FTC/TDF) Regimen in Virologically-Suppressed . . . , 2014, https://clinicaltrials.gov/ct2/show/NCT02269917?term=D%2FC%2FF%2FTAF&age=1&phase=2& draw=1 &rank=1.
ClinicalTrials.gov NCT02431247, A Study to Evaluate Efficacy and Safety of Darunavir/Cobicistat/Emtricitabine/Tenofovir Alafenamide (D/C/F/TAF) Fixed Dose Combination (FDC) Versus a Regimen Consisting of Darunavir/Cobicistat FDC With Emtricitabine/Tenofovir Disoproxil Fumarate FDC in . . . , 2015, https://clinicaltrials.gov/ct2/show/NCT02431247?term=D%2FC%2FF%2FTAF&age=1&phase=2& draw=1 &rank=2.
ClinicalTrials.gov NCT02475135, Relative Bioavailability and Food Effect for Darunavir/Cobicistat/Emtricitabine/Tenofovir Alafenamide Fixed Dose Combination, 2015, https://clinicaltrials.gov/ct2/show/NCT02475135?term=NCT02475135&rank=1.
ClinicalTrials.gov NCT02578550, A Bioequivalence Study of Darunavir, Emtricitabine, and Tenofovir Alafenamide, in the Presence of Cobicistat in Healthy Participants, 2015, https://clinicaltrials.gov/ct2/show/NCT02578550?term=NCT02578550&rank=1.
ClinicalTrials.gov NCT03227861, A Study to Evaluate the Efficacy and Safety of (D/C/F/TAF) Once Daily Fixed Dose Combination (FDC) Regimen in Newly Diagnosed, Antiretroviral Treatment-naive Human Immunodeficiency Virus Type 1 (HIV-1) InfectedParticipants Receiving Care in a Test and Treat Model of Care, 2017, https://clinicaltrials.gov/ct2/show/NCT03227861?term=NCT03227861&rank=1.
Cockcroft, et al., Prediction of Creatinine Clearance from Serum Creatinine, Nephron, 1976, pp. 31-41, vol. 16.
Crauwels, et al., Impact of food on the bioavailability of darunavir, cobicistat, emtricitabine and tenofovir alafenamide, the first protease inhibitor-based complete HIV-1 regimen (DCFTAF), J Acquir Immune Defic Syndr AIDS Patient Care STDS AIDS, 2016, Retrieved from the Internet: URL:http://programme.aids2016.org/PAGMaterial/eposters/0_3076.pdf.
Dejesus, et al., Simplification of Antiretroviral Therapy to a Single-Tablet Regimen Consisting of Efavirenz, Emtricitabine, and Tenofovir Disoproxil Fumarate Versus Unmodified Antiretroviral Therapy in Virologically Suppressed HIV-1-Infected Patients, J Acquir Immune Defic Syndr, Jun. 1, 2009, pp. 163-174, vol. 51 Issue 2.
Eron, et al., Week 48 results of AMBER: a phase 3, randomised, double-blind trial in antiretroviral treatment-naïve HIV-1-infected adults to evaluate the efficacy and safety of the once-daily, single-tablet regimen of darunavir/cobicistat/emtricitabine/tenofovir alafenamide (D/C/F/TAF) versus darunavir/cobicistat plus emtricitabine/tenofovir disoproxil fumarate, EACS, 2017, Abstract PS8/2.
Flynn, et al., Efficacy and Safety of Darunavir/Ritonavir at 48 Weeks in Treatment-naïve, HIV-1-infected Adolescents, The Pediatric Infectious Disease Journal, 2014, pp. 940-945, vol. 33 Issue 9.
Golkowski, et al., Blinded sample size re-estimation in crossover bioequivalence trials, Pharmaceutical Statistics, 2014, pp. 157-162, vol. 13.
Hodder, et al., Patient-Reported Outcomes in Virologicaily Suppressed, HIV-1-Infected Subjects After Switching to a Simplified, Single-Tablet Regimen of Efavirenz, Emtricitabine, and Tenofovir DF, AIDS Patient Care and STDs, 2010, pp. 87-96, vol. 24 Issue 2.
Huhn, et al., A Randomized, Open-Label Trial to Evaluate Switching to Elvitearavir/Cobicistat/Emtricitabine/Tenofovir Alafenamide Plus Darunavir in Treatment-Experienced HIV-1-infected Adults, Journal of Acquired Immune Deficiency Syndromes, Feb. 1, 2017, pp. 193-200, vol. 74 Issue 2.
International Search Report and Written Opinion dated Oct. 25, 2018, for International Application No. PCT/US2018/042937.
Johnson, et al., Update of the Drug Resistance Mutations in HIV-1: Dec. 2010, Topics in HIV Medicine, 2010, pp. 156-163, vol. 18, No. 5.
Kakuda, et al., Bioequivalence of a darunavir/cobicistat fixed-dose combination tablet versus single agents and food effect in healthy volunteers, Antiviral Therapy, 2014, pp. 597-606, vol. 19.
Lee, et al., Selective Intracellular Activation of a Novel Prodrug of the Human Immunodeficiency Virus Reverse Transcriptase Inhibitor Tenofovir Leads to Preferential Distribution and Accumulation in Lymphatic Tissue, Antimicrobial Agents and Chemotherapy, 2005, pp. 1898-1906, vol. 49 Issue 5.
Mills, et al., Once-daily darunavir/ritonavir vs. lopinavir/ritonavir in treatment-naive, HIV-1-infected patients: 96-week analysis, AIDS, 2009, pp. 1679-1688, vol. 23 Issue 13.
Mills, et al., Tenofovir Alafenamide Versus Tenofovir Disoproxil Fumarate in the First Protease Inhibitor-Based Single-Tablet Regimen for Initial HIV-1 Therapy: A Randomized Phase 2 Study, Journal of Acquired Immune Deficiency Syndromes, Aug. 1, 2015, pp. 439-445, vol. 69 Issue 4.
NIAID. Division of AIDS table for grading the severity of adult and pediatric adverse events—version 2. https://rsc.tech-res.com/docs/default-source/safety/daids_ae_grading_table_v2_nov2014.pdf?sfvrsn=8 (Nov. 2014; accessed Apr. 25, 2017).
Orkin, et al., Efficacy and safety of switching from boosted protease inhibitors plus emtricitabine and tenofovir disoproxil fumarate regimens to single-tablet darunavir, cobicistat, emtricitabine, and tenofovir alafenamide at 48 weeks in adults with virologically

(56) References Cited

OTHER PUBLICATIONS suppressed HIV-1 (EMERALD): a phase 3, randomised, non-inferiority trial, (and Supplementary Appendix) Lancet HIV, 2017, pp. 1-169.

Orkin, et al., Final 192-week efficacy and safety of once daily darunavir/ritonavir compared with lopinavir/ritonavir in HIV-1-infected treatment-naïve patients in the ARTEMIS trial*, HIV Medicine, 2013, pp. 49-59, vol. 14.

Ortiz, et al., Efficacy and safety of once-daily darunavir/ritonavir versus lopinavir/ritonavir in treatment-naive HIV-1-infected patients at week 48, AIDS, 2008, pp. 1389-1397, vol. 22 Issue 12.

Ruane, et al., Antiviral Activity, Safety, and Pharmacokinetics/Pharmacodynamics of Tenofovir Alafenamide as 10-Day Monotherapy in HIV-1-Positive Adults, J Acquir Immune Defic Syndr, Aug. 1, 2013, pp. 449-455, vol. 63 Issue 4.

Ruxrungtham, et al., Rationale and Clinical Utility of the darunavir-cobicistat combination in the treatment of HIV/AIDS, Drug Design Development and Therapy, 2015, pp. 5763-5769, vol. 9.

Sax, et al., Tenofovir Alafenamide Vs. Tenofovir Disoproxil Fumarate in Single Tablet Regimens for Initial HIV-1 Therapy: A Randomized Phase 2 Study, J Acquir Immune Defic Syndr, Sep. 1, 2014, pp. 52-58, vol. 67 Issue 1.

Sekar, et al., The Effect of Different Meal Types on the Pharmacokinetics of Darunavir (TMC114)/Ritonavir in HIV-Negative Healthy Volunteers; J Clin Pharmacol; 2007, pp. 479-484, vol. 47.

Tashima, et al., Cobicistat-boosted darunavir in HIV-1-infected adults: week 48 results of a Phase IIIb, open-label single-arm trial, AIDS Research and Therapy, 2014, pp. 1-12, vol. 11 Issue 39.

Willig, et al., Increased regimen durability in the era of once-daily fixed-dose combination antiretroviral therapy, AIDS, 2008, pp. 1951-1960, vol. 22.

Chastain, D., et al., Optimizing Antiretroviral Therapy in Treatment-Experienced Patients Living with HIV: A Critical Review of Switch and Simplification Strategies. An Opinion of the HIV Practice and Research Network of the American College of Clinical Pharmacy, Journal of the International Association of Providers of AIDS Care, 2019, vol. 18/1-22, DOI: 10.1177/2325958219867325.

Dimala, C.A., et al., Motives for change of first-line antiretroviral therapy regimens in an unselected cohort of HIV/AIDS patients at a major referral centre in South-west Cameroon, BMC Res Notes, 2017, 10:623; DOI 10.1186/s13104-017-2948-3.

Meloni, S.T., et al., Implication of First-Line Antiretroviral Therapy Choice on Second-Line Options, Open Forum Infectious Diseases, 2017, DOI: 10.1093/ofid/ofx233.

Mussini, C., et al., Switching to dual/monotherapy determines an increase in CD8+ in HIV-infected individuals: an observational cohort study, BMC Medicine, 2018, 16:79; https://doi.org/10.1186/s12916-018-1046-2.

Perrier, M., et al., Switch as maintenance to elvitegravir/cobicistat/emtricitabine/ tenofovir disoproxil fumarate: week 48 results in a clinical cohort, J Antimicrob Chemother, 2017, pp. 1745-1751, vol. 72.

Shearer, K., et al., Treatment outcomes of over 1000 patients on second-line, protease inhibitor-based antiretroviral therapy from four public-sector HIV treatment facilities across Johannesburg, South Africa, Tropical Medicine and International Health, 2017, pp. 221-231, vol. 22, No. 2.

* cited by examiner

D/C/F/TAF=darunavir/cobicistat/emtricitabine/tenofovir alafenamide; Control regimen=darunavir/cobicistat plus emtricitabine/tenofovir disoproxil fumarate once daily

COMPOSITIONS AND METHODS OF TREATING HIV

CROSS REFERENCE TO RELATED APPLICATIONS

This application claims the benefit of U.S. Provisional Application No. 62/534,885, filed Jul. 20, 2017, 62/571,384, filed Oct. 12, 2017, 62/623,174, filed Jan. 29, 2018, and 62/665,339, filed May 1, 2018, the entireties of which are incorporated by reference herein.

TECHNICAL FIELD

The disclosure is directed to methods of treating subjects infected with HIV, for example, HIV-1, once daily, with single unit dosage forms that include darunavir (or a hydrate or solvate thereof), cobicistat, emtricitabine, and a tenofovir prodrug, or salt thereof.

BACKGROUND

The treatment of Human Immunodeficiency Virus (HIV) infection, known as cause of the acquired immunodeficiency syndrome (AIDS), remains a major medical challenge. HIV is able to evade immunological pressure, to adapt to a variety of cell types and growth conditions and to develop resistance against currently available drug therapies. The latter include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs), fusion inhibitors, and the more recent integrase inhibitors.

Although effective in suppressing HIV, each of these drugs, when used alone, is confronted with the emergence of resistant mutants. This led to the introduction of combination therapy of three or more anti-HIV agents, each usually having a different activity profile. In particular the introduction of "HAART" (Highly Active Anti-Retroviral Therapy) resulted in a remarkable improvement in anti-HIV therapy, leading to a large reduction in HIV-associated morbidity and mortality. Current guidelines for anti-retroviral therapy recommend such triple combination therapy regimen even for initial treatment. However, none of the currently available drug therapies is capable of completely eradicating HIV. Even HAART may face the emergence of resistance, often due to non-adherence to anti-retroviral therapy. In these cases HAART can be made effective again by replacing one of its components by one of another class. If applied correctly, treatment with HAART combinations can suppress the virus for many years, up to decades, to a level where it no longer can cause transmission of HIV.

Because of their pharmacokinetic properties and the need to keep plasma levels above a minimum level, currently used anti-HIV drugs require frequent administration of relatively high doses. The number and/or volume of dosage forms that need to be administered are commonly referred to as the "pill burden". A high pill burden is undesirable for many reasons, such as the frequency of intake, often combined with the inconvenience of having to swallow large dosage forms, as well as the need to store and transport a large number or volume of pills. A high pill burden increases the risk of patients not taking their entire dose, thereby failing to comply with the prescribed dosage regimen. As well as reducing the effectiveness of the treatment, this also leads to the emergence of viral resistance. The problems associated with a high pill burden are multiplied where a patient must take a combination of different anti-HIV agents or agents in combination with a so called booster to improve pharmacokinetic properties.

Providing single unit dosage forms contributes to the convenience of intake and therefore also helps to overcome problems of pill burden. Therefore, it would be desirable to provide effective HIV inhibitory therapy that reduces pill burden.

SUMMARY

The disclosure is directed to, among other things, methods of treating a subject infected with HIV, in particular HIV-1, comprising orally administering to the subject, once daily, a single unit dosage form comprising
  darunavir, or a hydrate or solvate thereof;
  cobicistat;
  emtricitabine; and
  tenofovir alafenamide, or a pharmaceutically acceptable salt thereof;
wherein the subject is treatment experienced and was administered a first anti-retroviral regimen that has been discontinued; and wherein the subject exhibits a viral load of less than or equal to 50 copies, preferably less than 50 copies, of HIV-1 virus particles per mL of blood plasma, after at least 24 weeks of the once-daily administration of the single unit dosage form.

The disclosure is also directed to methods of treating a subject infected with HIV-1 comprising administering to the subject, once daily, a single unit dosage form of the disclosure; wherein the subject exhibits a viral load of less than or equal to 50 copies, preferably less than 50 copies; of HIV-1 virus particles per mL of blood plasma, after at least 24 weeks of once daily administration of the fixed dose, single unit dosage form.

Single unit dosage forms are also described, as well as methods of manufacturing them.

DETAILED DESCRIPTION OF ILLUSTRATIVE EMBODIMENTS

Figure 1A:
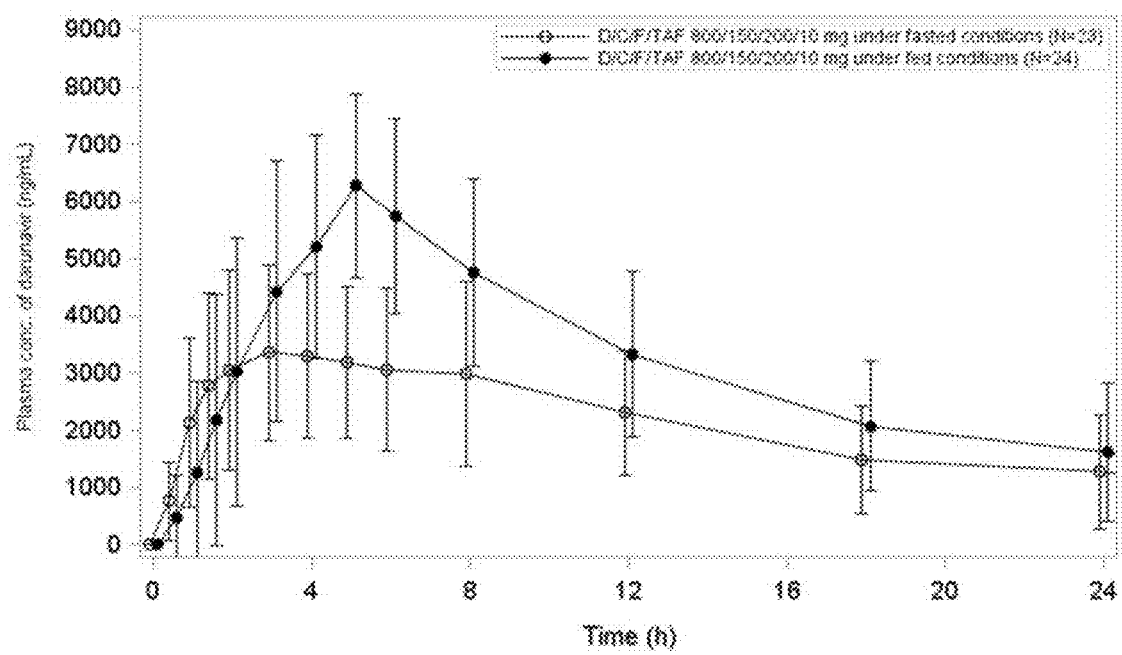
FIG. 1A. Food-effect bioavailability study: Mean (standard deviation) plasma concentration-time profiles for darunavir (D or DRV) following administration of a single oral dose of D/C/F/TAF (darunavir/cobicistat/emtricitabine/tenofovir alafenamide) 800/150/200/10 mg under fed (standardized high-fat breakfast) and fasted conditions.

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically carriers, and excludes other compounds.

All ranges disclosed herein are inclusive of the recited endpoint and independently combinable (for example, the range of "from 2 mg to 10 mg" is inclusive of the endpoints, 2 mg and 10 mg, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the disclosure that is pharmaceutically acceptable and that possesses the desired pharmacological activity of the parent compound. In particular, such salts are nontoxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4- hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. See, e.g., U.S. Food & Drug Administration, Pharmaceutical Quality/CMC Guidances.

"Pharmaceutically acceptable excipient" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, stearates, silicon dioxide, polyvinyl alcohols, talc, titanium dioxide, ferric oxide, and polyethylene glycols. See, e.g., U.S. Food & Drug Administration, Pharmaceutical Quality/CMC Guidances.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

The disclosure is directed to methods of treating a subject infected with an HIV. The methods described herein are particularly effective in treating subjects infected with HIV-1. Preferably, subjects treated according to the methods described herein do not harbor any darunavir resistance-associated mutations in HIV-1 protease. In other aspects, subjects treated according to the methods described herein harbor a darunavir resistance-associated mutation in HIV-1 protease. Also preferred is that the subjects treated according to the methods described herein do not have a K65R mutation in HIV-1 reverse transcriptase. In other aspects, subjects treated according to the methods of the disclosure will not have full sensitivity to all of the components of the described single unit dosage forms. In other aspects, subjects treated according to the methods described herein do not harbor an M184V HIV mutation. Methods of detecting HIV, HIV-1, and HIV-1 mutations can be performed using methods known in the art, for example, using HIV antibody tests, HIV antigen tests, and HIV nucleic acid amplification tests.

In some aspects, the disclosure is directed to methods of treating a subject with an anti-retroviral regimen in order to reduce the subject's pill burden. For example, some prior anti-retroviral dosage regimens, while effective in maintaining an acceptable HIV-1 viral load, may comprise more than one dosage form and/or more than one dose per day, resulting in an undesirable pill burden for the subject. In other aspects, the subject's prior anti-retroviral dosage regimen may not be effective in maintaining an acceptable HIV-1 viral load. Alternatively, the subject's prior anti-retroviral dosage regimen may not be effective in maintaining an acceptable HIV-1 viral load and presents an undesirable pill burden for the subject.

In some aspects of the disclosure, a single unit dosage form as described herein may be administered to a subject infected with HIV, for example, infected with HIV-1, wherein the subject may have been previously administered an anti-retroviral regimen, but to whom such prior regimen has been discontinued. Such subjects may be referred to as "treatment experienced" or "non-treatment-naïve." In these subjects, the prior anti-retroviral regimen, also referred to herein as a "first anti-retroviral regimen," may have been discontinued for about 12 or 24 hours. In other aspects, the prior anti-retroviral regimen may have been discontinued for about 2, 3, 4, 5, or 6 days. In other aspects, the prior anti-retroviral regimen may have been discontinued for about 1, 2, 3, 4, 5, 6, 7, or 8 weeks or longer. In some aspects, the prior anti-retroviral regimen may have been discontinued for about 3, 4, 5, 6, 7, 8, 9, 10, or about 11 months. In other aspects, the prior anti-retroviral regimen may have been discontinued for about 1, 2, 3, 4, 5, 6, 7, 8, 9, or about 10 years.

In these methods, preferably within about 48 hours or less after the first anti-retroviral regimen is discontinued, the subject is orally administered, on a once daily schedule, a single unit dosage form as disclosed herein. Some aspects may require that the single unit dosage form is orally administered, on a once daily schedule, more than 48 hours after the first anti-retroviral regimen is discontinued, if the first anti-retroviral regimen was associated with certain adverse events such as rash, increase in SCr, resistant mutations, and the like. In other aspects, the subject is orally administered, on a once daily schedule, a single unit dosage form of the disclosure within about 36 hours or less after the first anti-retroviral regimen is discontinued. In other aspects, the subject is orally administered, on a once daily schedule, a single unit dosage form of the disclosure within about 24 hours or less after the first anti-retroviral regimen is discontinued. In preferred embodiments, the single unit dosage forms of the disclosure are administered with food.

The single unit dosage forms of the disclosure comprise:
darunavir, or a hydrate or solvate thereof;
cobicistat;
emtricitabine; and
tenofovir, a tenofovir prodrug, a pharmaceutically acceptable salt of tenofovir, or a pharmaceutically acceptable salt of a tenofovir prodrug.

"Single unit dosage forms" of the disclosure are suitable for oral administration to a patient. Examples of dosage forms include, but are not limited to, tablets; caplets; and capsules, such as soft elastic gelatin capsules. Single unit dosage forms of the disclosure are preferable tablets.

According to the disclosure, the single unit dosage forms comprise darunavir, a darunavir hydrate, a darunavir solvate; or a combination thereof. In some aspects of the disclosure, the single unit dosage forms include darunavir.

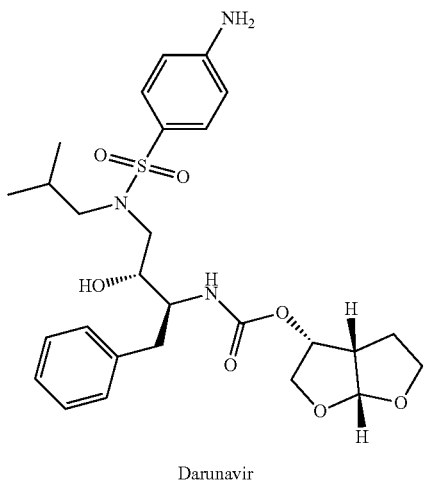 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

Darunavir

In other aspects of the disclosure, the single unit dosage forms include darunavir hydrate, for example, darunavir monohydrate, darunavir hemihydrate, or darunavir dehydrate. In yet other aspects of the disclosure, the single unit dosage forms include a darunavir solvate. Preferred darunavir solvates include darunavir ethanolate, darunavir propanolate, and darunavir isopropanolate. A particularly preferred darunavir solvate is darunavir ethanolate.

In preferred aspects, the single unit dosage forms include about 400 to about 1200 mg of darunavir. For example, the single unit dosage forms include about 400, 500, 600, 700, 800, 900, 1000, 1100, or about 1200 mg of darunavir. In particularly preferred aspects, the single unit dosage forms include about 800 mg of darunavir. The amounts of darunavir described herein are based on the free form of darunavir, that is, the non-hydrated, non-solvated form of darunavir. If a hydrate or a solvate is to be administered, the amounts need to be calculated as a function of the molecular weight ratio between the hydrate and the free form or the solvate and the free form. For example, 867 mg of darunavir ethanolate is equivalent to 800 mg of darunavir.

Also according to the disclosure, the single unit dosage forms comprise tenofovir, a tenofovir prodrug, a pharmaceutically acceptable salt of tenofovir, a pharmaceutically acceptable salt of a tenofovir prodrug, or a combination thereof. In some aspects of the disclosure, the single unit dosage forms includes tenofovir.

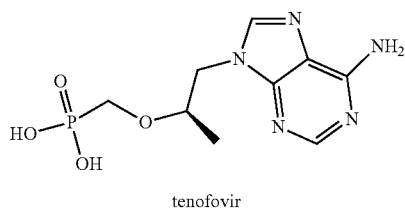 [SMILES: C[C@H](Cn1cnc2c(N)ncnc21)OCP(=O)(O)O]

tenofovir

In other aspects of the disclosure, the single unit dosage forms include a tenofovir prodrug, for example tenofovir disoproxil or tenofovir alafenamide.

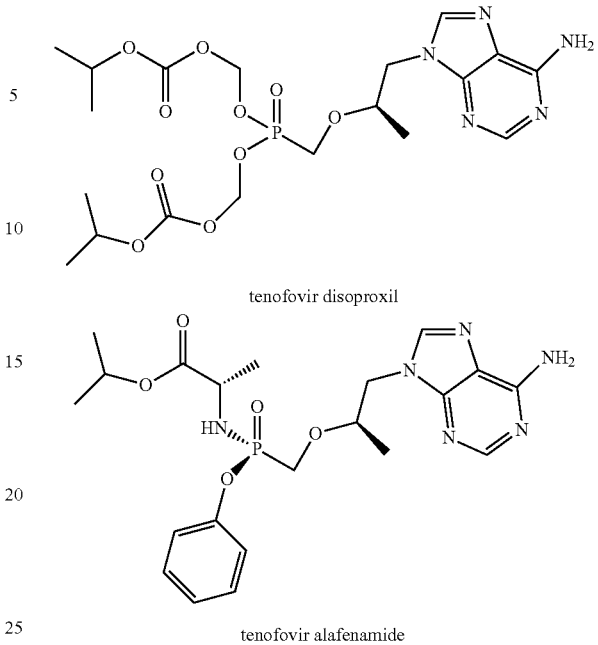

tenofovir disoproxil tenofovir alafenamide

A particularly preferred tenofovir prodrug is tenofovir alafenamide. In other aspects of the disclosure, the single unit dosage forms include a pharmaceutically acceptable salt of tenofovir. In other aspects of the disclosure, the single unit dosage forms include a pharmaceutically acceptable salt of a tenofovir prodrug. For example, in some aspects, the single unit dosage forms include a pharmaceutically acceptable salt of tenofovir disoproxil. Preferred pharmaceutically acceptable salts of tenofovir disoproxil include tenofovir disoproxil fumarate. In other aspects, the single unit dosage forms include a pharmaceutically acceptable salt of tenofovir alafenamide. Particularly preferred pharmaceutically acceptable salts of tenofovir alafenamide include tenofovir alafenamide fumarate and tenofovir alafenamide hemifumarate.

In preferred aspects, the single unit dosage forms include about 5 to about 15 mg of tenofovir alafenamide. For example, the single unit dosage forms can include about 5, 6, 8, 9, 10, 11, 12, 13, 14, or about 15 mg of tenofovir alafenamide. Particularly preferred are those single unit dosage forms that include about 10 mg of tenofovir alafenamide. The amounts of tenofovir alafenamide described herein are based on the free form of tenofovir alafenamide, that is, the non-salt form. If salts are administered, the amounts need to be calculated as a function of the molecular weight ratio between the salt and the free form. For example, 11.2 mg of tenofovir alafenamide hemifumarate is equivalent to 10 mg of tenofovir alafenamide.

In other aspects, the single unit dosage forms include about 200 to about 300 mg of tenofovir disoproxil. For example, the single unit dosage forms can include about 200, 210, 220, 230, 240, 250, 260, 270, 280, 290, or about 300 mg of tenofovir disoproxil. Also preferred are those single unit dosage forms that include about 245 mg of tenofovir disoproxil. The amounts of tenofovir disoproxil described herein are based on the free form of tenofovir disoproxil, that is, the non-salt form. If salts are administered, the amounts need to be calculated as a function of the molecular weight ratio between the salt and the free form.

In addition to including the darunavir, darunavir hydrate, and/or darunavir solvate and the tenofovir, tenofovir prodrug, tenofovir salt, and/or tenofovir prodrug salt, the single unit dosage forms of the disclosure include cobicistat and emtricitabine:

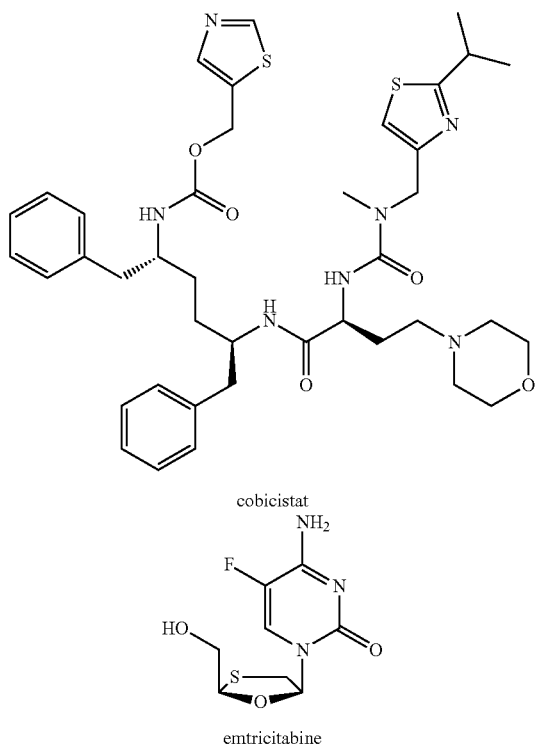

cobicistat emtricitabine

In preferred aspects, the cobicistat is provided as cobicistat on a silicon dioxide carrier. In some embodiments, the cobicistat on silicon dioxide is about 47% to about 56% cobicistat, preferably about 52% cobicistat, and about 44% to about 53% silicon dioxide, preferably, about 48% silicon dioxide. The cobicistat is preferably in amorphous form.

In preferred aspects, the single unit dosage forms include about 100 to about 200 mg of cobicistat. For example, the single unit dosage forms can include about 100, 110, 120, 130, 140, 150, 160, 170, 180, 190, or about 200 mg of cobicistat. Particularly preferred are those single unit dosage forms that include about 150 mg of cobicistat. In those embodiments wherein the cobicistat is provided on a silicon dioxide carrier, the amount of cobicistat is based on the free amount of cobicistat. For example, 288.5 mg of a 52 wt. % cobicistat on silicon dioxide is equivalent to 150 mg of cobicistat.

In preferred aspects, the single unit dosage forms include about 100 to about 300 mg of emtricitabine. For example, the single unit dosage forms can include about 100, 135, 150, 175, 200, 225, 250, 275, or about 300 mg of emtricitabine. Particularly preferred are those single unit dosage forms that include about 200 mg of emtricitabine.

Preferred single unit dosage forms of the disclosure comprise
  darunavir ethanolate;
  cobicistat;
  emtricitabine; and
  tenofovir alafenamide, tenofovir alafenamide fumarate, or tenofovir alafenamide hemifumarate.

Other preferred single unit dosage forms of the disclosure comprise
  darunavir ethanolate;
  cobicistat;
  emtricitabine; and
  tenofovir alafenamide.
Other single unit dosage forms of the disclosure comprise
  darunavir ethanolate;
  cobicistat;
  emtricitabine; and
  tenofovir disoproxil or tenofovir disoproxil fumarate.
Especially preferred single unit dosage forms of the disclosure comprise
  darunavir ethanolate, in an amount equivalent to about 800 mg of darunavir;
  cobicistat, in an amount equivalent to about 150 mg of cobicistat;
  emtricitabine, in an amount equivalent to about 200 mg emtricitabine; and
  tenofovir alafenamide fumarate, in an amount equivalent to about 10 mg of tenofovir alafenamide.

In some aspects, a subject not infected with HIV (for example, HIV-1) is orally administered, once daily, a single unit dosage form comprising
  darunavir, or a hydrate or solvate thereof;
  cobicistat;
  emtricitabine; and
  tenofovir alafenamide, or a pharmaceutically acceptable salt thereof, preferably tenofovir alafenamide fumarate or tenofovir alafenamide hemifumarate
prior to the subject's exposure to HIV, in particular, HIV-1. In these embodiments, the single unit dosage form is prophylactic to the subject becoming infected with HIV, in particular, HIV-1.

In most preferred methods of the disclosure, a subject infected with HIV, in particular, HIV-1, is orally administered, once daily, a single unit dosage form comprising
  darunavir, or a hydrate or solvate thereof;
  cobicistat;
  emtricitabine; and
  tenofovir alafenamide, or a pharmaceutically acceptable salt thereof, preferably, tenofovir alafenamide fumarate or tenofovir alafenamide hemifumarate.

In these most preferred methods, the subject is treatment experienced and was administered a first anti-retroviral regimen (i.e., a prior anti-retroviral regimen) that has been discontinued. In addition; the subject will have exhibited a viral load of less than or equal to 50 copies of HIV-1 virus particles per mL of blood plasma (≤50 c/mL) after at least 24 weeks of the once-daily administration of the single unit dosage form. In some aspects, the subject will have exhibited a viral load of less than 50 copies of HIV-1 virus particles per mL of blood plasma (<50 c/mL) after at least 24 weeks of the once-daily administration of the single unit dosage form. In these most preferred methods, the single unit dosage form comprises:
  darunavir ethanolate, in an amount equivalent to about 800 mg of darunavir;
  cobicistat, in an amount equivalent to about 150 mg of cobicistat;
  emtricitabine, in an amount equivalent to about 200 mg emtricitabine; and
  tenofovir alafenamide fumarate, in an amount equivalent to about 10 mg of tenofovir alafenamide.

In other preferred methods; the subject is treatment naïve and has an HIV viral load level (e.g., HIV-1 viral load level) of at least 1000 copies/mL. In other aspects, the subject is treatment naïve and has an HIV viral load level (e.g., HIV-1 viral load level) that is above baseline, but that is less than 1000 copies/mL. In these most preferred methods, the single unit dosage form comprises:

darunavir ethanolate, in an amount equivalent to about 800 mg of darunavir;

cobicistat, in an amount equivalent to about 150 mg of cobicistat;

emtricitabine, in an amount equivalent to about 200 mg emtricitabine; and tenofovir alafenamide fumarate, in an amount equivalent to about 10 mg of tenofovir alafenamide.

According to the disclosure, the subject may be treatment experienced, having been previously administered a first anti-retroviral regimen (i.e., a prior anti-retroviral regimen). The first anti-retroviral regimen can comprise any anti-retroviral regimen approved for use in subjects for investigational use or approved for marketing by a government agency. In some aspects, the first anti-retroviral regimen is administered to the subject for at least 6 consecutive months prior to the discontinuation and administration of a single unit dosage form of the disclosure.

In some aspects, the first anti-retroviral regimen comprises a boosted protease inhibitor;

emtricitabine; and tenofovir, a tenofovir prodrug, a pharmaceutically acceptable salt of tenofovir, or a pharmaceutically acceptable salt of a tenofovir prodrug As used herein, a "boosted protease inhibitor" is a "booster" and a protease inhibitor. "Boosters" are therapeutic agents that increase the plasma levels of, for example, protease inhibitors in the subject. For example, the booster may inhibit liver enzymes, inhibit certain intestinal transport proteins, and/or increase absorption of the protease inhibitor (mechanistic effect). In some aspects, the booster may also have some antiviral activity as a protease inhibitor, in addition to its mechanistic effect, for example, ritonavir. In other aspects, the effect of the booster is mechanistic as a cytochrome P450 3A inhibitor. A particularly preferred cytochrome P450 3A inhibitor is cobicistat.

The protease inhibitor of the boosted protease inhibitor of the first anti-retroviral regimen may be any protease inhibitor approved for use in subjects by a government agency. Preferred protease inhibitors include darunavir, darunavir hydrates, darunavir solvates, atazanavir, pharmaceutically acceptable salts of atazanavir, and lopinavir. Other protease inhibitors that may be part of a first anti-retroviral regimen include amprenavir, fosamprenavir, indinavir, nelfinavir, saquinavir, and tipranavir.

In preferred aspects, the protease inhibitor of the first anti-retroviral regimen is darunavir. Preferably, the boosted protease inhibitor is darunavir with ritonavir. Alternatively, the boosted protease inhibitor is darunavir with cobicistat. In other aspects, the protease inhibitor of the first anti-retroviral regimen is a darunavir hydrate. Preferably, the boosted protease inhibitor is a darunavir hydrate with ritonavir. Also preferred are those aspects wherein the boosted protease inhibitor is a darunavir hydrate with cobicistat. In other aspects, the protease inhibitor of the first anti-retroviral regimen is a darunavir solvate, for example darunavir ethanolate or darunavir propanolate. Preferably, the boosted protease inhibitor is a darunavir solvate with ritonavir. In other aspects, the boosted protease inhibitor is a darunavir solvate with cobicistat. In more preferred aspects, the boosted protease inhibitor is darunavir ethanolate with ritonavir. In other preferred aspects, the boosted protease inhibitor is darunavir ethanolate with cobicistat.

In other preferred aspects, the protease inhibitor of the first anti-retroviral regimen is atazanavir. Preferably, the boosted protease inhibitor is atazanavir with ritonavir. Alternatively, the boosted protease inhibitor is atazanavir with cobicistat. In other aspects, the protease inhibitor of the first anti-retroviral regimen is a pharmaceutically acceptable salt of atazanavir, for example, atazanavir sulfate. In some aspects, the boosted protease inhibitor is a pharmaceutically acceptable salt of atazanavir with cobicistat, for example, atazanavir sulfate with cobicistat.

In other preferred aspects, the protease inhibitor is lopinavir. Preferably, the boosted protease inhibitor is lopinavir with ritonavir.

According to the disclosure, the first anti-retroviral regimen comprises tenofovir, a tenofovir prodrug, a pharmaceutically acceptable salt of tenofovir, a pharmaceutically acceptable salt of a tenofovir prodrug, or a combination thereof. In some aspects of the disclosure, the first anti-retroviral regimen includes tenofovir. In other aspects of the disclosure, the first anti-retroviral regimen includes a tenofovir prodrug, for example tenofovir disoproxil or tenofovir alafenamide. A particularly preferred tenofovir prodrug of the first anti-retroviral regimen is tenofovir disoproxil. In other aspects of the disclosure, the first anti-retroviral regimen includes a pharmaceutically acceptable salt of tenofovir. In other aspects of the disclosure, the first anti-retroviral regimen includes a pharmaceutically acceptable salt of a tenofovir prodrug. For example, in some aspects, the first anti-retroviral regimen includes a pharmaceutically acceptable salt of tenofovir disoproxil. Preferred pharmaceutically acceptable salts of tenofovir disoproxil include tenofovir disoproxil fumarate.

In some aspects, the first anti-retroviral regimen is effective in treating the subject's HIV infection (e.g., is effective in treating the subject's HIV-1 infection). For example, in preferred aspects, a treatment experienced subject, during administration of the first anti-retroviral regimen, exhibits a viral load of less than or equal to 50 copies of HIV-1 virus particles per mL of blood plasma (≤50 c/mL). In some aspects, a treatment experienced subject, during administration of the first anti-retroviral regimen, exhibits a viral load of less than 50 copies of HIV-1 virus particles per mL of blood plasma (<50 c/mL). In some aspects, a subject, during administration of the first anti-retroviral regimen, exhibits a viral load of less than or equal to 25 copies of HIV-1 virus particles per mL of blood plasma (≤25 c/mL). In some aspects, a treatment experienced subject, during administration of the first anti-retroviral regimen, exhibits a viral load of less than 25 copies of HIV-1 virus particles per mL of blood plasma (<25 c/mL). In some aspects, a subject, during administration of the first anti-retroviral regimen, exhibits a viral load of less than or equal to 20 copies of HIV-1 virus particles per mL of blood plasma (≤20 c/mL). In some aspects, a treatment experienced subject, during administration of the first anti-retroviral regimen, exhibits a viral load of less than 20 copies of HIV-1 virus particles per mL of blood plasma (<20 c/mL). In preferred aspects, a subject, during administration of the first anti-retroviral regimen, exhibits a viral load of less than or equal to 50 copies of HIV-1 virus particles per mL of blood plasma (≤50 c/mL) (or less than 50 copies of HIV-1 virus particles per mL of blood plasma (<50 c/mL) at least 2 months, for example, between about 2 and 12 months, prior to discontinuation of the first anti-retroviral regimen. In preferred aspects, a subject, during administration of the first anti-retroviral regimen, exhibits a viral load of less than or equal to 25 copies of HIV-1 virus particles per mL of blood plasma (≤25 c/mL) (or less than 250 copies of HIV-1 virus particles per mL of blood plasma (<25 c/mL) at least 2 months, for example, between about 2 and 12 months, prior to discontinuation of the first anti-retroviral regimen. In preferred aspects, a subject, during administration of the first anti-retroviral regimen, exhibits a viral load of less than or equal to 20 copies of HIV-1 virus particles per mL of blood plasma (≤20 c/mL) (or less than 20 copies of HIV-1 virus particles per mL of blood plasma (<20 c/mL) at least 2 months, for example, between about 2 and 12 months, prior to discontinuation of the first anti-retroviral regimen.

In other aspects, the first anti-retroviral regiment is not effective in treating the treatment experienced subject's HIV infection (e.g., is not effective in treating the subject's HIV-1 infection). For example, a subject, during administration of the first anti-retroviral regimen, may exhibit a viral load of 100,000 or more copies of HIV-1 virus particles per mL of blood plasma (≥100,000 c/mL). In some aspects, a subject, during administration of the first anti-retroviral regimen, exhibits a viral load of 10,000 or more copies of HIV-1 virus particles per mL of blood plasma (≥10,000 c/mL). In sonic aspects, a subject, during administration of the first anti-retroviral regimen, exhibits a viral load of 1,000 or more copies of HIV-1 virus particles per mL of blood plasma (≥1,000 c/mL). In other aspects, a subject, during administration of the first anti-retroviral regimen, exhibits a viral load of 100 or more copies of HIV-1 virus particles per mL of blood plasma (≥100 c/mL). In other aspects, a subject, during administration of the first anti-retroviral regimen, exhibits a viral load of 50 or more copies of HIV-1 virus particles per mL of blood plasma (≥50 c/mL).

According to the disclosed methods, after at least 24 weeks of the once-daily administration of the single unit dosage form, after discontinuation of the first anti-retroviral regimen, the treatment experienced subject will exhibit a viral load of less than or equal to 50 copies of HIV-1 virus particles per mL of blood plasma (≤50 c/mL), or less than 50 copies of HIV-1 virus particles per mL of blood plasma (<50 c/mL). In other preferred aspects, after at least 48 weeks of once daily administration of the single unit dosage form, after discontinuation of the first anti-retroviral regimen, the subject will exhibit a viral load of less than or equal to 50 copies of HIV-1 virus particles per mL of blood plasma (≤50 c/mL), or less than 50 copies of HIV-1 virus particles per mL of blood plasma (<50 c/mL). In other preferred aspects, after at least 96 weeks of once daily administration of the single unit dosage form, after discontinuation of the first anti-retroviral regimen, the subject will exhibit a viral load of less than or equal to 50 copies of HIV-1 virus particles per mL of blood plasma (≤50 c/mL), or less than 50 copies of HIV-1 virus particles per mL of blood plasma (<50 c/mL). In other preferred aspects, after 24, 25, 26, 27, 28, 2.9, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 weeks of once daily administration of the single unit dosage form, after discontinuation of the first anti-retroviral regimen, the subject will exhibit a viral load of less than or equal to 50 copies of HIV-1 virus particles per mL of blood plasma (≤50 c/mL), or less than 50 copies of HIV-1 virus particles per mL of blood plasma (<50 c/mL). In some aspects, after more than 96 weeks of once daily administration of the single unit dosage form, after discontinuation of the first anti-retroviral regimen, the subject will exhibit a viral load of less than or equal to 50 copies of HIV-1 virus particles per mL of blood plasma (≤50 c/mL), or less than 50 copies of HIV-1 virus particles per mL of blood plasma (<50 c/mL).

Also in these aspects, after at least 24 weeks of once daily administration of the single unit dosage form after discontinuation of the first anti-retroviral regimen, the treatment experienced subject will exhibit the same cluster of differentiation (CD) 4+ cell count, as compared to the subject's CD4+ count prior to the administration. CD4+ cell count is a measure of immunologic status and can be measured using methods known in the art. In other aspects, after at least 24 weeks of once daily administration of the single unit dosage form, the subject will exhibit an improved cluster of differentiation (CD) 4+ cell count, as compared to the subject's CD4+ count prior to the administration. In other of these aspects, after at least 48 weeks of once daily administration of the single unit dosage form, the subject will exhibit the same cluster of differentiation (CD) 4+ cell count, as compared to the subject's CD4+ count prior to the administration. In other aspects, after at least 48 weeks of once daily administration of the single unit dosage form, the subject will exhibit an improved cluster of differentiation (CD) 4+ cell count, as compared to the subject's CD4+ count prior to the administration. In other aspects, after at least 96 weeks of once daily administration of the single unit dosage form, the subject will exhibit the same cluster of differentiation (CD) 4+ cell count, as compared to the subject's CD4+ count prior to the administration. In other aspects, after at least 96 weeks of once daily administration of the single unit dosage form, the subject will exhibit an improved cluster of differentiation (CD) 4+ cell count, as compared to the subject's CD4+ count prior to the administration.

In other aspects, after at least 24 weeks of once daily administration of the single unit dosage form after discontinuation of the first anti-retroviral regimen, the treatment experienced subject does not exhibit an emergent resistance-associated mutation in an HIV virus. In other aspects, after at least 48 weeks of once daily administration of the single unit dosage form, the subject does not exhibit an emergent resistance-associated mutation in an HIV virus. In other aspects, after at least 96 weeks of once daily administration of the single unit dosage form, the subject does not exhibit an emergent resistance-associated mutation in an HIV virus.

In other aspects, after at least 24 weeks of once daily administration of the single unit dosage form after discontinuation of the first anti-retroviral regimen, the treatment experienced subject exhibits the same lipid profile, as compared to the subject's lipid profile prior to the administration. As used herein, "lipid profile" refers to total cholesterol/HDL-cholesterol ratio. In other aspects, after at least 24 weeks of once daily administration of the single unit dosage form, the subject exhibits an improved lipid profile, as compared to the subject's lipid profile prior to the administration. In other aspects, after at least 48 weeks of once daily administration of the single unit dosage form, the subject exhibits the same lipid profile, as compared to the subject's lipid profile prior to the administration. In other aspects, after at least 48 weeks of once daily, administration of the single unit dosage form, the subject exhibits an improved lipid profile, as compared to the subject's lipid profile prior to the administration. In other aspects, after at least 96 weeks of once daily administration of the single unit dosage form, the subject exhibits the same lipid profile, as compared to the subject's lipid profile prior to the administration. In other aspects, after at least 96 weeks of once daily administration of the single unit dosage form, the subject exhibits an improved lipid profile, as compared to the subject's lipid profile prior to the administration.

In other aspects, after at least 24 weeks of once daily administration of the single unit dosage form after discontinuation of the first anti-retroviral regimen, the treatment experienced subject exhibits the same renal function, as compared to the subject's renal function prior to the administration. As used herein, "renal function" can be evaluated by any measure known in the art. For example, renal function can be evaluated based on estimated glomerular filtration rate (eGFR, by Cockcroft-Gault and by Chronic Kidney Disease Epidemiology Collaboration (CKD-EPI) methods and eGFRcystC (by CKD-EPI method)). Other renal measures include urine protein: creatinine ration, urine albumin:creatinine ratio, urine retinol binding protein:creatinine ratio, and urine beta-2-microglobulin:creatinine ratio. In other aspects, after at least 24 weeks of once daily administration of the single unit dosage form, the subject exhibits improved renal function, as compared to the subject's renal function prior to the administration. In other aspects, after at least 48 weeks of once daily administration of the single unit dosage form, the subject exhibits the same renal function, as compared to the subject's renal function prior to the administration. In other aspects, after at least 48 weeks of once daily administration of the single unit dosage form, the subject exhibits improved renal function, as compared to the subject's renal function prior to the administration. In other aspects, after at least 96 weeks of once daily administration of the single unit dosage form, the subject exhibits the same renal function, as compared to the subject's renal function prior to the administration. In other aspects, after at least 96 weeks of once daily administration of the single unit dosage form, the subject exhibits improved renal function, as compared to the subject's renal function prior to the administration.

In other aspects, after at least 24 weeks of once daily administration of the single unit dosage form after discontinuation of the first anti-retroviral regimen, the treatment experienced subject exhibits the same bone density, as compared to the subject's bone density prior to the administration. As used herein, "bone density," also referred to as "bone mineral density," can be measured at the lumbar spine or hip (total hip, i.e., femoral neck, trochanter, and intertrochanter areas) using methods known in the art, for example, using dual energy X-ray absorptiometry (DXA). In other aspects, after at least 24 weeks of once daily administration of the single unit dosage form, the subject exhibits improved bone density, as compared to the subject's bone density prior to the administration. In other aspects, after at least 48 weeks of once daily administration of the single unit dosage form, the subject exhibits the same bone density, as compared to the subject's bone density prior to the administration. In other aspects, after at least 48 weeks of once daily administration of the single unit dosage form, the subject exhibits improved bone density, as compared to the subject's bone density prior to the administration. In other aspects, after at least 96 weeks of once daily administration of the single unit dosage form, the subject exhibits the same bone density, as compared to the subject's bone density prior to the administration. In other aspects, after at least 96 weeks of once daily administration of the single unit dosage form, the subject exhibits improved bone density, as compared to the subject's bone density prior to the administration.

In some aspects of the disclosure, a single unit dosage form as described herein may be administered to a treatment-naïve subject infected with HIV, for example, infected with HIV-1. As used herein, a "treatment-naïve subject" has not been administered any prior anti-retroviral treatment to reduce HIV viral load and has not been administered any prior anti-retroviral treatment for post-exposure prophylaxis or pre-exposure prophylaxis. In some aspects, a treatment naïve subject will have been administered a prior anti-HIV drug for pre-exposure prophylaxis.

In some aspects, a treatment-naïve subject's viral load will not be precisely known. In other aspects, treatment-naïve subjects may exhibit a viral load of greater than or equal to 1000 copies of HIV virus particles (e.g., HIV-1 virus particles) per mL of blood plasma ($\geq$1000 c/mL) prior to the administration of the single unit dosage form. For example, treatment-naïve subjects may exhibit a viral load of greater than or equal to 100,000 copies of HIV-1 virus particles per mL of blood plasma ($\geq$100,000 c/mL) prior to the administration of the single unit dosage form.

In some aspects, the treatment naïve subjects' baseline HIV genotypes, e.g., HIV-1 genotypes, are analysed for protease mutations (including International Antiviral Society [IAS]-USA primary protease inhibitor resistance-associated mutations) and reverse transcriptase mutations (including IAS-USA NRTI resistance-associated mutations and IAS-USA NNRTI resistance-associated mutations). The treatment naïve subjects' genotypes can also be analysed for as specific mutations associated with resistance to the study drugs. Antiretroviral sensitivity, based on the genotype/phenotype report, can be assessed, according to some embodiments of the disclosure.

In some aspects, a treatment-naïve subject infected with HIV, in particular HIV-1, is administered a single unit dosage form as described herein. According to these methods, after at least 24 weeks of the once-daily administration of the single unit dosage form, the treatment-naïve subject will exhibit a viral load of less than or equal to 50 copies of HIV-1 virus particles per mL of blood plasma ($\leq$50 c/mL), or less than 50 copies of HIV-1 virus particles per mL of blood plasma (<50 c/mL). In other preferred aspects, after at least 48 weeks of once daily administration of the single unit dosage form, the treatment-naïve subject will exhibit a viral load of less than or equal to 50 copies of HIV-1 virus particles per mL of blood plasma ($\leq$50 c/mL), or less than 50 copies of HIV-1 virus particles per mL of blood plasma (<50 c/mL). In other preferred aspects, after at least 96 weeks of once daily administration of the single unit dosage form, the treatment-naïve subject will exhibit a viral load of less than or equal to 50 copies of HIV-1 virus particles per mL of blood plasma ($\leq$50 c/mL), or less than 50 copies of HIV-1 virus particles per mL of blood plasma (<50 c/mL). In other preferred aspects, after 24, 25, 26, 27, 28, 29, 30, 31, 32, 33, 34, 35, 36, 37, 38, 39, 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 7 8, 79, 80, 81, 82, 83, 84, 85, 86, 87, 88, 89, 90, 91, 92, 93, 94, 95, or 96 weeks of once daily administration of the single unit dosage form, the treatment-naïve subject will exhibit a viral load of less than or equal to 50 copies of HIV-1 virus particles per mL of blood plasma ($\leq$50 c/mL), or less than 50 copies of HIV-1 virus particles per mL of blood plasma (<50 c/mL). In some aspects, after more than 96 weeks of once daily administration of the single unit dosage form, the treatment-naïve subject will exhibit a viral load of less than or equal to 50 copies of HIV-1 virus particles per mL of blood plasma ($\leq$50 c/mL), or less than 50 copies of HIV-1 virus particles per mL of blood plasma (<50 c/mL).

In other aspects, after at least 24 weeks of once daily administration of the single unit dosage form, the treatment naïve subject will exhibit the same cluster of differentiation (CD) 4+ cell count, as compared to the subject's CD4+ count prior to the administration. In other aspects, after at least 24 weeks of once daily administration of the single unit dosage form, the subject will exhibit an improved cluster of differentiation (CD) 4+ cell count, as compared to the subject's CD4+ count prior to the administration. Also in these aspects, after at least 48 weeks of once daily administration of the single unit dosage form, the subject will exhibit the same cluster of differentiation (CD) 4+ cell count, as compared to the subject's CD4+ count prior to the administration. In other aspects, after at least 48 weeks of once daily administration of the single unit dosage form, the subject will exhibit an improved cluster of differentiation (CD) 4+ cell count, as compared to the subject's CD4+ count prior to the administration. Also in these aspects, after at least 96 weeks of once daily administration of the single unit dosage form, the subject will exhibit the same cluster of differentiation ((D) 4+ cell count, as compared to the subject's CD4+ count prior to the administration. In other aspects, after at least 96 weeks of once daily administration of the single unit dosage form, the subject will exhibit an improved cluster of differentiation (CD) 4+ cell count, as compared to the subject's CD4+ count prior to the administration.

Also in these aspects, after at least 24 weeks of once daily administration of the single unit dosage form, the treatment-naïve subject does not exhibit an emergent resistance-associated mutation in an HIV virus. In other aspects, after at least 48 weeks of once daily administration of the single unit dosage form, the subject does not exhibit an emergent resistance-associated mutation in an HIV virus. In other aspects, after at least 96 weeks of once daily administration of the single unit dosage form, the subject does not exhibit an emergent resistance-associated mutation in an HIV virus.

Also in these aspects, after at least 24 weeks of once daily administration of the single unit dosage form, the treatment-naïve subject exhibits the same lipid profile, as compared to the subjects lipid profile prior to the administration. In other aspects, after at least 24 weeks of once daily administration of the single unit dosage form, the subject exhibits an improved lipid profile, as compared to the subject's lipid profile prior to the administration. In other aspects, after at least 48 weeks of once daily administration of the single unit dosage form, the subject exhibits the same lipid profile, as compared to the subject's lipid profile prior to the administration. In other aspects, after at least 48 weeks of once daily administration of the single unit dosage form, the subject exhibits an improved lipid profile, as compared to the subject's lipid profile prior to the administration. In other aspects, after at least 96 weeks of once daily administration of the single unit dosage form, the subject exhibits the same lipid profile, as compared to the subject's lipid profile prior to the administration. In other aspects, after at least 96 weeks of once daily administration of the single unit dosage form, the subject exhibits an improved lipid profile, as compared to the subject's lipid profile prior to the administration.

Also in these aspects, after at least 24 weeks of once daily administration of the single unit dosage form, the treatment-naïve subject exhibits the same renal function, as compared to the subject's renal function prior to the administration. In other aspects, after at least 24 weeks of once daily administration of the single unit dosage form, the treatment-naïve subject exhibits improved renal function, as compared to the subject's renal function prior to the administration. In other aspects, after at least 48 weeks of once daily administration of the single unit dosage form, the treatment-naïve subject exhibits the same renal function, as compared to the subject's renal function prior to the administration. In other aspects, after at least 48 weeks of once daily administration of the single unit dosage form, the treatment-naïve subject exhibits improved renal function, as compared to the subject's renal function prior to the administration. In other aspects, after at least 96 weeks of once daily administration of the single unit dosage form, the treatment-naïve subject exhibits the same renal function, as compared to the subject's renal function prior to the administration. In other aspects, after at least 96 weeks of once daily administration of the single unit dosage form, the treatment-naïve subject exhibits improved renal function, as compared to the subject's renal function prior to the administration.

Also in these aspects, after at least 24 weeks of once daily administration of the single unit dosage form, the treatment-naïve subject exhibits the same bone density, as compared to the subject's bone density prior to the administration. In other aspects, after at least 24 weeks of once daily administration of the single unit dosage form, the treatment-naïve subject exhibits improved bone density, as compared to the subject's bone density prior to the administration. In other aspects, after at least 48 weeks of once daily administration of the single unit dosage form, the treatment-naïve subject exhibits the same bone density, as compared to the subject's bone density prior to the administration. In other aspects, after at least 48 weeks of once daily administration of the single unit dosage form, the treatment-naïve subject exhibits improved bone density, as compared to the subject's bone density prior to the administration. In other aspects, after at least 96 weeks of once daily administration of the single unit dosage form, the treatment-naïve subject exhibits the same bone density, as compared to the subject's bone density prior to the administration. In other aspects, after at least 96 weeks of once daily administration of the single unit dosage form, the treatment-naïve subject exhibits improved bone density, as compared to the subject's bone density prior to the administration.

Some embodiments of the disclosure are directed to "test" and "treat" interventions in order to decrease the rate of transmission of HIV, in particular HIV-1, in a population. In preferred aspects, these methods start anti-retroviral treatment at an early phase in a subject's HIV infection, which would reduce the proportion of subjects in the population who do not start anti-retroviral treatment. A "population," as used herein, refers to a geographic area of at least 500 subjects, preferably at least 1000 subjects. In some aspects, the population is associated with a poor linkage to HIV care. According to these methods, a subject of the target population, exhibiting a viral load of greater than or equal to 1000 copies of HIV-1 virus particles per mL of blood plasma ($\geq 1000$ c/mL), is administered, once daily, a single unit dosage form as described herein. The subject of the population treated according to these methods may be treatment experienced. In other aspects, the subject of the population treated according to these methods may be treatment naïve.

Subjects treated according to the methods described herein, including treatment experienced and treatment-naïve subjects, using the described single unit dosage forms, will preferably not exhibit any hepatic impairment prior to administration of the single unit dosage form. Methods of diagnosing a subject's hepatic impairment are known in the art. In some aspects, subjects treated with the described single unit dosage forms will exhibit hepatic impairment classed as Child-Pugh Class A (mild hepatic impairment), prior to administration of a single unit dosage form of the disclosure. In other aspects, subject treated with the described single unit dosage forms will exhibit hepatic impairment classed as Child-Pugh Class B (moderate hepatic impairment), prior to administration of a single unit dosage form of the disclosure.

In preferred aspects, subjects treated according to the methods described, including treatment experienced and treatment-naïve subjects, using the described single unit dosage forms, will not exhibit any detectable amounts of hepatitis B virus, as determined using a hepatitis B surface antigen test, prior to the administration of a described single unit dosage form. In other aspects, subjects treated according to the methods described, including treatment experienced and treatment-naïve subjects, using the described single unit dosage forms, will exhibit detectable amounts of hepatitis B virus, as determined using a hepatitis B surface antigen test, prior to the administration of a described single unit dosage form.

In some aspects, the treatment experienced or treatment naïve subject may have had a prior hepatitis B viral infection, prior to the administration of a described single unit dosage form. In these aspects, the subject may have been effectively treated for the hepatitis B viral infection such that the subject does not exhibit detectable levels of hepatitis B surface antigen. Such subject may exhibit hepatitis B surface antibodies.

In other aspects, the treatment experienced or treatment naïve subject may have a hepatitis B viral infection prior to the administration of a described single unit dosage forms.

In preferred aspects, subjects treated according to the methods described, including treatment experienced and treatment naïve subjects, using the described single unit dosage forms, will not exhibit any detectable amounts of hepatitis C virus, as determined using a hepatitis C surface antigen test, prior to the administration of a described single unit dosage form. In other aspects, subjects treated according to the methods described, including treatment experienced and treatment naïve subjects, using the described single unit dosage forms, will exhibit detectable amounts of hepatitis C virus, as determined using a hepatitis C surface antigen test, prior to the administration of a described single unit dosage form.

In some aspects, the treatment experienced or treatment naïve subject may have had a prior hepatitis C viral infection, prior to the administration of a described single unit dosage form. In these aspects, the subject may have been effectively treated for the hepatitis C viral infection such that the subject does not exhibit detectable levels of hepatitis C surface antigen. Such subject may exhibit hepatitis C surface antibodies.

In other aspects, the treatment experienced or treatment naïve subject may have a hepatitis C viral infection prior to the administration of a described single unit dosage forms.

In preferred aspects, subjects treated according to the methods described, including treatment experienced or treatment naïve subjects, using the described single unit dosage forms, will not exhibit proximal renal tubulopathy, either before or during the administration of a single unit dosage form of the disclosure.

In preferred aspects, subjects treated according to the methods described, treatment experienced and treatment naïve subjects, using the described single unit dosage forms, will not exhibit Fanconi syndrome.

According to the methods described herein, during the administration of the once daily single unit dosage form of the disclosure, monitoring of the subject for adverse events is preferred. For example, subjects can be monitored for Stevens-Johnson Syndrome, toxic epidermal necrolysis, drug rash with eosinophilia and systemic symptoms, and/or acute generalized exanthematous pustulosis. In some aspects, a subject is monitored for Stevens-Johnson Syndrome. In some aspects, a subject is monitored for toxic epidermal necrolysis. In some aspects, a subject is monitored for drug rash with eosinophilia and systemic symptoms. In some aspects, a subject is monitored for acute generalized exanthematous pustulosis.

In some aspects, the single unit dosage forms of the disclosure may be used in combination with additional active ingredients in the treatment of HIV infections. The additional active ingredients may be co-administered separately with a single unit dosage form of the disclosure. The combination may serve to increase efficacy (e.g., by including in the combination a compound potentiating the potency or effectiveness of an active agent according to the disclosure), decrease one or more side effects, or decrease the required dose of the active agent according to the disclosure.

In other preferred aspects, the single unit dosage form of the disclosure is the sole anti-retroviral regime administered to the subject.

According to the methods described herein, the described single unit dosage forms should not be co-administered with certain other therapeutic agents, as recommended by regional agencies. For example, in some regions, the described single unit dosage forms should not be co-administered with astemizole and/or terfenadine. Also according to the methods described herein, in certain regions, the described single unit dosage forms should not be co-administered with a compound or composition selected from the following list:

| | |
|---|---|
| Alpha 1-adrenoreceptor antagonist | alfuzosin |
| Antianginal | ranolazine |
| Antiarrhythmic | dronedarone |
| Anticonvulsants | carbamazepine, phenobarbital, phenytoin |
| Anti-gout | colchicine |
| Antimycobacterial | rifampin |
| Antipsychotic | lurasidone pimozide |
| Ergot derivatives | e.g. dihydroergotamine, ergotamine, methylergonovine |
| GI motility agent | cisapride |
| Herbal product | St. John's wort (*Hypericum perforatum*) |
| Hepatitis C direct-acting antiviral | elbasvir/grazoprevir |
| HMG-CoA reductase inhibitors | lovastatin, simvastatin |
| PDE-5 inhibitor | sildenafil when used for treatment of pulmonary arterial hypertension |
| Sedatives/hypnotics | orally administered midazolam triazolam, |

Oral tablets of the disclosure may alternatively include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, microcrystalline sellulose, silicified microcrystalline cellulose, mannitol, sorbitol, and the like. Starch, polyvinyl-pyrrolidone (PVP), sodium starch glycolate, microcrystalline cellulose, carboxymethylcellulose, and alginic acid are suitable disintegrating agents. Binding agents may include starch and gelatin. The lubricating agent, if present, may be magnesium stearate, stearic acid, sodium stearyl fumarate, or talc. If desired, the tablets may be coated with an esthetic coating based on, for example, hydroxypropyl methyl cellulose or polyvinyl alcohol copoymers together with wetting, anti-tacking, and/or coloring agents, and the like. If desired, the tablets may be coated with materials such as, for example, glyceryl monostearate or glyceryl distearate to delay absorption in the gastrointestinal tract, or may be coated with an enteric coating.

Oral tablets of the disclosure may alternatively include a compound according to the disclosure mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

In addition to tablets, the single unit dosage forms of the disclosure may be presented as capsules, for example, hard and soft gelatin capsules. To prepare hard gelatin capsules, compounds of the disclosure may be mixed with a solid, semi-solid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Manufacturing a multi-component, single unit dosage form, in particular one that comprises four active agents, wherein at least one of those agents must be present in large amounts, for example, about 400 to about 1200 mg, preferably about 800 mg in the single unit dosage form, is challenging. One particular challenge is manufacturing a multi-component formulation that accommodates large dosage ranges and keeps the dosage form small enough for a subject to swallow. Single unit dosage forms of the disclosure can be prepared according to methods known in the art, for example, methods described in WO2013/004816 and WO2013004818, the entireties of which are incorporated by reference herein.

For example, preferred methods of making a single unit dosage form of the disclosure comprising mixing
  darunavir, or a hydrate or solvate thereof;
  cobicistat;
  emtricitabine; and
  tenofovir, a tenofovir prodrug, a pharmaceutically acceptable salt of tenofovir, or a pharmaceutically acceptable salt of a tenofovir prodrug; and
  a microcrystalline cellulose and a croscarmellose sodium for a time sufficient to form a first mixture. Typically, about 5 to about 30 minutes, preferably about 5 to about 20 minutes; with 15 minutes being most preferred, is sufficient to form the first mixture.

The first mixture is mixed with a first lubricant, for example, a stearate such as magnesium stearate, for a time sufficient to form a second mixture. Typically about 1 to 15 minutes, preferably about 2 to 5 minutes, is sufficient to form the second mixture.

The second mixture is compacted to form a compacted mixture. The compaction method is preferably a dry technique, that is, no liquids are needed as processing aids. For example, in preferred methods, the compaction method is a roller compaction. Roller compaction is a particularly preferred method for use in those embodiments that include tenofovir alafenamide fumarate or tenofovir alafenamide hemifumarate, which is moisture sensitive. The compaction uses about 4 to about 10 or about 6 to about 10 or about 5 to 9, preferably 9 kN/cm roller pressure. It is preferred that the compaction uses about a 1.5 to about a 3 mm, preferably about 2.5 mm, roller gap.

The compacted mixture is milled to form granules. An oscillating mill method is preferred. Also preferred is a screen size of about 1.5 mm.

The granules are mixed with a second lubricant, for example, a stearate such as magnesium stearate, for a time sufficient to produce a granule mixture. Typically about 1 to 10 minutes, preferably about 2 to 4 minutes, with about 3 minutes being most preferred, is sufficient to produce the granule mixture.

The granule mixture is compressed into one or more tablets, using methods known in the art. Optionally, the one or more tablets can be coated with a coating layer.

Preferred tablets of the disclosure will have a major axis of about 20 to 25 mm, preferably 22 mm. Also preferred are tablets that have a minor axis of about 8 to 15 mm, preferably 11 mm. In other aspects, the tablets have a major axis of 21 mm or 10 mm and a minor axis of 5 or 6 mm.

In preferred embodiments, the single unit dosage forms of the disclosure, when in the form of tablets, are of a sufficient structural integrity that they can be split, preferably into two or more pieces, for those subjects who have difficulties in swallowing larger-sized tablets. Score lines may be implemented to aid in splitting of the dosage forms.

The following examples are merely illustrative and are not intended to limit the disclosure to the materials, conditions, or process parameters set forth therein.

EXAMPLES

Example 1

Phase 3, Randomized Active-Controlled, Open Label Study to Evaluate the Efficacy, Safety and Tolerability of Switching to a Darunavir/Cobicistat/Emtricitabine/Tenofovir Alafenamide (D/C/F/TAF) Once-Daily Single-Tablet Regimen This is a randomized (study medication assigned to participants by chance) (2:1), active-controlled (study in which the experimental treatment or procedure is compared to a standard treatment or procedure), open-label (participants and researchers are aware about the treatment, participants are receiving), multicenter (when more than 1 hospital or medical school team work on a medical research study), parallel-group, non-inferiority study in virologically-suppressed, HIV-1 infected adult participants. The study includes a Screening Period of approximately 30 days (up to maximum 6 weeks), a controlled Treatment Period of 48 weeks, an Extension Phase of 48 weeks. All eligible participants will be randomly assigned to receive either current treatment regimen—a boosted protease inhibitor (bPI) (limited to darunavir with low-dose ritonavir [rtv] or cobicistat, atazanavir [ATV] with rtv or cobicistat, or lopinavir [LPV] with rtv) combined with emtricitabine/tenofovir disoproxil fumarate, or experimental treatment regimen—D/C/F/TAF once-daily single-tablet for 48 weeks. After completion of week 48, participants assigned to the experimental treatment continued with D/C/F/TAF in the extension phase up to week 96. Participants who continued their current regimen will receive the experimental treatment (if all criteria are fulfilled) at week 52 up to week 96. As from Week 96, all participants will be given the option to continue D/C/F/TAF treatment, if they wish and if they continue to benefit from it until D/C/F/TAF becomes commercially available and is reimbursed, or can be accessed through another source in the country where he/she is living, or until the sponsor terminates clinical development. A bone investigation substudy was performed at selected study sites, to assess bone biomarkers and energy x-ray absorptiometry (DXA) scans, in approximately 300 participants (200 in the D/C/F/TAF treatment arm versus 100 in the control arm) who provide informed consent for the substudy.

Experimental Treatment Study Arm (SG): Participants received a single fixed dose combination (FDC) tablet containing darunavir (DRV) 800 milligram (mg)/cobicistat (COBI) 150 mg/emtricitabine (FTC) 200 mg/tenofovir alafenamide (TAF) 10 mg (D/C/F/TAF tablet), orally once daily, up to Week 48. After Week 48, all participants will continue to receive the D/C/F/TAF tablet in a 48 week extension phase (up to Week 96).

Active Comparator Study Arm (CG): Participants will receive a boosted protease inhibitor (bPI) (limited to darunavir or atazanavir with low-dose ritonavir [rtv] or cobicistat, or lopinavir with rtv) combined with emtricitabine/tenofovir disoproxil fumarate (FTC/TDF (tenofovir diisoproxil fumarate)) up to Week 52. After Week 52, all participants will receive the D/C/F/TAF tablet in a 44 week extension phase (up to Week 96).

Inclusion Criteria (Study Open to All Sexes, 18 Years and Older):

Currently being treated with a stable anti-retroviral (ARV) regimen consisting of a boosted protease inhibitor (limited to darunavir or atazanavir with low-dose ritonavir [rtv] or cobicistat, or lopinavir with rtv) combined with emtricitabine/tenofovir disoproxil fumarate (FTC/TIN) only, for at least 6 consecutive months preceding the Screening visit On-treatment plasma human immunodeficiency virus type 1 ribonucleic acid (HIV-1 RNA) concentrations less than (<) 50 copies per milliliter (copies/mL) or HIV-1 RNA undetectable by a local HIV-1 RNA test between 12 and 2 months prior to the Screening visit and have HIV-1 RNA<50 copies/mL at the Screening visit A single virologic elevation of greater than or equal to (>=) 50 copies/mL after previously reaching viral suppression between 12 and 2 months prior to Screening is acceptable, provided a subsequent test prior to Screening was <50 copies/mL Absence of history of failure on DRV treatment and absence of DRV resistance-associated mutations (RAMs), if documented historical genotypes are available Normal electrocardiogram (ECG) at Screening (or if abnormal, determined by the Investigator to be not clinically significant)

Exclusion Criteria:

A new acquired immunodeficiency syndrome (AIDS)-defining condition diagnosed within the 30 days prior to Screening Proven or suspected acute hepatitis within 30 days prior to study entry Hepatitis C antibody positive; however, participants previously cured of hepatitis C virus (HCV) infection, with documented sustained virologic response, that is, undetectable HCV RNA 24 weeks after the last dose of HCV treatment, are allowed to participate Hepatitis B surface antigen (HBsAg) positive Participants with cirrhosis as diagnosed based on local practices See also, https://clinicaltrials.gov/ct2/show/NCT02269917?term=D%2FC%2FF%2FTAF&age=1&phase=2&draw=1&rank=1, the disclosure of which is incorporated by reference, herein.

Results After 24 Weeks:

1141 patients were treated (SG N=763 vs CG N=378). Baseline characteristics: median age 46 years; 18% women; 25% non-white (21% black); 10% $CD4^+$<350 cells/$mm^3$; 71%, 22%, and 8% on darunavir, atazanavir and lopinavir, respectively (15% on cobicistat).

Cumulative virologic rebound (VR) was 1.8% (SG n=14) vs 2.1% (CG n=8), of which for 10 and 5 respectively, re-virologic suppression (re-VS) obtained by Week 24; there were no confirmed rebounds≥200 c/mL. At Week 24, FDA snapshot analysis showed VS was obtained for 96.3% of SG and 95.5% of CG, and virologic failure (VF) occurred in 0.5% and 0.8%, respectively, with no discontinuations for VF and no detected resistance to any study drug.

Safety was similar between arms through 24 weeks, with low incidences of Grade 3-4 adverse events (AE) (SG 4.5% vs CG 4.5%), serious AE (2.6% vs 3.2%), and treatment discontinuations (overall, 2.9% vs 2.9%; due to AE, 1.4% vs 1.1%). The most common AE (≥5% both arms) were: nasopharyngitis (7.6% vs 6.6%), URI (6.3% vs 6.3%), vitamin D deficiency (5.5% vs 5%). There were no deaths. Total cholesterol/HDL-cholesterol ratios were similar between arms, with minimal changes from baseline. Changes from baseline in renal safety parameters were consistent with known profiles of the individual D/C/F/TAF components. Mean ΔeGFR (cystatin-C clearance by CKD-EPI): SG+0.3 vs CG-1.0 mL/min/1.73 $m^2$.

In virologically suppressed adults, switching to once-daily D/C/F/TAF was well tolerated, and resulted in a low cumulative virologic rebound rate and high viral suppression rates through 24 weeks.

Results After 48 Weeks:

1141 patients were randomized and treated (N=763 D/C/F/TAF versus N=378 control); median age 46; 18% women; 25% non-white; 58% on previous ARVs. Cumulative virologic rebound through week 48 was 2.5% (n=19 D/C/F/TAF) versus 2.1% (n=8 control) (difference: 0.4%, 95% CI-1.5%; 2.2%; $p_{non-inferiority}$<0.0011). Most rebounders (12/19 and 4/8, respectively) resuppressed by Week 48. Virologic suppression (VL<50 c/mL; FDA snapshot) at Week 48 was 94.9% versus 93.7%. Only 6 (0.8%) versus 2 (0.5%) patients had VL≥50 c/mL, with no discontinuations for virologic failure or emergent resistance to any study drug. Safety through 48 weeks was similar between arms, with low incidences of treatment discontinuations due to adverse events (AEs) (1.4% vs 1.1%), Grade 3-4 AEs (6.7% vs 7.9%) and serious AEs (4.5% vs 4.8%), and no deaths. Changes from baseline to Week 48 in renal and bone markers were more favorable for D/C/F/TAF versus control (Table 1), with no difference in total cholesterol/HDL-cholesterol between arms.

Percentage virologic rebound after switching to the once-daily STR, D/C/F/TAF, was non-inferior to control through 48 weeks, with improved bone and renal safety markers and among the highest virologic suppression rates seen for a bPI-based regimen.

TABLE 1

Changes from baseline at Week 48 in renal and bone safety parameters

|  | D/C/F/TAF N = 763 | Control N = 378 | P-value* |
|---|---|---|---|
| Mean change in eGFR$_{cyst}$, mL/min/1.73 m$^2$ | −0.4 | −1.8 | 0.034 |
| Mean changes in renal biomarkers |  |  |  |
| Urine protein:creatinine ratio (mg/g) | −33.90 | −6.43 | <0.001 |
| Urine albumin:creatinine ratio (mg/g) | −3.20 | +1.25 | <0.001 |
| Urine Retinol Binding Protein:creatinine ratio (μg/g) | −630.45 | +1037.06 | <0.001 |
| Urine Beta-2-Microglobulin:creatinine ratio | −1454.70 | +1371.29 | <0.001 |
| Proportion of patients with ≥3% changes in BMD Lumbar spine |  |  |  |
| Increase by ≥3% | 31.8% | 8.9% | <0.001 |
| Decrease by ≥3% | 7.8% | 19.8% | <0.001 |
| Total hip |  |  |  |
| Increase by ≥3% | 20.2% | 4.1% | <0.001 |
| Decrease by ≥3% | 2.1% | 8.2% | <0.001 |

*Between treatment comparison assessed with Van Elteren test, controlling for boosted PI used at screening;
eGFR$_{cyst}$ = eGFR cystatin C clearance (CKD-EPI formula);
BMD = bone mineral density Virological rebound was cumulative through 48 weeks. Virological response (assessed via US FDA snapshot algorithm) and CD4+ cell count changes were assessed at 48 weeks. BL values are medians.

Results After 96 Weeks:

Of 1141 randomized and treated patients (58% had received≥5 previous ARVs including screening ARVs; 15% had previous non-DRV VF), 1080 continued in the extension phase (N=728 D/C/F/TAF; N=352 late switch). Few patients had virologic rebound cumulative through week 96 in the D/C/F/TAF arm (3.1%, 24/763). Virologic rebound occurred in 2.3% (8/352) in the late switch arm over 44 weeks D/C/F/TAF treatment, Many rebounders (14/24 and 2/8) resuppressed by week 96. Many of the patients with virological rebound (ITT analysis) achieved suppression again by week 96 (i.e., they had VL<50 copies/mL by the FDA-snapshot approach) (14/24 D/C/F/TAF group through week 96; 2/8 late switch group from week 52 through week 96). There were 4/763 (0.5%) and 2/352 (0.6%) confirmed rebounds (VL≥200 copies/mL), respectively. At week 96, a high % of patients in the D/C/F/TAF arm (90.7%, 692/763) were suppressed (VL<50 c/mL). In the late switch arm 93.8% (330/352) maintained virologic suppression after 44 weeks. No DRV, primary PI, TFV or FTC RAMs were seen post baseline. Few serious AEs and AE related discontinuations occurred in either arm (Table 1B). Improvements in renal and bone parameters were maintained in the D/C/F/TAF arm and seen in the late switch arm (week 52-96), with a small change in TC-HDL-C ratio (Table 1B).

Switching to D/C/F/TAF maintained high virologic suppression rates (>90%) at week 96 with no resistance development, and was well tolerated over 96 weeks with bone, renal and lipid safety consistent with known TAF and cobicistat profiles. Efficacy and safety results in the late switch arm were consistent with week 48 results in the D/C/F/TAF arm. D/C/F/TAF combines the efficacy and high genetic barrier to resistance of DRV with the safety benefits of TAF, even in patients with a history of non-DRV VF.

TABLE 1A

Efficacy of switching to the darunavir/cobicistat/emtricitabine/tenofovir alafenamide single-tablet regimen in virologically-suppressed adults with HIV-1 infection in EMERALD.[1]

| Regimen[a] (no. of intent-to-treat pts) | Virological rebound[b] (% of pts) [95% CI] | Virological response[c] (% of pts) | | | Mean change from BL [BL] in CD4+ cells/μL |
|---|---|---|---|---|---|
|  |  | VL < 20 copies/mL | VL < 50 copies/mL | VL < 200 copies/mL |  |
| bPI[d] + FTC + TDF → DRV/COB/FTC/TAF (763) | 2.5 [−1.5 to 2.2][e] | 89.8 | 94.9 | 95.0 | 19 [630] |
| bPI[d] + FTC + TDF (378) | 2.1[e] | 88.4 | 93.7 | 94.2 | 5 [624] |

BGD between-group difference, BL baseline, bPI boosted protease inhibitor, COB cobicistat, DRV darunavir, FTC emtricitabine, pts patients, TAF tenofovir alafenamide, TDF tenofovir disoproxil fumarate, VL viral load (i.e. plasma HIV-1 RNA level), → switched at BL to

[a]Dosage of antiretrovirals, where specified, was DRV/COB/FTC/TAF 800/150/200/10 mg

[b]Defined as confirmed, VL ≥ 50 copies/mL or premature discontinuation with last VL ≥ 50 copies/mL; primary endpoint

[c]P-values for BGDs were not reported

[d]Once-daily DRV or atazanavir boosted with ritonavir or COB, or twice-daily lopinavir boosted with ritonavir

[e]Switching to DRV/COB/FTC/TAF was noninferior to continuing bPI + FTC + TDF, as upper bound of 95% CI for the BGD was <4%

[1]Orkin C, Molina J-M, Negredo E, et al. Efficacy and safety of switching from boosted protease inhibitors plus emtricitabine and tenofovir disoproxil fumarate regimens to single-tablet darunavir, cobicistat, emtricitabine, and tenofovir alafenamide at 48 weeks in adults with virologically suppressed HIV-1 (EMERALD): a phase 3, randomised, non-inferiority trial. Lancet HIV. 2017.

TABLE 1B

Treatment-emergent Adverse Events and changes in renal, lipid and bone parameters at Week 96

| | D/C/F/TAF arm | | | Late switch arm | | |
|---|---|---|---|---|---|---|
| | D/C/F/TAF (baseline-week 48) N = 763 | D/C/F/TAF (baseline-week 96) N = 763 | P-value[†,‡] | bPI + F/TDF (baseline-week 52) N = 378 | D/C/F/TAF* (week 52-week 96) N = 352 | P-value[†,‡] |
| Treatment-emergent AEs, n (%) | | | | | | |
| AEs, any grade | 630 (82.6) | 690 (90.4) | ND | 316 (83.6) | 258 (73.3) | ND |
| Grade 3-4 AEs | 54 (7.1) | 98 (12.8) | ND | 31 (8.2) | 26 (7.4) | ND |
| Serious AEs | 35 (4.6) | 66 (8.7) | ND | 18 (4.8) | 21 (6.0) | ND |
| AE-related discontinuations | 12 (1.6) | 17 (2.2) | ND | 5 (1.3) | 7 (2.0) | ND |
| Deaths | 0 | 3[§] (0.4) | ND | 0 | 0 | ND |
| Median change in eGFR | | | | | | |
| $eGFR_{cyst}$, mL/min/1.73 m² | 0.0 | −0.9 | 0.018 | −1.9 | 1.0 | 0.051 |
| $eGFR_{cr}$, mL/min/1.73 m² | −0.7 | −1.3 | <0.001 | −0.6 | −0.7 | 0.007 |
| Median changes in renal biomarkers | | | | | | |
| UPCR (mg/g) | −22.18 | −22.23 | <0.001 | −7.37 | −12.81 | <0.001 |
| UACR (mg/g) | −0.78 | −0.63 | <0.001 | 0.40 | −0.93 | <0.001 |
| RBP:Cr (μg/g) | −27.33 | −25.08 | <0.001 | +19.66 | −39.07 | <0.001 |
| B2M:Cr (μg/g) | −66.63 | −68.22 | <0.001 | +20.24 | −110.31 | <0.001 |
| Median change in fasting lipids | | | | | | |
| TC (mg/dL) | +19.7 | +22.0 | <0.001 | +1.3 | +22.0 | <0.001 |
| HDL-C (mg/dL) | +2.7 | +3.0 | <0.001 | 0.0 | +3.3 | <0.001 |
| LDL-C (mg/dL) | +15.7 | +17.0 | <0.001 | +1.9 | +15.0 | <0.001 |
| Triglycerides (mg/dL) | +5.3 | +7.0 | <0.001 | +4.9 | +8.0 | 0.004 |
| TC/HDL-C ratio | +0.20 | +0.20 | <0.001 | +0.10 | +0.20 | <0.001 |
| Changes in BMD | N = 209 | N = 209 | | N = 108 | N = 105 | |
| Lumbar spine | | | | | | |
| Mean % change | +1.45 | +1.99 | <0.001 | −0.63 | +2.91 | <0.001 |
| Increase by ≥3% | 31.2% | 36.6% | ND | 9.1% | 43.4% | ND |
| Decrease by ≥3% | 7.9% | 9.3% | ND | 20.2% | 2.0% | ND |
| Total hip | | | | | | |
| Mean % change | +1.49 | +1.86 | <0.001 | −0.27 | +1.22 | <0.001 |
| Increase by ≥3% | 21.0% | 28.8% | ND | 4.2% | 24.0% | ND |
| Decrease by ≥3% | 2.2% | 3.1% | ND | 8.4% | 5.2% | ND |
| Femoral neck | | | | | | |
| Mean % change | +0.74 | +1.40 | <0.001 | −0.51 | +0.98 | 0.019 |
| Increase by ≥3% | 24.2% | 28.8% | ND | 11.6% | 29.2% | ND |
| Decrease by ≥3% | 10.2% | 8.6% | ND | 17.9% | 9.4% | ND |

*Comprising 44 weeks of D/C/F/TAF exposure (i.e., from the switch to D/C/F/TAF at Week 52)
[†]Within treatment arm comparisons for change at week 96 from reference assessed by: Wilcoxon signed-rank test (eGFR, renal biomarkers and fasting lipids) and paired t-test (BMD)
[‡]Reference for the D/C/F/TAF arm is study baseline and for the late switchers is the last value before the switch
[§]Three deaths were due to metastatic pancreatic carcinoma and two cases of myocardial infarction, one of which was considered related to D/C/F/TAF in a patient who was a smoker, with a history of hypertension, coronary artery disease and obesity.
$eGFR_{cyst}$ = eGFR based on serum cystatin C (CKD-EPI formula); $eGFR_{cr}$ = eGFR based on serum creatinine (CKD-EPI formula); UPCR = urine protein:creatinine ratio; UACR = urine albumin:creatinine ratio; RBP:Cr = urine Retinol Binding Protein:creatinine ratio; B2M:Cr = urine Beta-2-Microglobulin:creatinine ratio; TC = total cholesterol; HDL-C = high-density lipoprotein-cholesterol; LDL-C = low-density lipoprotein-cholesterol; BMD = bone mineral density; ND = not determined.

Example 2

Phase 3, Randomized, Active-Controlled, Double-Blind Study to Evaluate Efficacy and Safety of D/C/F/TAF Once Daily Fixed Dose Combination Regimen in Antiretroviral Treatment-Naïve Human Immunodeficiency Virus Type I Infected Subjects This is a Phase 3, international, multicenter (when more than one hospital or medical school team work on a medical research study), randomized (1:1) (study drug assigned by chance), double-blind (a medical research study in which neither the researchers nor the participant know what treatment the participant is receiving), parallel-group, active-controlled (study in which the experimental treatment or procedure is compared to a standard [control] treatment or procedure) study. The study consists of 5 periods: a Screening period, Double-blind treatment period, Single-arm treatment period, Extension period and a Follow-up period. Participants receive either darunavir (DRV)/cobicistat (COBI)/emtricitabine (FTC)/tenofovir alafenamide (TAF) fixed dose combination (D/C/F/TAF FDC) or DRV/COBI FDC along with FTC/TDF FDC. Primarily percentage of participants with human immunodeficiency virus (HIV)-1 Ribonucleic acid (RNA) less than (<) 50 copies per milliliter (copies/ml) defined by snapshot analysis will be evaluated. Participants' safety will be monitored throughout the study.

Experimental Treatment Study Arm (SG): Subjects received a single oral tablet containing darunavir (DRV) 800 milligram (mg)/cobicistat (COBI) 150 mg/emtricitabine (FTC) 200 mg/tenofovir alafenamide (TAF) 10 mg (D/C/F/TAF fixed dose combination [FDC]) once daily along with DRV/COBI FDC-matching and FTC/TDF FDC-matching placebo tablets once daily up to Week 48 analysis unblinding visit (i.e. after last subject has reached Week 48). After Week 48 analysis unblinding visit, subjects will receive a single tablet containing D/C/F/TAF FDC once daily up to Week 96.

Active Comparator Study Arm (CG): Subjects received DRV 800 mg/COBI 150 mg FDC and FTC 200 mg/TDF 300 mg FDC along with D/C/F/TAF FDC-matching placebo tablet once daily up to Week 48 analysis unblinding (i.e. after last subject has reached Week 48). After Week 48 analysis unblinding, subjects will receive a single tablet containing D/C/F/TAF FDC once daily up to Week 96.

Inclusion Criteria (Study Open to All Sexes, 18 Years and Older):

Subject must be anti-retroviral (ARV) treatment-naïve (never treated with an ARV including post-exposure prophylaxis and pre-exposure prophylaxis); no prior use of any approved or experimental anti-human immunodeficiency virus (anti-HIV) drug for any length of time Screening plasma HIV-1 ribonucleic acid (RNA) level greater than or equal to >=1,000 copies per milliliter (copies/mL)

Cluster of Differentiation 4+ (CD4+) cell count>50 cells/microliter (cells/mcL)

Screening HIV-1 genotype report must show full sensitivity to DRV, TDF and FTC

Screening eGFRcreatinine>=70 mL/min according to the Cockcroft-Gault formula for creatinine clearance Exclusion Criteria:

Subject has been diagnosed with a new acquired immunodeficiency syndrome (AIDS)-defining condition within the 30 days prior to screening Subject has proven or suspected acute hepatitis within 30 days prior to screening Subject is hepatitis C or hepatitis B positive Subject has a history of cirrhosis Procedures The trial included a screening period of approximately 30 days (up to maximum of 6 weeks) before the baseline visit, a 48-week double blindtreatment period, and an open-label, single-arm treatment phase during which all patients received D/C/F/TAF up to week 96 after being unblinded, and will continue taking D/C/F/TAF in a roll-over extension phase until commercial availability of the regimen.

Study visits were scheduled for baseline, weeks 2, 4, 8 and 12, and then every 12 weeks until week 96, with a visit 3 to 7 weeks after the unblinding visit only for patients in the control group. Those who prematurely discontinued study medications were also required to attend a visit within 72 hours. Any patient who had an ongoing adverse event or serious adverse event at the last study visit was required to attend a 30-day follow-up visit unless consent had been withdrawn.

At each visit, treatment adherence (except at week 2) by drug accountability (pill count and patient log booklet), concomitant medications and adverse events were monitored. Plasma viral load, CD4+ cell count, biochemistry, haematology, urinalysis and urine chemistry, serum cystatin C for calculating $eGFR_{cyst}$ by the Chronic Kidney Disease Epidemiology Collaboration (CKD-EPI) formula, and serum creatinine for calculating $eGFR_{cr}$ (Cockcroft-Gault formula and CKD-EPI formula) were evaluated. The renal proteinuria biomarkers, urinary retinol binding protein and beta-2-microglobulin, were measured at baseline, weeks 2, 4, 12, 24 and 48 in the fasted state. Fasted metabolic profile assessments (total, high-density lipoprotein [HDL]- and low-density lipoprotein [LDL]-cholesterol, triglycerides) were performed at baseline, weeks 24 and 48.

Plasma viral load was quantified using the COBAS AmpliPrep/COBAS TaqMan HIV-1 Test, V2.0 (Roche Diagnostics, Basel, Switzerland). Protocol-defined virologic failure was defined as virologic nonresponse (viral load<1 $\log_{10}$ reduction from baseline and ≥50 copies per mL at week 8, confirmed at next visit) or virologic rebound (confirmed viral load≥50 copies per mL after confirmed, consecutive viral load<50 copies per mL or confirmed viral load>1 $\log_{10}$ increase from the nadir) and/or viremia at the final time point (viral load≥400 copies per mL at study endpoint or study discontinuation after week 8). Post-screening resistance testing (PhenoSense GT, a combination genotypic/phenotypic resistance test) was performed on samples from patients with protocol-defined virologic failure and who had viral load≥400 copies/mL at failure (preferably confirmed, or otherwise at unconfirmed) virologic failure time-point) or at later time points.

The bone investigation substudy was performed at selected study sites in consenting patients from both randomisation groups. Dual energy x-ray absorptiometry (DXA) scans were performed to determine BMD of the hip, spine and femoral neck at baseline, weeks 24 and 48. Levels of the bone biomarkers, parathyroid hormone, and 25-hydroxy vitamin D were measured in the fasted state, at baseline, weeks 24 and 48. Alkaline phosphatase, C-type collagen sequence (markers of bone resorption), and procollagen type N-terminal propeptide (marker of bone formation) were measured at weeks 2, 4, 12, 24, and 48.

The Division of AIDS grading table was used to grade any adverse events and clinically significant laboratory abnormalities. Adverse events were coded using the Medical Dictionary for Regulatory Activities (version 19.1). All clinical laboratory testing was performed by a central laboratory.

Statistical Analysis

The week 48 primary analysis was performed on the intent-to-treat population (comprising all patients who were randomised and received ≥1 dose of study drug). A per-protocol analysis was also performed, excluding patients with major protocol violations or other predefined criteria that potentially affected efficacy. Data analysis was performed using SAS software (SAS Institute, Inc, Cary, N.C., USA) version 9.2.

Assuming a response rate of 80% at week 48 (viral load<50 copies per mL, FDA-snapshot analysis) for both treatment groups, 335 patients needed to be enrolled in each group to establish non-inferiority of D/C/F/TAF to control, with a non-inferiority margin of 10% at 90% power and a 1-sided significance level of 2.5%. For the bone investigation substudy, a minimum of 85 patients per treatment group were required to detect an absolute difference between groups in BMD of ≥2% with 90% power, assuming a 4% inter-subject variability and a 1-sided significance level of 2.5%.

Non-inferiority of D/C/F/TAF to control would be demonstrated if the lower limit of the 2-sided 95% CI of the stratum-adjusted (viral load< or >100 000 copies per mL and CD4+ cell count< or ≥200 cells per mm$^3$) Mantel-Haenszel difference between treatment groups (D/C/F/TAF minus control) in the week 48 response rate was greater than −10%. Superiority would be established if the lower limit of the 95% CI was >0.

The difference between groups in least square mean change from baseline at week 48 in CD4$^+$ cell count and associated 95% CIs were constructed using ANCOVA, including CD4$^+$ cell count at baseline as a continuous covariate. In patients who discontinued, CD4+ values after discontinuation were imputed with the baseline value (non-completer=failure). Other (intermittent) missing values were imputed using last observation carried forward.

Baseline and post-baseline HIV-1 genotypes were analysed for protease mutations (including international Antiviral Society [IAS]-USA primary protease inhibitor resistance-associated mutations) and reverse transcriptase mutations (including IAS-USA NRTI resistance-associated mutations and IAS-USA NNRTI resistance-associated mutations), as well as specific mutations associated with resistance to the study drugs. Antiretroviral sensitivity, based on the genotype/phenotype report; was also assessed.

Within-treatment comparisons of mean changes from baseline at weeks 24 and 48 in renal and bone biomarkers, and fasting lipids were performed using the Wilcoxon signed-rank test. Between-treatment comparisons were assessed using the Wilcoxon rank-sum test. Between-treatment differences in change from baseline at weeks 24 and 48 in serum creatinine, eGFR and BMD were tested using ANCOVA, including treatment as a factor and corresponding baseline values as covariates.

This study is registered with ClinicalTrials.gov, number NCT02431247, and EudraCT, number 2015-000754-38, with sponsor protocol number TMC114FD2HTX3001. See also; https://clinicaltrials.gov/ct2/show/NCT02431247?term=D%2FC%2FF%2FTAF&age=1&phase=2&draw=1&rank=2.

Figure 4:
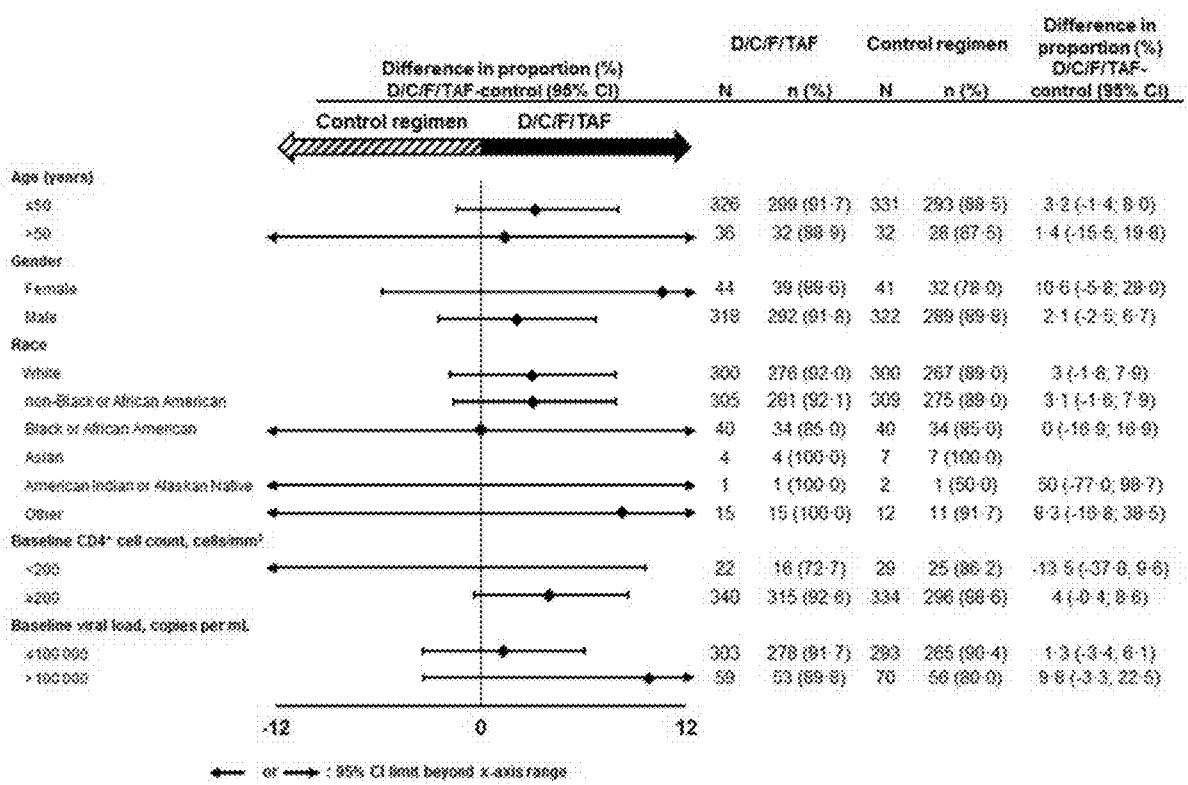
FIG. 4: Subgroup analyses of week 48 response rates (<50 copies per mL; FDA-snapshot analysis). CI, confidence interval; D/C/F/TAF=darunavir/cobicistat/emtricitabine/tenofovir alafenamide; Control regimen=darunavir/cobicistat plus emtricitabine/tenofovir disoproxil fumarate once daily.

Results After 48 Weeks 725 patients (362 D/C/F/TAF; 363 control) were randomized and treated; median age 34 yrs, 12% women, 83% white, 7% CD4 count<200 cells/mm$^3$ and 18% VL≥100,000 c/mL. Median baseline viral load was 4.52 log$_{10}$ copies per mL (IQR. 4.10-4.87). Median baseline CD4+ cell count was 453 cells per mm$^3$ (ICER 333-601). See FIG. 4 and Table 2, below.

TABLE 2

| Demographics n (%), unless stated | D/C/F/TAF 800/150/200/10 mg QD N = 362 | Control (DRV/COBI + F/TDF) QD N = 363 | Total N = 725 |
|---|---|---|---|
| Median age (range), years | 34 (19-61) | 34 (18-71) | 34 (18-71) |
| >50 | 36 (9.9%) | 32 (8.8%) | 68 (9.4%) |
| Gender | | | |
| Female | 44 (12.2%) | 41 (11.3%) | 85 (11.7%) |
| Male | 318 (87.8%) | 322 (88.7%) | 640 (88.3%) |
| Race | | | |
| White | 300 (82.9%) | 300 (82.6%) | 600 (82.8) |
| Black/African-American | 40 (11.0%) | 40 (11.0%) | 80 (11.0) |
| Asian/other races | 22 (6.1%) | 23 (6.3%) | 45 (6.2) |
| Ethnicity | | | |
| Hispanic or Latino | 50 (13.8%) | 45 (12.5%) | 95 (13.2%) |
| Region | | | |
| Europe | 282 (77.9%) | 278 (76.6%) | 560 (77.2%) |
| North America | 80 (22.1%) | 85 (23.4%) | 165 (22.8%) |
| Baseline disease characteristics | | | |
| Median (range) time since diagnosis, months | 5.73 (0.6-194.3) | 4.30 (0.7-310.3) | 4.83 (0.6-310.3) |
| Median (range) log$_{10}$ VL, copies per mL | 4.44 (1.28-6.6) | 4.57 (2.99-6.68) | 4.52 (1.28-6.68) |
| VL ≥100,000 copies per mL | 60 (16.6%) | 70 (19.3%) | 130 (17.9%) |
| Median (range) CD4$^+$ cell count, cells per mm$^3$ | 461.5 (46-1454) | 440.0 (38-1456) | 453.0 (38-1456) |
| CD4$^+$ cell count <200 cells per mm$^3$ | 22 (6.1%) | 29 (8.0%) | 51 (7.0%) |
| Media (range) eGFR$_{cr}$, mL/min (Cockcroft-Gault) | 119.3 (74-257) | 118.4 (57-207) | 119.1 (57-257) |
| Genotype* at screening (Johnson, et al. 2010) | N = 361† | N = 362† | N = 723 |
| ≥1 DRV RAMs | 3 (0.8%)‡ | 4 (1.1%)‡ | 7 (1.0%) |
| ≥1 primary PI RAMs | 7 (1.9%) | 8 (2.2%) | 15 (2.1%) |
| ≥1 secondary PI RAMs | 354 (98.1%) | 354 (97.8%) | 708 (97.9%) |
| ≥1 NRTI RAMs | 18 (5.0%) | 16 (4.4%) | 34 (4.7%) |
| ≥1 NNRTI RAMs | 55 (15.2%) | 63 (17.4%) | 118 (16.3%) |

Figure 3:
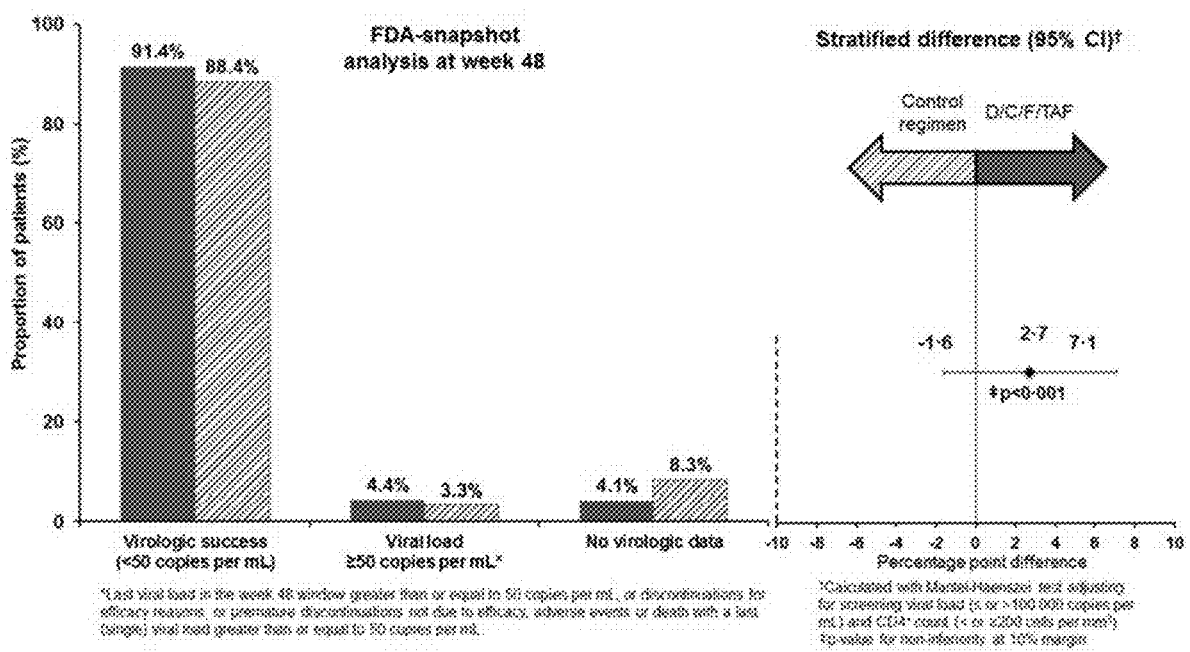
FIG. 3: Week 48 virologic outcomes in the FDA-snapshot analysis. CI, confidence interval; D/C/F/TAF=darunavir/cobicistat/emtricitabine/tenofovir alafenamide; Control regimen=darunavir/cobicistat plus emtricitabine/tenofovir disoproxil fumarate once daily.

At Week 48, virologic response rate (FDA Snapshot) was 91.4% for D/C/F/TAF vs 88.4% for control (Δ2.7%; 95% CI: −1.6%; 7.1%; p$_{non-inferiority}$<0.0001). See FIG. 3. Among virologic failures (VL≥50 c/mL per Snapshot; 4.4% vs. 3.3%), there were no discontinuations and no treatment-emergent resistance to darunavir or TAF.

Results from the per-protocol analysis were consistent with the primary endpoint by intent-to-treat, confirming non-inferiority of D/C/F/TAF (94.0% [327/348]) (95% CI 90.9 to 96.2) to control (92.2% [317/344]) (95% CI 88.8 to 94.8) (difference 1.5%; 95% CI: −2.3 to 5.2; p<0.001). See Tables 3 and 4, below, Other sensitivity analysis also corroborated the findings of the primary endpoint. Week 48 response rates (<50 copies per mL; FDA-snapshot analysis) were consistent across a range of patient subgroups, including age, gender, race, baseline CD4+ cell count and baseline viral load. See FIG. 4.

TABLE 3

FDA-snapshot analysis at week 48

| Outcomes, n (%) | D/C/F/TAF 800/150/200/10 mg once daily N = 362 | Control regimen N = 363 | Percentage difference (95% CI)* |
|---|---|---|---|
| Virologic success† | | | |
| Viral load <50 copies per mL | 331 (91.4%) | 321 (88.4%) | 2.7 (−1.6 to 7.1) |
| Viral load ≥50 copies per mL | 16 (4.4%) | 12 (3.3%) | |
| Last viral load in week 48 window ≥50 copies per mL | 9 (2.5%) | 9 (2.5%) | |
| Discontinued for efficacy reasons | 1 (0.3%)‡ | 0 | |
| Discontinued due to other reasons than efficacy, adverse events or death§ and last available viral load ≥50 copies per mL | 6 (1.7%) | 3 (0.8%) | |
| No viral load data in week 48 window | 15 (4.1%) | 30 (8.3%) | |
| Discontinued due to adverse event | 8 (2.2%) | 16 (4.4%) | |
| Deaths | 0 | 0 | |
| Discontinued due to other reasons¶ and last available viral load <50 copies per mL (or missing) | 4 (1.1%) | 9 (2.5%) | |
| Missing data during window but on study drug | 3 (0.8%) | 5 (1.4%) | |

CI = confidence interval;
D/C/F/TAF = darunavir/cobicistat/emtricitabine/tenofovir alafenamide;
Control regimen = darunavir/cobicistat plus emtricitabine/tenofovir disoproxil fumarate once daily.
*Calculated with the Mantel-Haenszel test adjusting for screening viral load (≤ or >100 000 copies per mL) and CD4+ count (< or ≥200 cells per mm$^3$);
†For the intent-to-treat FDA-snapshot analysis at week 48, the last available viral load value in the week 48 time-point window was used to determine response.
‡Patient reached a virologic endpoint per investigator's assessment. The patient had a viral load at Week 36 of 168 copies per mL and was withdrawn by the investigator.
The patient's last viral load on-treatment (at the early study treatment discontinuation visit 16 days post-week 36) was 31 copies per mL;
§Lost to follow-up (4 vs 2 patients), withdrawal by patient (1 vs 1) and other reasons (1 vs 0);
¶Lost to follow-up (0 vs 3), physician decision (2 vs 0), withdrawal by patient (1 vs 5), and other reasons (1 vs 1).

TABLE 4

Virologic and immunologic outcomes at week 48

| Virologic response at week 48, n (%) | D/C/F/TAF 800/150/200/10 mg once daily | Control regimen | Difference between groups (95% CI) | P value (non-inferiority) |
|---|---|---|---|---|
| Sensitivity analyses (viral load <50 copies per mL) | | | | |
| ITT (FDA Snapshot) | 331/362 (91.4%) | 321/363 (88.4%) | 2.7% (−1.6 to 7.1) | <0.0001 |
| Per protocol (FDA-snapshot) | 327/348 (94.0%) | 317/344 (92.2%) | 1.5% (−2.3 to 5.2) | <0.0001 |
| ITT (TLOVR) | 330/362 (91.2%) | 322/363 (88.7%) | 2.2% (−2.2 to 6.5) | N/A |
| ITT (observed) | 331/340 (97.4%) | 321/330 (97.3%) | −0.3% (−2.7 to 2.1) | N/A |
| FDA-snapshot analysis, n (%) | | | | |
| Viral load <20 copies per mL | 299/362 (82.6%) | 288/363 (79.3%) | 2.4% (−3.2 to 8.0) | N/A |
| Viral load <200 copies per mL | 336/362 (92.8%) | 329/363 (90.6%) | 2.2% (−1.8 to 6.2) | N/A |
| Least square means (SE) change from baseline at week 48† | | | | P value |
| Log$_{10}$ viral load, copies per mL | −2.95 (0.04) | −2.91 (0.04) | −0.05 (−0.17 to 0.07) | 0.437 |
| Absolute change in CD4+ cell count, cells per mm$^3$ | 190.49 (10.47) | 172.01 (10.46) | 18.48 (−10.59 to 47.55) | 0.213 |
| Percentage change in CD4+/lymphocytes | 7.56 (0.30) | 7.78 (0.30) | −0.23 (−1.06 to 0.61) | 0.596 |

†ANCOVA model on the change from baseline, including the baseline value and treatment as covariates. Based on non-completer = failure analysis with values after discontinuation imputed with the baseline value. Other (intermittent) missing values are imputed using last observation carried forward.
CI = confidence interval;
D/C/F/TAF = darunavir/cobicistat/emtricitabine/tenofovir alafenamide;
Control regimen = darunavir/cobicistat plus emtricitabine/tenofovir disoproxil fumarate once daily;
TLOVR = time-to-loss of virologic response Week 48 virologic response rates using the 200 and 20 copies/mL thresholds (FDA-snapshot analysis) were also similar in both groups. See Virologic and immunologic outcomes at week 48 Table 4, above. Least square mean increases (p<0.0001) from baseline in CD4+ cell count (non-completer=failure) at week 48 were 190.5 cells/mm³ in the D/C/F/TAF group and 172.0 cells/mm³ in the control group, with no statistically significant differences between groups. See Virologic and immunologic outcomes at week 48 Table 4, above.

Through week 48, 8 (D/C/F/TAF) and 6 (control) participants had protocol-defined virologic failure, with paired screening and post-baseline on-treatment genotypes available for 7 versus 2 patients. No darunavir, primary PI or TDF/TAF RAMs developed in any patient. An M184V/I mutation associated with phenotypic resistance to emtricitabine and lamivudine was identified in one patient in the CD4+/lymphocytes (%) at Week 48 were 190.5 cells/mm³ and 7.56% in the D/C/F/TAF group and 172.0 cells/mm³ and 7.78% in the control group.

Incidences of grade 3-4 adverse events (AEs) (5.2% vs 6.1%), serious AEs (4.4% vs 5.8%) (no deaths) and discontinuations due to AEs (1.9% vs 4.4%) were low. The safety profiles were similar between groups. See Table 5. Most adverse events regardless of causality were Grade 1 or 2. The most common (≥5% in either group) study drug-related adverse events through week 48 were diarrhoea, rash, and nausea. Most episodes of diarrhoea were mild in severity. Only 1 patient in each group discontinued the study due to diarrhoea. Rates of drug-related immune reconstitution inflammatory syndrome (IRIS) (and psychiatric disorders, specifically insomnia (and depression, were low in each group.

TABLE 5

Treatment-emergent adverse events and laboratory abnormalities through 48 weeks

|  | D/C/F/TAF 800/150/200/10 mg once daily N = 362 | Control regimen N = 363 |
|---|---|---|
| Any adverse event regardless of causality | 312 (86%) | 307 (85%) |
| Any study drug-related adverse event | 126 (35%) | 151 (42%) |
| Any grade 3 or 4 adverse event† regardless of causality | 19 (5%) | 22 (6%) |
| Any serious adverse event regardless of causality‡ | 17 (5%) | 21 (6%) |
| Adverse events leading to permanent discontinuation§ | 7 (2%) | 16 (4%) |
| Death 0 | 0 | 0 |
| Most common adverse events regardless of causality (≥5% of patients in either group) | | |
| Diarrhoea¶ | 71 (20%) | 66 (18%) |
| Headache | 47 (13%) | 32 (9%) |
| Nasopharyngitis | 40 (11%) | 31 (9%) |
| Rash | 32 (9%) | 25 (7%) |
| Nausea | 28 (8%) | 45 (12%) |
| Upper respiratory tract infection | 20 (6%) | 21 (6%) |
| Fatigue | 19 (5%) | 18 (5%) |
| Syphilis | 17 (5%) | 19 (5%) |
| Osteopenia | 17 (5%) | 27 (7%) |
| Bronchitis | 14 (4%) | 19 (5%) |
| Median (IQR) change in fasting lipids | | |
| Total cholesterol (mg/dL) | +28.6 (+12.8-47.2)* | +10.4 (−8.0-29.8) |
| HDL-cholesterol (mg/dL) | +4.3 (−1.2-12.0) | +1.5 (−3.9-8.1) |
| LDL-cholesterol (mg/dL) | +17.4 (+2.9-32.9)* | +5.0 (−10.8-19.0) |
| Triglycerides (mg/dL) | +23.9 (−3.0-58.5)* | +14.2 (−12.0-40.7) |
| Total cholesterol/HDL-cholesterol ratio | +0.20 (−0.28-0.67)* | +0.08 (−0.41-0.53) |

D/C/F/TAF group. This patient harboured a K103N mutation at screening, indicating transmitted NNRTI (efavirenz and nevirapine) resistance. All other patients remained sensitive to all drugs in the treatment regimen.

Through week 48, the ≥95% adherence rate as measured by pill count (all patients took three tablets once daily based on the study design) was 88.3% (264/299 patients) in the D/C/F/TAF group versus 88.3% (271/307) in the control group.

Mean increases from baseline in CD4+ cell count were 188.7 vs. 173.8 cells/mm³. In each treatment group, the mean (SE) CD4+ cell counts increased over time by 188.7 (10.57) and 173.8 (10.69) cells/mm³, respectively, at Week 48. When adjusted for baseline CD4+ count, LS mean estimates for increases from baseline in CD4+ cell count and Renal adverse events regardless of causality occurred in 2% (7/362) versus 6% (21/363) of patients. None of the renal adverse events were suggestive of treatment-emergent proximal renal tubulopathy or led to discontinuation.

Grade 3 and 4 adverse events regardless of causality, serious adverse events, and adverse event-related discontinuations were uncommon. The only grade 4 adverse event reported for ≥2 patients was suicide attempt, reported in 2 (0.6%) patients in the control group. There were no deaths during the treatment phase in both groups. However, there was one death in the control group in the follow-up phase (11 days after last study drug intake). This event was not considered related to study drug. Incidences and types of laboratory abnormalities were similar in both treatment groups being mostly Grade 1 or 2.

D/C/F/TAF provided favorable renal profile (preservation of GFR and less tubular proteinuria).

Figure 5:
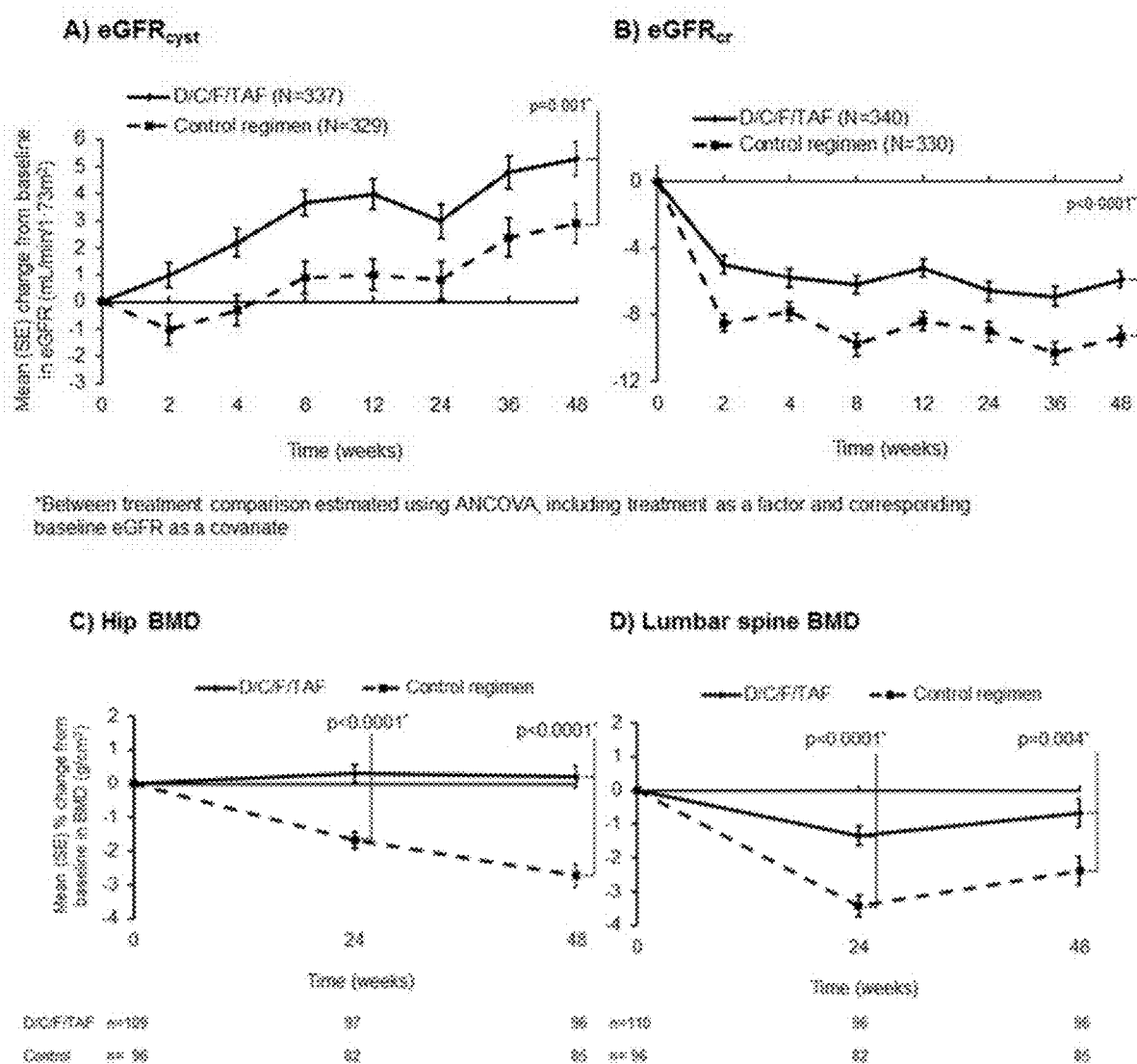
FIG. 5: Mean change from baseline to week 48 in kidney and bone parameters. Bars show SE. Mean change in (A) eGFR$_{cyst}$ and (B) eGFR$_{cr}$ was based on serum concentrations and the Kidney Disease Epidemiology Collaboration formula. BMD of the (C) hip and (D) lumbar spine was analysed with dual energy x-ray absorptiometry. BMD=bone mineral density; D/C/F/TAF=darunavir/cobicistat/emtricitabine/tenofovir alafenamide; Control regimen=darunavir/cobicistat plus emtricitabine/tenofovir disoproxil fumarate once daily; eGFR$_{cr}$=estimated glomerular filtration rate based on serum creatinine. eGFR$_{cyst}$=estimated glomerular filtration rate based on serum cystatin C.

The mean change (increase) in eGFR$_{cyst}$ (CKD-EPI formula) at Week 48 was greater for D/C/F/TAF (+5.3 mL/min/1.73 m$^2$) [SD 10.8] than control (+2.9 mL/min/1.73 m$^2$) [SD 13.3] (p<0.0001, ANCOVA for within-treatment comparisons; p=0.001 for between-treatment comparison). See FIG. 5A; see also, Table 7. Serum creatinine increased from baseline to week 48 in the D/C/F/TAF group (+4.8 μmol/L) [SD 8.7], consistent with the known effect of cobicistat on inhibition of creatinine tubular secretion, but less so than in the control group (+8.2 μmol/L) [SD 9.97] (p<0.0001, ANCOVA for within and between treatment comparisons). Consequently, the mean decrease in eGFR$_{cr}$ (CKD-EPI formula) at week 48 was less in the D/C/F/TAF group (−5.9 mL/min per 1.73 m$^2$) [SD 9.7] than in the control group (−9.3 mL/min per 1.73 m$^2$ [SD 10.9]; p<0.0001, ANCOVA for within and between treatment comparisons), (see FIG. 5B) although in both groups, mean eGFR$_{cr}$ was within normal limits.

At 48 weeks, quantitative measures of proteinuria, as determined by mean changes from baseline in ratios of total urinary protein (D/C/F/TAF −22.42 mg/g [SD 71.98] versus control −10.34 mg/g [118.18], p=0.033), albumin (−2.45 mg/g [23.81] versus −0.58 mg/g [68.93]; p=0.003), retinol binding protein (16.84 μg/g [317.31] versus 401.12 μg/g [2688.91]; p<0.0001) and β2-microglobulin (−100.58 μg/g [788.60] versus 837.63 μg/g [6122.87]; p<0.0001) to urine creatinine improved in the D/C/F/TAF group compared with the control group. See also Table 7.

D/C/F/TAF provided favorable bone safety profile vs control. See FIGS. 5C and 5D. Baseline patient characteristics in the DXA substudy were well balanced between the D/C/F/TAF (N=113) and control (N=99) groups, and comparable to those in the overall study. See Table 6.

TABLE 6

Patient baseline demographics and disease characteristics in the bone investigation substudy

| Demographics | D/C/F/TAF 800/150/200/10 mg once daily N = 113 | Control regimen N = 99 |
|---|---|---|
| Female | 11 (10%) | 7 (7%) |
| Median (range) age, years | 34 (19-60) | 33 (18-62) |
| Race | | |
| White | 95 (84%) | 86 (87%) |
| Black/African-American | 12 (11%) | 9 (9%) |
| Asian/other races | 6 (5%) | 4 (4%) |
| Ethnicity | | |
| Hispanic or Latino | 24 (21%) | 17 (17%) |
| Baseline characteristics | | |
| Median (range) log$_{10}$ viral load, copies per mL | 4.41 (3.16-6.20) | 4.45 (1.28-6.20) |
| Categorised viral load, copies per mL | | |
| <100,000 | 96 (85%) | 77 (78%) |
| ≥100,000 | 17 (15%) | 22 (22%) |
| | N = 112 | N = 99 |
| Median (range) CD4$^+$ cell count, cells per mm$^3$ | 511.5 (59-1233) | 439.0 (50-1048) |
| Categorised CD4$^+$ cell count, cells per mm$^3$ | | |
| <200 | 6 (5%) | 3 (3%) |
| ≥200 | 106 (95%) | 96 (97%) |

TABLE 6-continued

Patient baseline demographics and disease characteristics in the bone investigation substudy

| Demographics | D/C/F/TAF 800/150/200/10 mg once daily N = 113 | Control regimen N = 99 |
|---|---|---|
| Hip | N = 109 | N = 95 |
| Mean (SD) BMD (g/cm$^2$) | 0.9780 (0.11292) | 0.9567 (0.13121) |
| Mean (SD) T-score | −0.361 (0.8427) | −0.532 (0.9512) |
| | N = 107 | N = 93 |
| Mean (SD) Z-score | −0.282 (0.8686) | −0.450 (0.9110) |
| Spine | N = 110 | N = 95 |
| Mean (SD) BMD (g/cm$^2$) | 1.0156 (0.12452) | 1.0325 (0.13839) |
| Mean (SD) T-score | −0.611 (1.1653) | −0.473 (1.2832) |
| Mean (SD) Z-score | −0.616 (1.1755) | −0.481 (1.2339) |
| Femoral neck | N = 109 | N = 95 |
| Mean (SD) BNB (g/cm$^2$) | 0.8620 (0.10716) | 0.8496 (0.12808) |
| Mean (SD) T-score | −0.467 (0.8386) | −0.576 (0.9640) |
| | N = 107 | N = 93 |
| Mean (SD) Z-score | −0.218 (0.8261) | −0.323 (0.9100) |

Figure 7:
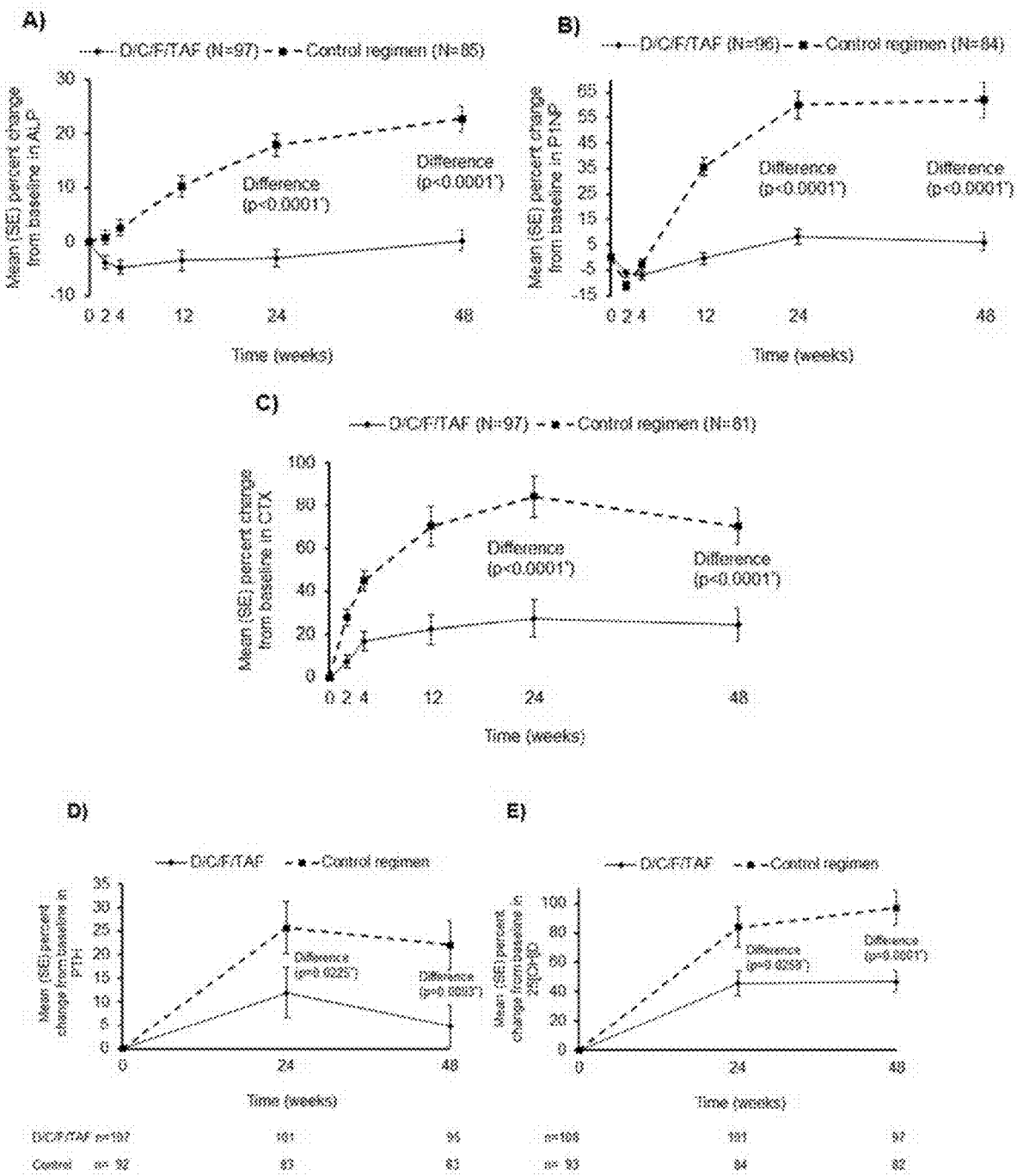
FIG. 7: Mean change from baseline at week 48 in bone biomarkers (A) alkaline phosphatase (bone formation); (B) procollagen type N-terminal propeptide (bone formation); (C) C-type collagen sequence (bone resorption); D) parathyroid hormone; E) 25-hydroxy vitamin.

Hip, lumbar spine and femoral neck BMD from baseline to week 48 were stable in the D/C/F/TAF group (mean percentage change +0.21% [SD 3.09], −0.68% [4.08] and −0.26% [4.11] at each site, respectively; p=0.589 hip, p=0.093 spine, p=0.518 femoral neck, ANCOVA for within-treatment (see FIGS. 5C and 5D) comparisons), whereas they decreased significantly at week 48 in the control group (−2.73% [3.24], −2.38% [3.75] and −2.97% [3.98], respectively; p<0.0001, ANCOVA for within-treatment comparisons at each site; p<0.0001 [hip and femoral neck] and p=0.004 [spine] for between-treatment comparisons). Fewer patients had a ≥3% decrease of hip and lumbar spine BMD in the D/C/F/TAF group than in the control group, and more patients had ≥3% increases in the D/C/F/TAF group. See FIG. 5. A similar trend was seen for the ≥3% decrease (21.9% [21/96] versus 52.9% [45/85]) and ≥3% increase (14.6% 14/96) versus 7.1% [6/85]) in femoral neck BMD and for ≥5% and ≥7% increases or decreases from baseline in BMD at the hip and spine. See FIG. 5 and Table 6. At week 48, a higher proportion of participants in the D/C/F/TAF group than in the control group had improvements in T-score from osteopenia to normal, or from osteoporosis to normal or osteopenia, at either the hip (5.2% [5/96] versus 1.2% [1/85]), lumbar spine (3.1% [3/96] versus 1.2% [1/85]) or femoral neck (2.1% [2/96] versus 2.4% [2/85]). In parallel, a lower proportion of participants in the D/C/F/TAF group had worsening BMD status at each site (hip: 3.1% [3/96] versus 14.1% [12/85]; lumbar spine: 8.3% [8/96] versus 15.3% [13/85]; femoral neck: 5.2% [5/96] versus 9.4% [8/85]). Fractures occurred infrequently and not differently in each group (1.1% [4/362] versus 0.6% [2/363]; p=0.451); all were traumatic and none were suspected to be osteoporotic. Nine of 362 patients in the D/C/F/TAF group (2.5%) and 16 of 363 patients in the control group (4.4%) not taking anti-osteoporotic drugs (including bisphosphonates, calcium or vitamin D) during the screening phase, started a new anti-osteoporotic treatment during the treatment phase. Changes from baseline in bone biomarker levels suggested less bone turnover in the D/C/F/TAF group than in the control group, with stable values for alkaline phosphatase, procollagen type N-terminal propeptide, C-type collagen sequence and parathyroid hormone in the D/C/F/TAF group, and an increase in all markers in the control group (between-treatment comparisons, p<0.0001 for alkaline phosphatase, procollagen type N-terminal propeptide, and C-type collagen sequence, and p=0.0093 for parathyroid hormone). 25-hydroxy vitamin levels increased from baseline in both groups. See FIG. 7.

Figure 6:
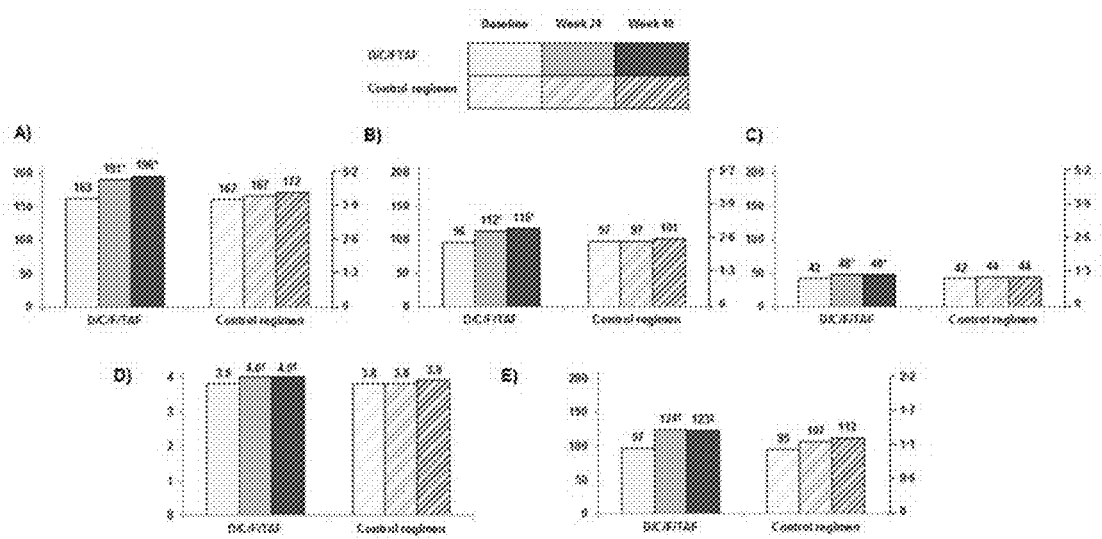
FIG. 6: Median fasting lipid levels at baseline and week 48 (A) total cholesterol; (B) low-density lipoprotein-cholesterol; (C) high-density lipoprotein-cholesterol (HDL-C); (D) total cholesterol/HDL-C ratio; (E) triglycerides.

D/C/F/TAF provided no clinically relevant changes in TC/HDL ratio (Table 7). Median changes from baseline at week 48 for fasting total cholesterol, LDL-cholesterol and triglycerides favoured control versus D/C/F/TAF and changes in HDL-cholesterol favoured D/C/F/TAF with a small, statistically significant but non-clinically relevant difference in the total cholesterol to HDL-cholesterol ratios between groups. See FIG. 6. Six (1.7%) and 2 (0.6%) patients newly started a lipid-lowering drug during the treatment period (p=0.1770 between groups).

D/C/F/TAF was non-inferior to a regimen of darunavir/cobicistat co-administered with emtricitabine/tenofovir disoproxil fumarate at week 48, with a high virologic response (91.4%) (FDA-snapshot analysis) in clinically well treatment-naïve HIV-1-infected adults. D/C/F/TAF was associated with a better bone and renal tubular safety profile than control, with few moderate, severe or serious adverse events. The fasting lipids profile favoured the control group, though with a limited number of patients newly started on a lipid-lowering drug. D/C/F/TAF combines the known efficacy and high genetic barrier to resistance of darunavir with the safety advantages of tenofovir alafenamide, in a single-tablet regimen for the treatment of ART-naïve, infected patients.

TABLE 7

Changes from baseline at Week 48 in renal and bone safety parameters

| | D/C/F/TAF N = 362 | Control N = 363 | P-value* |
|---|---|---|---|
| Mean change in eGFR$_{cyst}$, mL/min/1.73 m$^2$ | 5.3 | 2.9 | <0.0001 |
| Mean change in eGFR$_{cr}$, mL/min/1.73 m$^2$ | −5.9 | −9.3 | <0.0001 |
| Mean changes in renal biomarkers | | | |
| Urine protein: creatinine ratio (mg/g) | −22.42 | −10.34 | <0.0001 |
| Urine albumin: creatinine ratio (mg/g) | −2.45 | −0.58 | <0.0001 |
| Urine Retinol Binding Protein: creatinine ratio (μg/g) | +16.84 | +401.12 | <0.0001 |
| Urine Beta-2-Microglobulin: creatinine rat ratio (μg/g) | −100.58 | +837.63 | <0.001 |
| Lipids | | | |
| Total cholesterol (m/dL) | 28.6 | 10.4 | |
| HDL-cholesterol (mg/dL) | 4.3 | 1.5 | |
| LDL-cholesterol (mg/dL) | 17.4 | 5.0 | |
| Triglycerides (mg/dL) | 23.9 | 14.2 | |
| Median change in TC/HDL-C ratio | 0.2 | 0.08 | |

*Between treatment comparison assessed using ANCOVA (eGFR, BMD) and Wilcoxon rank-sum test (renal biomarkers);
eGFR$_{cyst}$ = eGFR cystatin C clearance (CKD-EPI formula);
eGFR$_{cr}$ = eGFR creatinine clearance (CKD-EPI formula);
BMD = bone mineral density;
ND = not determined;
TC = total cholesterol;
HDL-C = high-density lipoprotein-cholesterol Example 3

Bioequivalence of the Once-Daily Single Tablet Complete HIV-1 Regimen of Darunavir, Cobicistat, Emtricitabine and Tenofovir Alafenamide (D/C/F/TAF) Compared to Combined Intake of the Separate Agents, and the Effect of Food on Bioavailability Methods Study Populations Both studies had similar inclusion criteria which included: males or females (of non-child bearing potential, or who agreed to use a highly effective contraceptive method), aged≥18 to 55 years, with a body mass index of 18.5-30.0 kg/m$^2$, who were non-smokers for ≥3 months prior to selection, and healthy based on physical examination, medical history, vital signs, 12-lead electrocardiograms [ECGs], and clinical laboratory tests. Key exclusion criteria for both studies included: positive screening test for HIV-1, HIV-2, hepatitis A, B, and/or C; history or evidence of drug and/or alcohol abuse; significant and active diarrhea, nausea, or constipation which would affect drug absorption/bioavailability; a clinically significant disease (e.g. gastrointestinal, cardiovascular, neurologic disease) or history of renal insufficiency.

Volunteers were not allowed to take any medication≥14 days before first study drug administration, except for paracetamol (no more than 3×500 mg/day or 3 g/week) or ibuprofen (no more than 1×400 mg/day), hormone replacement therapy in post-menopausal women and hormone-based contraceptives.

Both studies were conducted according to the Declaration of Helsinki, Good Clinical Practice principles and applicable regulatory requirements. The study protocols and amendments were reviewed and approved by an Independent Ethics Committee. All volunteers provided written, informed consent prior to starting the studies.

Study Designs and Treatments

These were two Phase I, single-center, open-label, randomized, 2-sequence, 2-period crossover studies.

The bioavailability study (TMC114FD2HTX1002; Clinical Trials.gov: NCT02475135; EudraCT No. 2015-001213-27) was conducted between Jun. 1 and Aug. 14, 2015 at SGS Life Science Services Clinical Pharmacology Unit (Antwerp, Belgium). The bioavailability study comprised three separate panels, however, only the panel evaluating the impact of food on the single-dose pharmacokinetics of the D/C/F/TAF components is presented.

The bioequivalence study (TMC114FD2HTX1001; Clinical Trials.gov: NCT02578550; EudraCT No. 2015-001264-18) was conducted from Nov. 20, 2015 to Feb. 22, 2016 at CAPS Netherlands BV (Groningen, The Netherlands).

In both studies, volunteers were screened within 21 days prior to first administration of study drugs, admitted to the study site in the morning of Day 1 and fasted overnight for ≥10 hours (water was permitted up until 2 hours before dosing). Volunteers were randomized (using a computer-generated randomization schedule using permuted blocks) on Day 1 of the first treatment session, before intake of a single dose of study drug. All study drug intakes were with 240 mL of non-carbonated water and were observed within the units. The wash-out period between the two treatment sessions was ≥7 days.

To evaluate the impact of food on the bioavailability of the components of D/C/F/TAF, 24 volunteers were randomized to receive a single oral dose of D/C/F/TAF under either fasted (test) or fed (within 30 minutes after the start of a standardized high-fat breakfast) (reference) conditions. The standardized high-fat breakfast (928 kCal; 56 g fat) consisted of (or its equivalent) two eggs fried in butter, two strips of bacon, two slices of white bread with butter, one croissant with one slice of cheese, and 240 mL (8 oz) of whole milk.

In the bioequivalence study, 96 volunteers were randomized to receive a single oral dose of the D/C/F/TAF tablet (test) or a single oral dose of DRV as 1×800-mg tablet, FTC/TAF as 1×200/10-mg FDC tablet, and COBI as 1×150-mg tablet (as combined intake, reference), under fed conditions (within 5 minutes after completing a standardized regular breakfast). The standardized regular breakfast (533 kCal; 21 g fat) consisted of (or its equivalent) four slices of bread, two slices of ham and/or cheese, butter, fruit preserve, and two cups (up to 480 mL) of decaffeinated coffee or tea with milk and/or sugar.

Water and food were permitted from 2 and 4 hours, respectively, after taking the study drugs.

Sample Sizes

Impact of Food on the Bioavailability of the Components of D/C/F/TAF

From previous bioavailability studies, intra-subject variability (log-transformed) was estimated to be a maximum of 0.36, which is the highest variability across exposures and maximum plasma concentrations ($C_{max}$) for the different components of D/C/F/TAF. Based on this intra-subject variability of 0.36, and a target sample size of 22 volunteers completing the food-effect study, the precision range, expressed as the percentage of the true value, for the geometric mean ratio (GMR) (test over reference) of the primary pharmacokinetic parameters was expected to be within the 83% and 120% bounds with 90% confidence. An additional two volunteers were recruited to account for premature discontinuations, making the total sample size 24 participants.

Bioequivalence Study

The $C_{max}$ of TAF was found to be the most variable pharmacokinetic parameter among those for the components of D/C/F/TAF. As such, a within-subject log standard deviation of 0.456, corresponding to a coefficient of variation (CV %) of 48%, was used for the sample size calculation. Based on a within-subject log standard deviation of 0.456 and using a 2 one-sided t-tests procedure at a significance level of 5% each, the total number of volunteers needed to demonstrate bioequivalence between the D/C/F/TAF fixed-dose combination (FDC) and combined administration of DRV, an FTC/TAF FDC and COBI administered as separate agents, with an overall 80% power when the true difference between treatments is 5%, was 91 participants. Recruitment of 96 volunteers was planned to account for premature discontinuations.

Given the uncertainty around the variability for the TAF $C_{max}$, a blinded (for treatment) sample size re-estimation (Golkowski, et al. 2014) was performed by an independent party after all volunteers had been dosed, to re-evaluate the sample size and power based on the actual variability of TAF $C_{max}$; however, no additional volunteers were recruited.

Pharmacokinetic Assessments

In the food effect bioavailability study, full pharmacokinetic profiles for DRV, COBI, FTC and TAF were determined over 72, 72, 48 and 12 hours, respectively after administration in each treatment session. In the bioequivalence study, full pharmacokinetic profiles for these drugs were determined over 72, 72, 72 and 8 hours, respectively.

Validated, specific and sensitive high-performance liquid chromatography-tandem mass spectroscopy (LC-MS/MS) assays were used to determine plasma concentrations of DRV, COBI, FTC and TAF (Blum et al, 2007) with lower limits of quantification (LLOQ) of 5.0 ng/mL for FTC, DRV and COBI, and 1.0 ng/mL for TAF. DRV and COBI were measured with a combined method, in which protein precipitation with acetonitrile was done on 50 µl of plasma, with separation on an XBridge C18 column (4.6×30 mm, 3.5 µm), and detection was performed with an ABSciex Triple Quad 5500 LC-MS/MS system (Applied Biosystems, Foster City, Calif., USA).

Safety and Tolerability Assessments

Safety and tolerability assessments included evaluation of adverse events (AEs), clinical laboratory parameters (serum chemistry, hematology, urinalysis), vital signs, ECGs, physical examination, and follow-up on specific toxicities including rash, acute systemic allergic reactions, aspartate aminotransferase (AST)/alanine aminotransferase (ALT) elevations, clinical hepatitis, renal complications, nausea and diarrhea. Adverse events and concomitant medications were monitored throughout the studies. In the food effect bioavailability study, ECGs, vital signs, serum chemistry and hematology (10 hours after fasting), and urinalysis were assessed at screening, on Day 1 (within 2 hours before intake of study drug), and on Day 4. In the bioequivalence study, ECG was only measured at screening, and vital signs were measured at screening, on Day 1 (within 2 hours before intake of study drug) and Day 4. Clinical laboratory assessments were made at screening and on Day −1 or 1, Days 2 and 4. The follow-up period was 7 to 10 days after the last intake of study medication or after study discontinuation. The severity of AEs and laboratory abnormalities were evaluated using the DAIDS grading table (NIAID, 2014). AEs were coded according to the Medical Dictionary for Regulatory Activities Version 18.0 (food effect bioavailability study) or Version 18.1 (bioequivalence study).

Data Analyses

For both studies, the following key pharmacokinetic parameters for each of the component drugs were determined using non-compartmental analysis (WinNonlin version 6.2.1, Pharsight Corporation, Mountain View, Calif., USA): $C_{max}$; time to $C_{max}$ ($t_{max}$); area under the plasma concentration-time profile (AUC, calculated by linear-linear trapezoidal summation) from time of administration up to the last timepoint with a measurable concentration post-dose ($AUC_{last}$) and extrapolated to infinity ($AUC_{inf}$ calculated as $AUC_{last}$ plus $C_{last}/\lambda_z$ where $C_{last}$ is the last time post dose with a quantifiable concentration and $\lambda_z$ is the apparent terminal elimination rate constant); and the terminal elimination half-life ($t_{1/2term}$ calculated as $0.693/\lambda_z$).

The least square (LS) means of natural logarithm-transformed $C_{max}$, $AUC_{last}$ and $AUC_{inf}$ for each component of D/C/F/TAF were estimated using a linear mixed-effects model, controlling for treatment, sequence, and period as fixed effects, and subject as a random effect (SAS version 9.3, SAS Institute, Cary, N.C., USA).

In the food effect bioavailability study, a 90% confidence interval (CI) was constructed around the difference between the LS-means of test and reference, back-transformed using the exponential function, and compared with the 80% to 125% boundaries of no effect. In the bioequivalence study, an adjusted CI of 90.14% (as opposed to a 90.00% CI) was constructed around the difference between the LS-means of test and reference and re-transformed to the original scale. The adjusted CI was a result of a blinded (for treatment) sample size re-estimation (given the uncertainty of the TAF $C_{max}$ variability), in order to control the nominal type I error rate. Bioequivalence of the D/C/F/TAF tablet compared to combined intake of the separate agents was met if the 90.14% CIs for $C_{max}$, $AUC_{last}$ and $AUC_{inf}$ for DRV, FTC and TAF were within the predefined limits of 80% to 125%.

Results

Participant Disposition and Baseline Characteristics

In the food-effect bioavailability study, 24 participants were randomized, of whom all completed the study. For the bioequivalence study, 96 volunteers were randomized. Two volunteers withdrew consent, but completed the safety follow-up visit and were considered as having completed the study. All 24 volunteers in the food-effect bioavailability study and all 96 volunteers in the bioequivalence study were included in the pharmacokinetic and safety analyses for the respective study.

In both studies, there was an even distribution of women and men; the majority of volunteers were white and not Hispanic or Latino (Table 8). Demographic data and baseline characteristics were comparable across treatment sequences (data not shown).

TABLE 8

| Demographics and baseline characteristics | | |
|---|---|---|
| Characteristic | Food-effect bioavailability study N = 24 | Bioequivalence study N = 96 |
| Sex, n, (%) | | |
| Men | 12 (50) | 52 (54) |
| Women | 12 (50) | 44 (46) |
| Age, years, median (range) | 35.0 (18-54) | 26.0 (18-55) |

TABLE 8-continued

| Demographics and baseline characteristics | | |
|---|---|---|
| Characteristic | Food-effect bioavailability study N = 24 | Bioequivalence study N = 96 |
| Body mass index, kg/m², median (range) | 23.65 (19.8-29.5) | 23.5 (18.8-29.8) |
| Race, n (%) | | |
| White | 24 (100) | 83 (87) |
| Black/African American | 0 | 9 (9) |
| Asian | 0 | 4 (4) |
| Unknown | 0 | 0 |
| Ethnicity | | |
| Hispanic or Latino | 1 (4) | 5 (5) |
| Not Hispanic or Latino | 23 (96) | 91 (95) |
| Not reported/unknown | 0 | 0 |

Effect of Flood on the Bioavailability of the Components of D/C/F/TAF

Results of the food-effect bioavailability study showed that when D/C/F/TAF was administered under fasted conditions (test), DRV $C_{max}$, $AUC_{last}$ and $AUC_{inf}$ were 45%, 34% and 30% lower, respectively, compared with fed conditions (standardized high-fat breakfast; reference) (Table 9). Also, mean maximum DRV concentrations were reached earlier in fasted compared with fed conditions (FIG. 1A).

TABLE 9

Food-effect bioavailability study: Pharmacokinetic parameters and statistical analysis of DRV, COBI, FTC and TAF following administration of a single oral dose of D/C/F/TAF 800/150/200/10 mg under fed (standardized high-fat breakfast) and fasted conditions.

| Parameter, mean (SD)[a] | DRV | | COBI | | FTC | | TAF | |
|---|---|---|---|---|---|---|---|---|
| | Fasted (test) N = 23[b] | Fed (high fat) (reference) N = 24[b] | Fasted (test) N = 23[c] | Fed (high fat) (reference) N = 24 | Fasted (test) N = 24[d] | Fed (high fat) (reference) N = 24[e] | Fasted (test) N = 24[f] | Fed (high fat) (reference) N = 24[d] |
| $C_{max}$, ng/mL | 4089 (1846) | 6629 (1543) | 704 (368) | 711 (164) | 2247 (573) | 1785 (486) | 180 (90.6) | 107 (65.2) |
| $t_{max}$, hours | 3.00 (1.00-8.02) | 5.00 (1.50-8.00) | 3.00 (1.00-6.00) | 5.00 (2.00-6.10) | 1.00 (0.50-2.00) | 2.00 (0.75-5.00) | 0.50 (0.25-0.75) | 0.88 (0.25-5.00) |
| $AUC_{last}$, ng · h/mL | 67504 (35642) | 93541 (39730) | 5771 (3206) | 6168 (2260) | 11593 (2573) | 11499 (2055) | 106 (44.7) | 117 (51.5) |
| $AUC_{inf}$, ng · h/mL | 72147 (36009) | 94686 (40882) | 6136 (3064) | 6258 (2268) | 12286 (2729) | 10029 (1079)[g] | 109 (47.7) | 125 (57.3) |
| $t_{1/2term}$, hours | 7.0 (2.3) | 7.8 (3.5) | 4.1 (0.9) | 3.9 (0.6) | 10.8 (1.2) | 10.7 (1.2)[g] | 0.3 (0.2) | 0.5 (0.1) |
| Geometric mean ratio, % (90% CI) | | | | | | | | |
| N[h] | 23 vs 24 | | 23 vs 24 | | 24 vs 24 | | 24 vs 24 | |
| $C_{max}$ | 54.99 (46.73-64.71) | | 76.96 (55.70-106.33) | | 125.99 (112.85-140.65) | | 182.29 (140.50-236.50) | |

TABLE 9-continued

Food-effect bioavailability study: Pharmacokinetic parameters and statistical analysis of DRV, COBI, FTC and TAF following administration of a single oral dose of D/C/F/TAF 800/150/200/10 mg under fed (standardized high-fat breakfast) and fasted conditions.

| Parameter, mean (SD)[a] | DRV | | COBI | | FTC | | TAF | |
|---|---|---|---|---|---|---|---|---|
| | Fasted (test) N = 23[b] | Fed (high fat) (reference) N = 24[b] | Fasted (test) N = 23[c] | Fed (high fat) (reference) N = 24 | Fasted (test) N = 24[d] | Fed (high fat) (reference) N = 24[e] | Fasted (test) N = 24[f] | Fed (high fat) (reference) N = 24[d] |
| $AUC_{last}$ | 65.65 (56.76-75.92) | | 70.90 (51.13-98.30) | | 100.12 (96.29-104.10) | | 89.54 (81.20-98.72) | |
| $AUC_{inf}$ | 70.25[j] (59.49-82.95) | | 84.39[k] (68.52-103.95) | | — | | 80.38[l] (73.04-88.45) | |

Figure 1B:
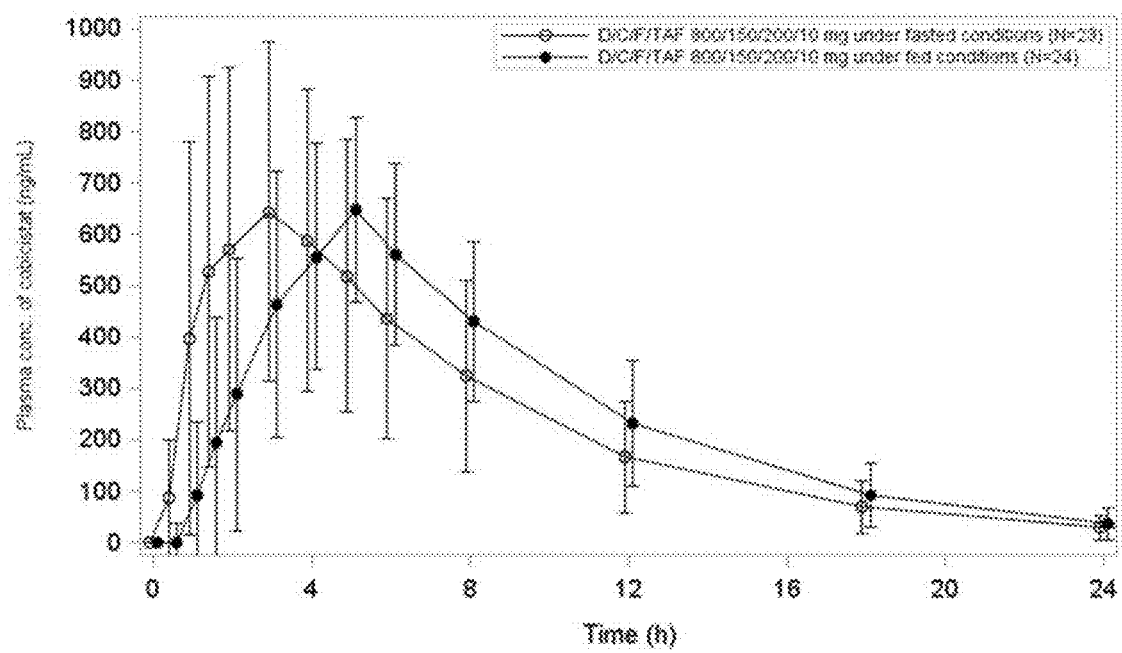
FIG. 1B. Food-effect bioavailability study: Mean (standard deviation) plasma concentration-time profiles for cobicistat (C or COBI) following administration of a single oral dose of D/C/F/TAF 800/150/200/10 mg under fed (standardized high-fat breakfast) and fasted conditions.

[a]Except $t_{max}$ = median (range);
[b]n = 20,
[c]n = 22,
[d]n = 16,
[e]n = 7,
[f]n = 21 for $AUC_{inf}$, $t_{1/2term}$;
[g]Accurate determination not possible for more than 50% of participants; interpret with caution;
[h]test vs reference;
[j]n = 20 for test and reference;
[k]n = 22 for test;
[l]n = 21 for test and n = 16 for reference;
SD = standard deviation;
CI = confidence interval;
$C_{max}$ = maximum plasma concentration;
$t_{max}$ = time to $C_{max}$;
$AUC_{last}$ = area under the plasma concentration-time profile from time of administration up to the last timepoint with a measurable concentration post-dose; $AUC_{inf}$ = AUC from time of administration to infinity;
$t_{1/2term}$ = terminal elimination half-life The COBI $C_{max}$, $AUC_{last}$ and $AUC_{inf}$ were, respectively, 23%, 29% and 16% lower, in fasted compared with fed conditions (Table 9). Also, mean maximum COBI concentrations were reached earlier in fasted conditions than in fed conditions (FIG. 1B).

Figure 1C:
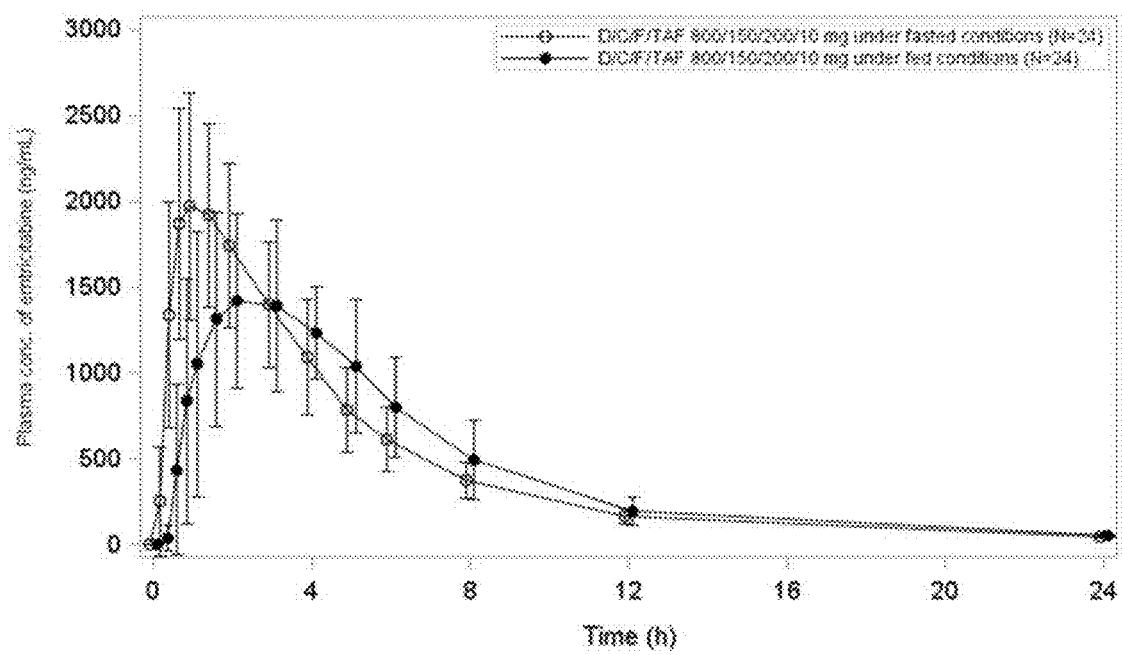
FIG. 1C. Food-effect bioavailability study: Mean (standard deviation) plasma concentration-time profiles for emtricitabine (F or FTC) following administration of a single oral dose of D/C/F/TAF 800/150/200/10 mg under fed (standardized high-fat breakfast) and fasted conditions.

For FTC, $C_{max}$ was 26% higher in fasted compared with fed conditions, while $AUC_{last}$ was comparable under both conditions (90% CI of the GMR within the 80% to 125% interval) (Table 9). Also, the mean maximum FTC concentrations (FIG. 1C) were reached earlier in fasted compared with fed conditions.

Figure 1D:
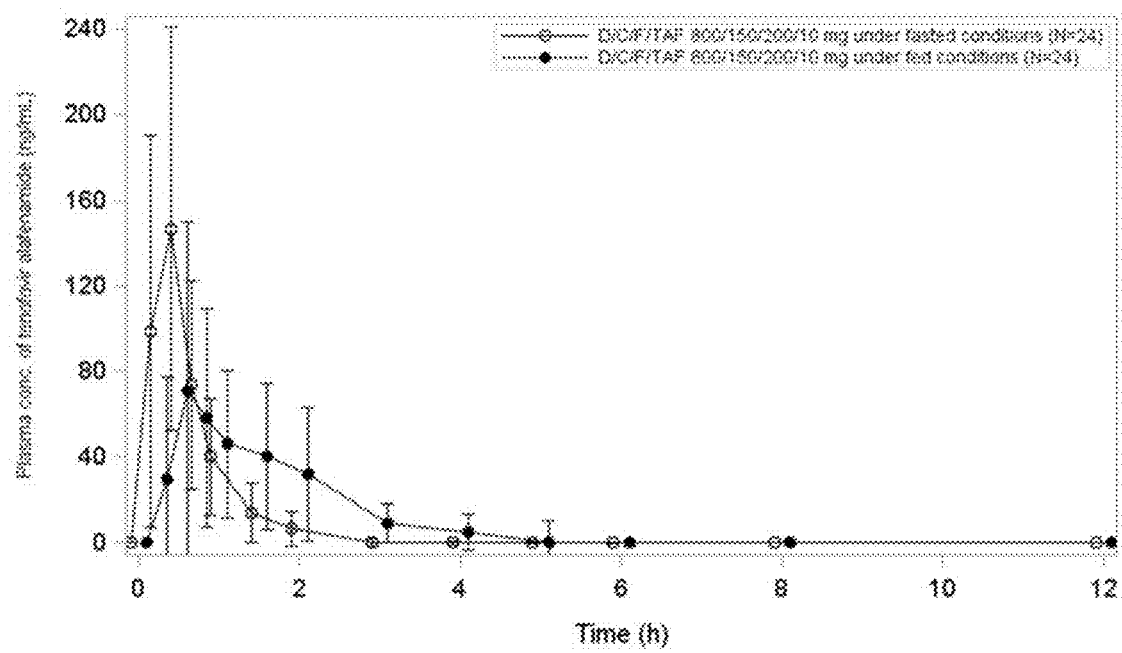
FIG. 1D. Food-effect bioavailability study: Mean (standard deviation) plasma concentration-time profiles for tenofovir alafenamide (TAF) following administration of a single oral dose of D/C/F/TAF 800/150/200/10 mg under fed (standardized high-fat breakfast) and fasted conditions.
Figure 2A:
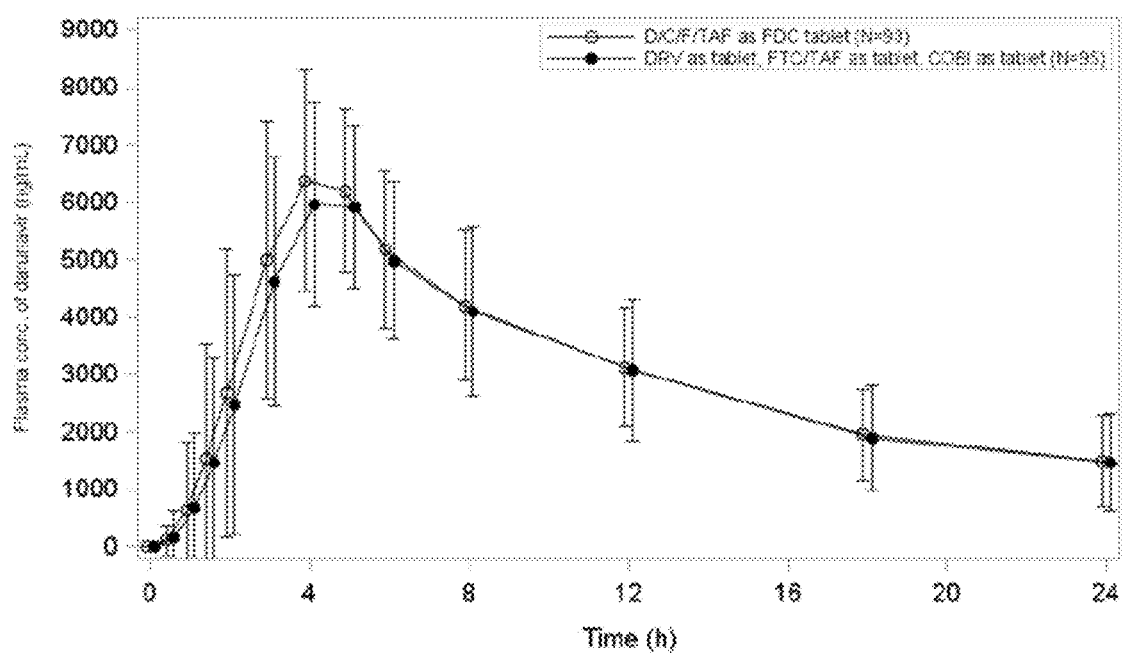
FIG. 2A. Bioequivalence study: Mean (standard deviation) plasma concentration-time profiles for DRV following administration of a single oral fixed dose combination (FDC) of D/C/F/TAF 800/150/200/10 mg or oral doses of the separate agents DRV 800 mg, FTC/TAF 200/10 mg FDC and COBI 150 mg as separate tablets, under fed conditions (standardized regular breakfast).
Figure 2B:
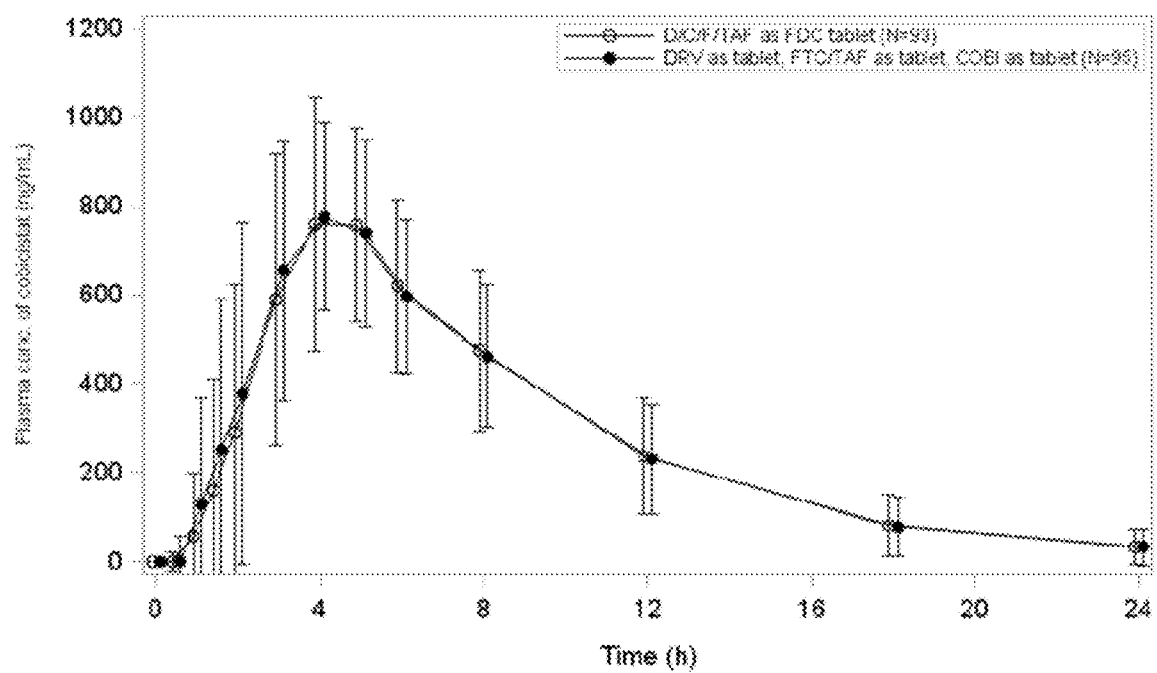
FIG. 2B. Bioequivalence study: Mean (standard deviation) plasma concentration-time profiles for COBI following administration of a single oral FDC of D/C/F/TAF 800/150/200/10 mg or oral doses of the separate agents DRV 800 mg, FTC/TAF 200/10 mg FDC and COBI 150 mg as separate tablets, under fed conditions (standardized regular breakfast).
Figure 2C:
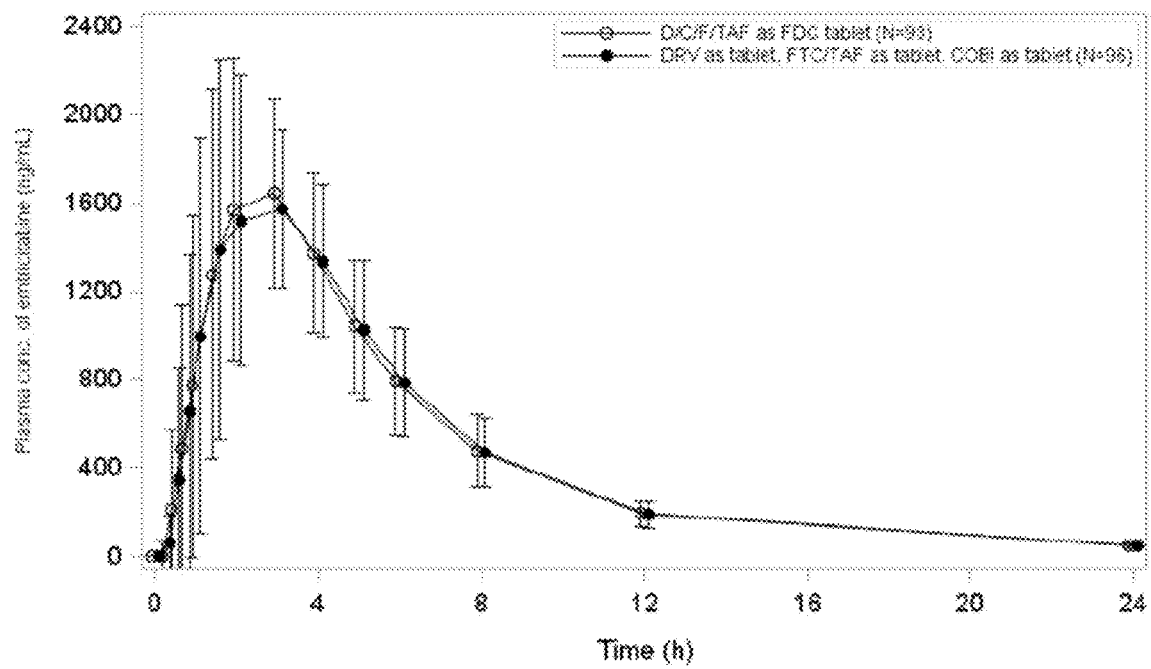
FIG. 2C. Bioequivalence study: Mean (standard deviation) plasma concentration-time profiles for FTC following administration of a single oral FDC of D/C/F/TAF 800/150/200/10 mg or oral doses of the separate agents DRV 800 mg, FTC/TAF 200/10 mg FDC and COBI 150 mg as separate tablets, under fed conditions (standardized regular breakfast).
Figure 2D:
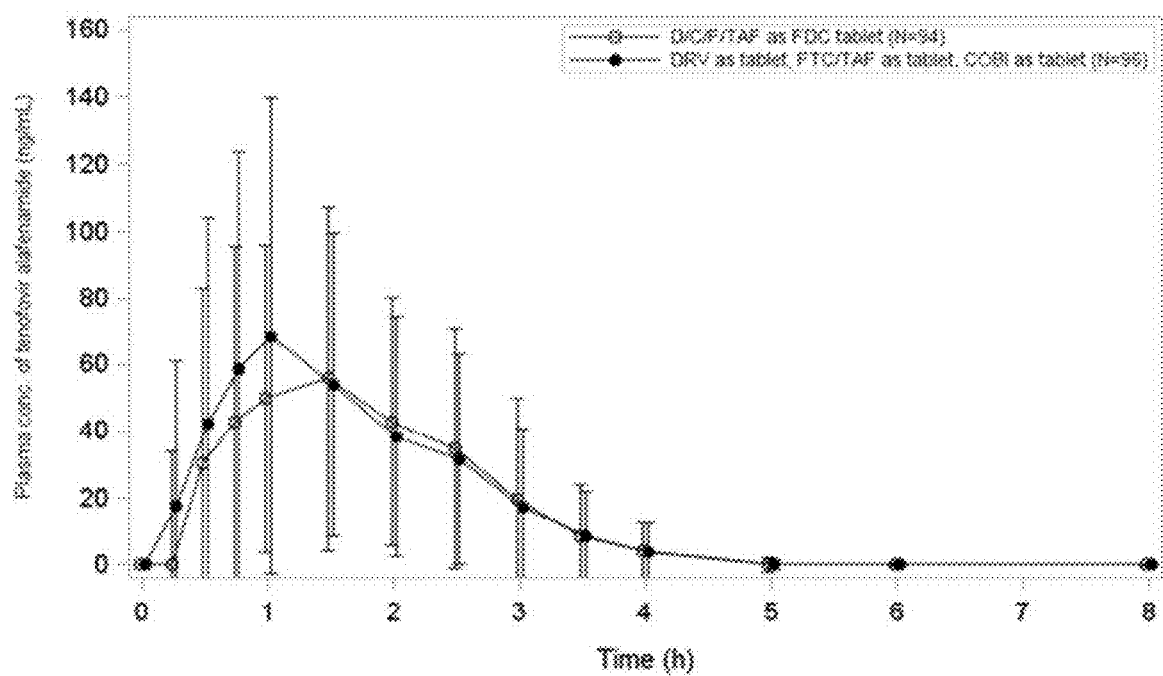
FIG. 2D. Bioequivalence study: Mean (standard deviation) plasma concentration-time profiles for TAF following administration of a single oral FDC of D/C/F/TAF 800/150/200/10 mg or oral doses of the separate agents DRV 800 mg, FTC/TAF 200/10 mg FDC and COBI 150 mg as separate tablets, under fed conditions (standardized regular breakfast).

For TAF, the $C_{max}$ was 82% higher, while $AUC_{inf}$ was 20% lower, in fasted than in fed conditions. The TAF $AUC_{last}$ was comparable under both conditions (90% CI of the GMR within the 80% to 125% boundaries of no effect) (Table 9). Also, the mean maximum TAF concentrations (FIG. 1D) were reached earlier in fasted compared with fed conditions.

TABLE 10

Bioequivalence study: Pharmacokinetic parameters and statistical analysis of DRV, COBI, FTC and TAF following administration of a single oral dose of D/C/F/TAF 800/150/200/10 mg or a single oral dose of the separate agents DRV 800 mg, FTC/TAF 200/10 mg FDC and COBI 150 mg, under fed conditions (standardized regular breakfast).

| Parameter, mean (SD)[a] | D/C/F/TAF (800/150/200/ 10 mg) (test) N = 94 | Separate agents DRV 800 mg, FTC/TAF 200/10 mg FDC, and COBI 150 mg (reference) N = 96 | Geometric mean ratio (90.14% CI)[b], % |
|---|---|---|---|
| DRV | | | |
| $C_{max}$, ng/mL | 7042 (1481)[c] | 6620 (1429)[c] | 106.73 (103.50-110.06)[c] |
| $t_{max}$, hours | 4.00 (1.50-8.00)[c] | 4.00 (2.00-12.00)[c] | — |
| $AUC_{last}$, ng·h/mL | 87200 (27385)[c] | 84406 (29481)[c] | 104.84 (100.87-108.97)[c] |
| $AUC_{inf}$, ng·h/mL | 87280 (28097)[d] | 85210 (29561)[d] | 103.74 (99.62-108.02)[d] |
| $t_{1/2term}$, hours | 5.9 (2.1)[d] | 6.2 (2.7)[d] | — |
| COBI | | | |
| $C_{max}$, ng/mL | 894 (254)[c] | 881 (207)[c] | 100.69 (96.80-104.73)[c] |
| $t_{max}$, hours | 4.00 (1.50-6.00)[c] | 4.00 (1.50-5.05)[c] | — |
| $AUC_{last}$, ng·h/mL | 6681 (2486)[c] | 6763 (2436)[c] | 98.77 (95.14-102.52)[c] |
| $AUC_{inf}$, ng·h/mL | 6785 (2518)[c] | 6868 (2459)[c] | 98.76 (95.15-102.52)[c] |
| $t_{1/2term}$, hours | 3.7 (0.7)[c] | 3.7 (0.7)[c] | — |
| FTC | | | |
| $C_{max}$, ng/mL | 2041 (481)[e] | 2053 (469)[e] | 99.32 (95.61-103.17)[e] |
| $t_{max}$, hours | 2.00 (0.60-5.00)[e] | 2.00 (0.50-5.00)[e] | — |
| $AUC_{last}$, ng·h/mL | 11722 (1959)[e] | 11746 (1868)[e] | 100.04 (98.46-101.66)[e] |

TABLE 10-continued

Bioequivalence study: Pharmacokinetic parameters and statistical analysis of DRV, COBI, FTC and TAF following administration of a single oral dose of D/C/F/TAF 800/150/200/10 mg or a single oral dose of the separate agents DRV 800 mg, FTC/TAF 200/10 mg FDC and COBI 150 mg, under fed conditions (standardized regular breakfast).

| Parameter, mean (SD)$^a$ | D/C/F/TAF (800/150/200/ 10 mg) (test) N = 94 | Separate agents DRV 800 mg, FTC/TAF 200/10 mg FDC, and COBI 150 mg (reference) N = 96 | Geometric mean ratio (90.14% CI)$^b$, % |
|---|---|---|---|
| $AUC_{inf}$, ng · h/mL | 11882 (2002)$^f$ | 11927 (1935)$^f$ | 100.13 (98.36-101.9:)$^f$ |
| $t_{1/2term}$, hours | 16.5 (3.3)$^f$ | 17.0 (3.4)$^f$ | — |
| TAF | | | |
| $C_{max}$, ng/mL | 110 (54.1) | 120 (74.0) | 96.87 (88.95-105.50) |
| $t_{max}$, hours | 1.50 (0.25-3.50) | 1.01 (0.25-4.00) | — |
| $AUC_{last}$, ng · h/mL | 123 (42.0) | 132 (58.1) | 96.59 (91.72-101.73) |
| $AUC_{inf}$, ng · h/mL | 127 (39.4)$^g$ | 141 (59.7)$^g$ | 95.42 (90.62-100.48)$^g$ |
| $t_{1/2term}$, hours | 0.3 (0.1)$^g$ | 0.3 (0.1)$^g$ | — |

$^a$Except $t_{max}$ = median (range);
$^b$As a result of a blinded (for treatment) sample size re-estimation, to control the nominal type I error rate, an adjusted 90.14% CI was calculated as opposed to the traditional 90.00% CI; no additional participants were recruited beyond the originally planned number
$^c$n = 93 test, n = 95 reference;
$^d$n = 87 test, n = 91 reference;
$^e$n = 93 test, n = 96 reference;
$^f$n = 85 test, n = 87 reference;
$^g$n = 79 test, n = 78 reference
SD = standard deviation;
CI = confidence interval;
$C_{max}$ = maximum plasma concentration;
$t_{max}$ = time to $C_{max}$;
$AUC_{last}$ = area under the plasma concentration-time profile from time of administration up to the last timepoint with a measurable concentration post-dose;
$AUC_{inf}$ = AUC from time of administration to infinity;
$T_{1/2term}$ = terminal elimination half-life Bioequivalence Study DRV, COBI, FTC and TAF plasma concentration-time profiles (FIGS. 2A to 2D) were similar for D/C/F/TAF (test) and combined administration of the separate agents (reference), under fed conditions (standardized regular breakfast). The 90.14% CIs of the GMRs of all main pharmacokinetic parameters were within the bioequivalence range of 80% to 125% for all four components (DRV, COBI, FTC and TAF) (Table 10; FIGS. 2A-2D).

Safety and Tolerability

For both studies, administration of D/C/F/TAF was generally well tolerated. The most frequently reported AEs were headache and nausea (Table 11). The incidence of these AEs was generally comparable in each treatment group for each study (Table 11). No new safety issues, grade 3 or 4 or serious AEs or deaths occurred. There were no discontinuations due to AEs. There were no clinically-relevant or consistent changes in laboratory parameters (clinical chemistry, hematology, or urinalysis). Most treatment-emergent laboratory abnormalities were grade 1 in severity and not reported as AEs. There were no relevant or clinically significant changes in ECG parameters, vital signs, or physical examination. The most frequently observed vital signs abnormality was a low supine pulse.

TABLE 11

Summary of safety and tolerability

| | Food-effect bioavailability study | | Bioequivalence study | | |
|---|---|---|---|---|---|
| | D/C/F/TAF (fasted) N = 24 | D/C/F/TAF (fed) N = 24 | D/C/F/TAF (fed) N = 94 | DRV, FTC/TAF, COBI (fed) N = 96 | Overall |
| AE, n (%) | | | | | |
| Any AE | 9 (37.5) | 10 (42) | 52 (55) | 46 (48) | 66 (69) |
| Most common AEs | | | | | |
| GI disorders | 5 (21) | 4 (17) | 27 (29) | 21 (22) | 32 (33) |
| Nausea | 4 (17) | 2 (8) | 17 (18) | 14 (15) | 21 (22) |

TABLE 11-continued

Summary of safety and tolerability

|  | Food-effect bioavailability study | | Bioequivalence study | | |
| --- | --- | --- | --- | --- | --- |
|  | | | | DRV, | |
|  | D/C/F/TAF (fasted) N = 24 | D/C/F/TAF (fed) N = 24 | D/C/F/TAF (fed) N = 94 | FTC/TAF, COBI (fed) N = 96 | Overall |
| Nervous system disorders | 4 (17) | 5 (21) | 20 (21) | 23 (24) | 36 (37.5) |
| Headache | 3 (12.5) | 5 (21) | 14 (15) | 15 (16) | 25 (26) |

Food-Effect Bioavailability Study

Grade 2 AEs were reported by three volunteers. Grade 2 irritable bowel syndrome occurred following D/C/F/TAF under fasted conditions, and was considered not related to the study medication by the investigator. Grade 2 nausea and headache reported following D/C/F/TAF with a standardized high-fat breakfast were considered possibly and doubtfully related, respectively, to the study medication. A Grade 3 treatment-emergent increase in low-density lipoprotein cholesterol occurred in one volunteer, which was transient and was not reported as AE.

Overall, 6 volunteers (25%) in fasted conditions and 5 volunteers (21% in fed conditions experienced at least one AE that was considered by the investigator to be at least possibly related to D/C/F/TAF, including nausea, erythema, vomiting, diarrhea and pruritus.

Bioequivalence Study

All reported AEs were grade 1 in severity. One grade 3, isolated, transient, treatment-emergent increase in lipase (195 U/L) was observed on Day 4 following treatment with the separate agents (DRV plus COBI plus FTC/TAF), but this was not considered clinically significant by the investigator. Lipase levels for this participant were within normal ranges at baseline (29 U/L), and at all assessments before Day 4 of treatment with the separate agents (range: 27-41 U/L), as well as at follow-up after 7-10 days (31 U/L). Concurrent transient grade 2 increases in total amylase (156 U/L) and pancreatic amylase (113 U/L) also occurred on Day 4 following treatment with the separate agents, but were within normal ranges at all other time points during the study. No AEs related to this laboratory abnormality were reported for this volunteer. The levels of ALT and AST were within normal ranges at all time points during the study.

Overall, 28 volunteers (30%) experienced at least one AE that was considered to be possibly related to D/C/F/TAF by the investigator, most frequently nausea, headache, vomiting, abdominal pain, dizziness, somnolence and diarrhea.

Discussion

The data demonstrated the bioequivalence of the D/C/F/TAF tablet to combined administration of the separate agents DRV, the FTC/TAF FDC, and COBI. The relative bioavailability study demonstrated that a food effect was observed for DRV absorption following administration of the D/C/F/TAF 800/150/200/10-mg complete HIV-1 regimen, similar to other DRV-containing regimens.

Results from the food-effect bioavailability study showed that the $C_{max}$, $AUC_{last}$ and $AUC_{inf}$ for DRV decreased under fasted conditions compared with fed conditions. This observation is consistent with the findings of previous food-effect studies for DRV. In a study of DRV co-administered with ritonavir, a 32% decrease in DRV $AUC_{last}$ was seen in fasted versus fed conditions (Sekar et al. 2007). In another study, for DRV boosted with COBI, a 39% to 56% decrease in DRV pharmacokinetic parameters was seen in fasted versus fed conditions (Kakuda et al, 2014). The food effect for DRV has been previously shown to be similar for different types of food (PREZISTA® prescribing information). Consistent with prescribing recommendations for other DRV formulations (PREZISTA® prescribing information), it is recommended that D/C/F/TAF be taken with food.

While the exposure ($AUC_{inf}$, $AUC_{last}$) to COBI administered as D/C/F/TAF was 16 to 29% lower in fasted conditions compared with fed conditions, this observation is not considered to be clinically relevant. A previous study has shown that food had no significant effect on COBI pharmacokinetics (Kakuda et al, 2014), and the administration of COBI with food is driven by the recommendations for the drug of which the pharmacokinetics it is boosting. As expected, the FTC exposure ($AUC_{last}$) was unaffected by food. For TAF, the $AUC_{inf}$ was 20% lower and the $AUC_{inf}$ was comparable in fasted compared to in fed conditions. Differences in exposure to FTC and TAF in fasted versus fed conditions are also not considered to be clinically relevant. The TAF results in the current food-effect bioavailability study are also consistent with a previous study (GS-US-292-0110), which assessed the pharmacokinetics of TAF after dosing of the complete HIV-1 regimen elvitegravir 150 mg, COBI 150 mg, FTC 200 mg and TAT 10 mg (ECFTAF) under fasted and fed conditions, and showed there was a minimal effect of food on TAF exposure Furthermore, the prescribing information for the F/TAF FDC (DESCOVY PI) states that it can be taken with or without food. The combined assessment for the D/C/F/TAF components is driven by the impact of food on the DRV pharmacokinetics.

TAF is a tenofovir prodrug that provides higher intracellular levels of the active moiety tenofovir-diphosphate (TFV-DP) in key target cells such as lymphocytes and macrophages and lower plasma tenofovir levels relative to TDF and at a much lower dose (Lee, et al. 2005; Birkus, et al. 2007; Birkus, et al. 2008), thereby maximizing antiviral potency and improving renal and bone safety (Ruane et al, 2013; Mills, et al. 2015; Sax, et al. 2014). An intensive PK analysis in a subset of 32 participants from an exploratory Phase II trial of 153 treatment-naïve, HIV-1-infected adults showed the mean plasma exposure ($AUC_{last}$) for TAF was 130.5 ng·h/mL, with a median plasma half-life of 0.45 hours (Mills, et al. 2015). These values are consistent with those seen in the food-effect bioavailability study under fed conditions (117 ng·h/mL and 0.5 hours, respectively). Plasma tenofovir levels were not measured in the current food-effect study, but participants in the TAF group of the Phase II study had a greater than 90% lower mean systemic tenofovir exposure than those in the TDF group (339 versus 3737 ng·h/mL, respectively).

Given the increase in DRV exposure when administered with food, and the recommended intake for DRV regimens in fed conditions, the bioequivalence study was conducted under fed conditions. Systemic exposure to all four components of D/C/F/TAF (DRV, COBI, FTC, TAF), as indicated by $C_{max}$, $AUC_{last}$ and $AUC_{inf}$ were comparable following administration of the D/C/F/TAF or combined administration of the separate agents DRV, the FTC/TAF FDC, and COBI. Indeed, the 90.14% CIs of the GMRs for these pharmacokinetic parameters were within the 80.00-125.00% bioequivalence limits. This finding is noteworthy because a single-tablet D/C/F/TAF 800/150/200/10-mg complete HIV-1 regimen would reduce the pill burden for HIV-1 infected patients, and such single-tablet regimens have previously been shown to improve treatment adherence and virologic outcomes compared with multi-tablet regimens (Dejesus, et al. 2009; Hodder, et al. 2010; Willig, et al. 2008; Clay, et al. 2015).

Even though these studies only investigated a single dose of D/C/F/TAF, both studies also showed that administration of D/C/F/TAF was generally well tolerated under both fed and fasted conditions. No new safety issues were identified, and no Grade 3/4 or serious AEs, deaths or discontinuations due to AEs occurred. The tolerability profile is consistent with earlier studies, with the most commonly reported AEs during the studies, headache and nausea, reported previously for studies of DRV, COBI, FTC and TAF (Cahn, et al, 2011; Ortiz, et al. 2008; Mills, et al. 2009; Orkin, et al. 2013; Flynn, et al. 2014; Tashima, et al. 2014; Mills, et al. 2015).

The once-daily, single-tablet D/C/F/TAF 800/150/200/10-mg complete HIV-1 regimen was shown to be bioequivalent to the combined administration of the separate agents DRV, the FTC/TAF FDC, and COBI. When administered as D/C/F/TAF, DRV exposures were lower in fasted versus fed conditions, similar to other (co-)formulations of DRV.

Example 4

Phase 3, Single-Arm, Open-Label Study to Evaluate the Efficacy and Safety of D/C/F/TAF Once Daily Fixed-Dose Combination (FDC) Regimen in Newly Diagnosed, Antiretroviral Treatment-Naïve Human Immunodeficiency Virus Type 1 (HIV-1) Infected Subjects Receiving Care in a Test and Treat Model of Care (DIAMOND)

DIAMOND is a phase 3, single-arm, open-label, prospective, multicenter study assessing the efficacy/safety of the Darunavir/Cobicistat/Emtricitabine/Tenofovir Alafenamide (D/C/F/TAF) 800/150/200/10 mg in a Test and Treat model over 48 weeks (ClinicalTrials.gov: NCT03227861). Adults diagnosed with HIV-1 infection within 14 days were immediately enrolled and started on D/C/F/TAF therapy without baseline/screening laboratory information available. Investigators reviewed baseline/screening laboratory findings as results became available; patients not meeting predefined safety or resistance stopping rules continued treatment. A planned interim analysis (descriptive statistics) was conducted when all patients had been assessed for safety/resistance stopping rules at Week 4 of enrollment.

The purpose of this study is to assess the efficacy of Darunavir/Cobicistat/Emtricitabine/Tenofovir Alafenamide (D/C/F/TAF) fixed-dose combination (FDC) in a Test and Treat model of care in newly diagnosed human immunodeficiency virus (HIV-1)-infected, treatment-naïve participants as determined by the proportion of virologic responders defined as having (HIV)-1 ribonucleic acid (RNA) lesser than 50 copies per milliliter (copies/mL) at Week 48. Another objective is to assess baseline viral resistance in the study population. Another objective is to assess HIV Treatment Satisfaction Questionnaire status version (HIVTSQs) results at Weeks 4 and 24.

Experimental Treatment Study Arm (SG): Subjects will receive oral tablet containing Darunavir 800 milligram (mg)/Cobicistat 150 mg/Emtricitabine 200 mg/Tenofovir Alafenamide 10 mg (D/C/F/TAF) fixed-dose combination (FDC) once daily within 24 hours of the screening/baseline visit.

Key Inclusion Criteria (Study Open to All Sexes, 18 Years and Older):

Newly diagnosed adults (≥18 years of age) with human immunodeficiency virus type 1 (HIV-1) evidenced by any of the following within 2 weeks of the screening/baseline visit: a) HIV Rapid Antibody positive; or b) HIV Immunoassay positive; or c) Positive p24 antigen and a HIV-1 ribonucleic acid (RNA) viral load greater than or equal to (>=) 5,000 copies per milliliter (copies/mL); or d) Non-reactive HIV-1 antibody/antigen assays and HIV-1 RNA viral load (>=) 5,000 copies/mL, HIV-1 RNA viral load must be confirmed once within 1 week of initial HIV-1 RNA viral load test Antiretroviral treatment-naïve, except for the use of TRU-VADA® for pre-exposure prophylaxis (PrEP)

Must be able to swallow whole tablets

A woman must agree not to donate eggs (ova, oocytes) for the purposes of assisted reproduction during the study and for 90 days after receiving the last dose of study drug A woman, except when postmenopausal, must have a negative wine pregnancy test at screening Key Exclusion Criteria:

Known active cryptococcal infection, active toxoplasmic encephalitis, Mycobacterium tuberculosis infection, or another acquired immunodeficiency syndrome (AIDS)-defining condition that in the judgement of the investigator would increase the risk of morbidity or mortality Known history of clinically relevant hepatic disease or hepatitis that in the investigator's judgement is not compatible with Darunavir/Cobicistat/Emtricitabine/Tenofovir Alafenamide (D/C/F/TAF FDC)

Known history of cirrhosis as diagnosed based on local practices

Known history of chronic ([>=] 3 months) renal insufficiency, defined as having an estimated glomerular filtration rate (eGFR) less than (<) 50 milliliter per minute (ml/min) according to the Modification of Diet in Renal Disease (MDRD) formula Pregnant, or breast-feeding, or planning to become pregnant while enrolled in this study or within 90 days after the last dose of study treatment Baseline/screening safety laboratory findings were evaluated on Day 3 (±1 week), with the following stopping criteria (retesting of abnormal screening/baseline safety laboratory values was allowed once):

eGFR (MDRD formula)<50 mL/min

Aspartate aminotransferase (AST) or alanine aminotransferase (ALT)≥2.5 times the upper limit of normal (ULN)

Serum lipase≥1.5 times the ULN

Positive pregnancy test for women of childbearing potential

Laboratory results that the investigator believes should result in discontinuation of study medication Active hepatitis C infection that, in the opinion of the investigator, requires immediate treatment or is expected to require treatment during the study with agents not compatible with D/C/F/TAF\ Resistance was evaluated at Week 4 (±7 days) based on predicted genotypic sensitivity (assessed using GenoSure Prime®; there was no exclusion based on the presence of specific resistance-associated mutations [RAMs]); patients who did not show full genotypic sensitivity to all D/C/F/TAF components were required to stop; an exception was resistance to lamivudine/emtricitabine associated with the M184I or M184V mutation alone Primary Outcome Measures: Food and Drug Administration (FDA) Snapshot Approach is based on the last observed viral load data within the Week 48 window: virologic response is defined as HIV-1 RNA<50 copies/mL; missing HIV-1 RNA is considered as nonresponse.

TABLE 12

Secondary Outcome Measures

| Outcome Measure | TimeFrame | Description |
|---|---|---|
| Change From Baseline in log10 HIV-1 RNA Viral Load at Weeks 2, 4, 8, 12, 24, 36, and 48 | Baseline, Weeks 2, 4, 8, 12, 24, 36, and 48 | The change from baseline in log10 HIV-1 RNA viral load at weeks 2, 4, 8, 12, 24, 36, and 48 will be assessed. |
| Percentage of Participants who have HIV-1 RNA <50 copies/mL at Week 24 | Week 24 | The percentage of participants with HIV-1 RNA <50 copies/mL at week 24 will be assessed |
| Percentage of Participants who have HIV-1 RNA <50 copies/mL at Week 48 | Week 48 | The percentage of participants with HIV-1 RNA <50 copies/mL at week 48 will be assessed |
| Change From Baseline in Cluster of Differentiation 4 (CD4+) Cell Count at Weeks 12, 24, and 48 | Baseline, Weeks 12, 24, and 48 | The immunologic change will be determined by changes in CD4+ cell count. |
| Percentage of Participants Required Discontinuation After Enrollment Based on Safety Stopping Rules | Day 10 | Participants meeting any of the below safety stopping rules will be contacted to return to the study site for possible early study treatment discontinuation (ESTD): a) Estimated glomerular filtration rate (eGFR) according to the Modification of Diet in Renal Disease (MDRD) formula <50 milliliter per minute (ML/min); b) aspartate aminotransferase (AST) or alanine aminotransferase (ALT) >=2.5* upper limit of normal (ULN); c) serum lipase >=1.5* ULN; d) positive serum human chorionic gonadotropin pregnancy test (beta-hCG); e) laboratoty results that the investigator believes should result in discontinuation of study medication and f) participants identified with active hepatitis C virus (HCV) infection that in theopinion of the investigator requires HCV treatment immediately or expected to be needed during the course of thestudy with agents not compatible with D/C/F/TAFFDC. |
| Percentage of Participants Discontinuing Therapy due to Adverse Events (AEs) | Up to 30-day follow-up visit (maximum of 52 weeks after enrollment) | AE is any untoward medical occurrence in participant who received study drug without regard to possibility of causal relationship. |
| Percentage of Participants Experiencing Grade 3 and 4 Adverse Events Assessed by Division of AIDS (DAIDS) Adverse Event (AE) Grading Table Version 2.0. | Up to 30-day follow-up visit (maximum of 52 weeks after enrollment) | AE is any untoward medical occurrence in participant who received study drug without regard to possibility of causal relationship. Events with Grade 3 or higher (3 = Severe; 4 = potentially life-threatening) are events that significantly interrupt usual daily activity, requite systemic drug therapy/other treatment and are, in any situations, considered unacceptable or intolerable events. |

TABLE 12-continued

Secondary Outcome Measures

| Outcome Measure | TimeFrame | Description |
| --- | --- | --- |
| Percentage of Participants Experiencing Grade 3 and 4 Laboratory Abnormalities Assessed by Division of AIDS (DAIDS) Adverse Event (AE) Grading Table Version 2.0. | Up to 30-day follow-up visit (maximum of 52 weeks after enrollment) | Blood samples for serum chemistry and hematology and a urine sample for urinalysis will be collected at predefined time points for clinical laboratory testing. Abnormal laboratory values with Grade 3 or higher (3 = Severe; 4 = potentially life threatening) signifies interrupt usual daily activity, require systemic drug therapy/other treatment and are, in many situations, considered unacceptable or intolerable. |
| Percentage of Participants Meeting Resistance Stopping Rules, Requiring Discontinuation of Study Drug due to Baseline Resistance Findings | Up to Day 35 | The percentage of participants meeting resistance stopping rules, requiring discontinuation of study drug due to baseline resistance findings will be reported. Resistance stopping Rule includes participants who do not show full sensitivity to all drugs in the FDC study regimen according to the susceptibility assessment in the GenoSurePrime report will be contacted to return to the study site for early study treatment discontinuation (ESTD). Exception for participants with identified resistance to lamivudine/emtricitabine (FTC), attributed to the presence of the M184/V mutation alone will be permitted to remain in the study. |
| Percentage of Participants With Baseline Protease (PR), Reverse Transcriptase (RT), and Integrase (TNT) (Primary and Secondary) Resistance-Associated Mutation (RAMs) | Baseline (Day 1) | Percentage of participants with resistance-associated mutations present at baseline will be reported and include mutations in the domain of PR, RT, INI, RAMs as determined by the GenoSure Prime assay. |
| Percentage of Participants Developing RAMs and Loss of Phenotypic Susceptibility, When Available, Upon Meeting Protocol-Defined Virologic Failure | Up to Week 48 | Participants who experience a protocol-defined virologic failure will be assessed for the development of RAMs and loss of phenotypic susceptibility. Virologic failure is defined as: a) Virologic Nonresponse: HIV-1 RNA <1 log10 reduction from baseline, and HIV-1 RNA greater than or equal to (>=) 400 copies/mL at the Week 12 visit, subsequently confirmed at an unscheduled visit conducted within 3 to 6 weeks after Week 12; b) virologic Rebound: At any visit, after achieving confirmed consecutive HIV-1 RNA <50 copies/mL, a rebound in HIV 1 RNA to >=50 copies/mL, which is subsequently confirmed at a scheduled or unscheduled visit conducted within 3 to 6 weeks of the HIV-1 RNA result; or at any visit, a >1 log10 increase in HIV-1 RNA from the nadir, which is subsequently confirmed at the following scheduled or unscheduled visit conducted within 3 to 6 weeks of the HIV-1 RNA result. |
| Percentage of Participants With Protocol-Defined Virologic Failure at Week 24 and Week 48 | Week 24 and Week 48 | Virologic failure is defined as: a) Virologic Nonresponse: HIV-1 RNA <1 log10 reduction from baseline, and HIV-1 RNA greater than or equal to (>=) 400 copies/mL at the Week 12 visit, subsequently confirmed at an unscheduled visit conducted within 3 to 6 weeks after Week 12. b) Virologic Rebound: Atany visit, after achieving |

TABLE 12-continued

| Secondary Outcome Measures | | |
|---|---|---|
| Outcome Measure | TimeFrame | Description |
| | | confirmed consecutive HIV-1 RNA <50 copies/mL, a rebound in HIV 1 RNA to >=50 copies/mL, which is subsequently confirmed at a scheduled or unscheduled visit conducted within 3 to 6 weeks of the HIV-1 RNA result; or At any visit, a >1 log10 increase in HIV-1 RNA from the nadir, which is subsequently confirmed at the following scheduled or unscheduled visit conducted within 3 to 6 weeks of the HIV-1 RNA result. |
| Percentage of Participants With Lost-to-Follow-up Throughout the 48 Weeks of Treatment | Up to Week 48 | The percentage of participants with lost-to-follow-up up to 48 weeks of treatment will be assessed. |
| Percentage of Participants Discontinuing Study Drug for any Reason Other Than Withdrawal of Consent Prior to Week 48 who Have a Documented Clinic Visit With a Healthcare Provider Within 90 Days of Discontinuing Study Drug | Up to Week 60 (Documented clinic visit within 90 Days of discontinuing study drug) | The percentage of participants discontinuing study drug for any reason other than withdrawal of consent prior to week 48 who have a documented clinic visit with a healthcare provider within 90 days of discontinuing study drug will be reported. |
| Adherence Rates by Pill Count at Weeks 4, 8, 12, 24, 36, and 48 | Weeks 4, 8, 12, 24, 36, and 48 | Adherence rates will be reported according to the percentage of participants taking >95%, 80-95% and <80% of study drug as assessed by pill count at study visits at Weeks 4, 12, 24, and 48. Participants will be requested to bring unused medication and empty packaging to the study site at each visit, and the amount of study drug dispensed will be compared with the amount returned, and taking into account the period elapsed since the previous visit to assess pill count. |
| Adherence Rates by Participants Self-report, Using a 4-Day Recall at Weeks 4, 8, 12, 24, 36, and 48 | Weeks 4, 8, 12, 24, 36, and 48 | Treatment adherence based on participant self-report using a 4-day recall (that is self report over previous 4 days of treatment) will be summarized by means of descriptive statistics and frequency tabulations at Weeks 4, 8, 12, 24, 36, and 48. |
| Mean Total Scores for the HIV Treatment Satisfaction Questionnaire-Status Version (HIVTSQs) at Weeks 4, 24, and 48 | Weeks 4, 24, and 48 | The HIV treatment satisfaction questionnaire (HIVTSQ) is a 10-item self-reported scale that measures overall satisfaction with treatment and by specific domains e.g. convenience, flexibility. The HIVTSQ items are summed up to produce a treatment satisfaction score (0 to 60) and an individual satisfaction rating for each item (0 to 6) and two subscales: general satisfaction/clinical and lifestyle/ease subscales. The higher the score, the greater the improvement in treatment satisfaction as compared to the past few weeks. A smaller score represents a decline in treatment satisfaction compared to the past few weeks. |
| Number of Hospitalizations | Up to 30-day follow-up visit (maximum of 52 weeks after enrollment) | The number of hospitalizations with HIV-1 infected participants will be assessed up to 52 weeks. |
| Duration of Hospitalizations | Up to 30-day follow-up visit (maximum of 52 weeks after enrollment) | The duration of hospitalizations for MV-1 infected participants will be assessed up to 52 weeks. |
| Number of Outpatient Visits | Up to 30-day follow-up visit (maximum of 52 weeks after enrollment) | The number of outpatient visits will be reported up to 52 week. |

TABLE 12-continued

Secondary Outcome Measures

| Outcome Measure | TimeFrame | Description |
| --- | --- | --- |
| Type of Outpatient Visits | Up to 30-day follow-up visit (maximum of 52 weeks after enrollment) | Type of outpatient visits (example; general practitioner, specialist) will be reported up to 52 weeks. |
| Number of Emergency Room Visits | Up to 30-day follow-up visit (maximum of 52 weeks after enrollment) | The number of emergency room visits will be reported up to 52 weeks. |
| Number of Medications Used Throughout the Study | Up to 30-day follow-up visit (maximum of 52 weeks after enrollment) | The number of medications (including concomitant medication) used throughout the study will be reported. |
| Type of Medications Used Throughout the Study | Up to 30-day follow-up visit (maximum of 52 weeks after enrollment) | The type of medications (including concomitant medication) used throughout the study will be reported. |
| Direct Medical Costs | Up to 30-day follow-up visit (maximum of 52 weeks after enrollment) | The direct medical costs will be calculated up to 52 weeks. |

Results:

Analyses were performed on all patients who received≥1 dose of study drug (intent-to-treat population). Observed values were used in descriptive statistics; missing values were not imputed.

Patients (N=109) were median (range) age 28.0 (19-66) years, 13% women, and 32% African American, with median (range) HIV-1 RNA 4.58 (1.3-8.2) $\log_{10}$ copies/mL, 24%≥100,000 copies/mL, median (range) CD4+ count 369.0 (7-1,082) cells/mm$^3$, and 21%<200 cells/mm$^3$. See Tables 13 and 14 below.

TABLE 13

Baseline Demographic and Clinical Characteristics

| | N = 109 |
| --- | --- |
| Demographic characteristics | |
| Age, median (range), y | 28 (19-66) |
| Women, n (%) | 14 (13) |
| Race, n (%)* | |
| White | 64 (59) |
| Black or African American | 35 (32) |
| Other | 10 (9) |
| Clinical characteristics | |
| HIV-1 RNA, n | 108 |
| Median (range), $\log_{10}$ copies/mL | 4.6 (1.3-8.2) |
| ≥100,000 copies/mL, n (%) | 25 (23) |
| CD4+ cell count, n | 108 |
| Median (range); cells/mm$^3$ | 369 (7-1,082) |
| <200 cells/mm$^3$, n (%) | 23 (21) |
| Time from diagnosis to screening/baseline, median (range), d | 5 (0-14) |
| Enrolled within 48 h of diagnosis, n % | 32 (29) |

TABLE 14

Genotype at Screening/baseline

| | n = 102 |
| --- | --- |
| Genotypic susceptibility, n (%) | |
| Darunavir | 102 (100) |
| Emtricitabine | 100 (98) |
| Tenofovir disoproxil fumarate | 102 (100) |
| All PIs | 97 (95) |
| All NRTIs | 98 (96) |
| All NNRTIs | 80 (78) |
| All INIs | 97 (95) |
| RAMs, n (%) | |
| Primary PI | 5 (5) |
| Secondary PI | 100 (98) |
| Emtricitabine | 2 (2) |
| M184M/I | 1 (1) |
| M184M/V | 1 (1) |
| NNRTI | 28 (28) |
| K103N | 11 (11) |
| Primary INI | 0 |
| Secondary INI | 5 (5) |
| T97T/A | 3 (3) |
| T97A | 2 (2) |

Figure 8:
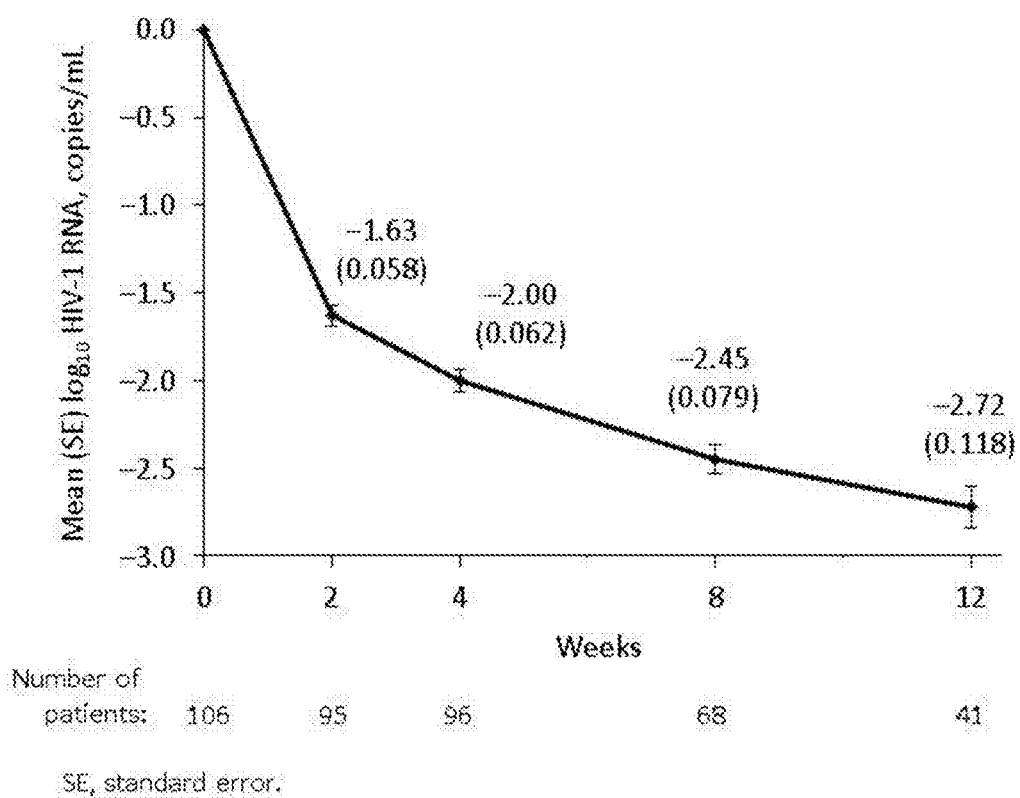
FIG. 8: Mean (SE) change from baseline in log10 HIV-1 RNA over time.

Median (range) time from diagnosis to screening/baseline was 5.0 (0-14) days; 29% of patients enrolled within 48 hours of diagnosis. Three patients met safety stopping rules and discontinued treatment; none met resistance stopping rules. Two additional patients discontinued (adverse event [AE]; protocol violation). At the interim analysis, 95.4% (104/109) of patients continued on D/C/F/TAF and only 5/109 discontinued (3 due to safety stopping rules, 1 protocol violation, 1 adverse event [AE]). At interim analysis, through Week 12, mean HIV-1 RNA decreased by 2.72 $\log_{10}$ copies/mL (FIG. 8). During treatment, incidences of grade 3 (6/109; 5.5%) and serious (3/109; 2.8%) AEs were low, with no grade 4 AEs or deaths. The most common AEs (all grades; ≥5% patients) were diarrhea (16/109; 14.7%), nausea (15/109; 13.8%), headache (8/109; 7.3%), vomiting (8/109; 7.3%), and pyrexia (6/109; 5.5%).

As of the Week 24 interim analysis, 99 (91%) patients continued on D/C/F/TAF and only 10 (9%) patients had discontinued (3 due to protocol-defined safety stopping rules, 1 protocol violation, 1 AE [rash], 2 withdrawal of consent, 3 lost to follow-up). Five patients had evidence of confirmed AST or ALT concentrations≥2.5 times the ULN at baseline/screening, meeting protocol-defined safety stopping rules. Based on Investigator assessment, 2 patients were allowed to continue treatment.

In a Test and Treat care model, >95% of HIV-1-infected patients continued D/C/F/TAF treatment at the interim analysis and did not discontinue due to predefined safety/resistance stopping rules, lack of efficacy, or safety concerns.

In the first known phase 3 trial of an STR in a Test-and-Treat model, a decline in HIV-1 RNA≥2.00 $\log_{10}$ by Week 4 and patient retention of >95% on D/C/F/TAF were achieved at interim analysis, with no discontinuations due to predefined resistance stopping rules or lack of efficacy. Organizations utilizing Test-and-Treat models should consider D/C/F/TAF as a preferred treatment option as it is the only agent with phase 3 data supporting its use in this setting.

At Week 24, 88 of 109 (81%) patients had achieved HIV-1 RNA<50 copiesltnL) and 95 of 109 (87%) patients had achieved HIV-1 RNA<200 copies/mL. Using the observed algorithm, 88 of 98 (90%) patients achieved HIV-1 RNA<50 copies/mL and 95 of 98 (97%) achieved HIV-1 RNA<200 copies/mL at Week 24. Mean HIV-1 RNA decreased from baseline to Week 24 by 3.08 $\log_{10}$ copies/mL. No patients discontinued the study due to lack of efficacy. No patients had protocol-defined VF. Patients rapidly starting and continuing D/C/F/TAF demonstrated high satisfaction scores. The most common AEs are summarized in Tables 15 and 16 below.

TABLE 15

Summary of AEs

| Parameter, n (%) | N = 109 | |
| --- | --- | --- |
| | Overall | Related |
| ≥1 AE* | 80 (73.4) | 33 (30) |
| ≥1 serious AE | 7 (6) | 0 |
| worst grade 1 AE | 40 (37) | 25 (23) |
| worst grade 2 AE | 31 (28) | 6 (6) |
| worst grade 3 AE | 9 (8) | 2 (2) |
| worst grade 4 AE | 0 | 0 |

TABLE 16

Most Common AEs (≥5% of Patients)

| Parameter, n (%) | N = 109 | |
| --- | --- | --- |
| | Overall | Related |
| Diarrhea | 23 (21) | 10 (9) |
| Nausea | 1 (16) | 13 (12) |
| Rash*, + | 15 (14) | 5 (5) |
| Vomiting | 9 (8) | 4 (4) |
| Headache | 9 (8) | 2 (2) |
| Pyrexia | 8 (7) | 1 (1) |
| Fatigue | 6 (6) | 3 (3) |

*Pooled terms of dermatitis allergic, pruritis, rash, rash macular, rash maculo-papular, and rash pruritic
+All rash AEs were grade 1 or 2, except for one that was grade 3

Most Common ADRs ((≥2% of Patients)

| Parameter, n (%) | D/C/F/TAF N = 109 | |
| --- | --- | --- |
| | Any grade | >Grade 2 |
| Diarrhea | 13 (12) | 2 (2) |
| Nausea | 10 (9) | 1 (1) |
| Rash*, | 5 (5) | 4 (4) |
| Vomiting | 4 (4) | 0 |
| Fatigue | 3 (3) | 0 |

*Pooled terms of dermatitis allergic, pruritis, rash, rash macular, rash maculo-papular, and rash pruritic Patients reported high satisfaction (HIVTSQs) scores at weeks 4 and 24 after rapid initiation of D/C/F/TAF. With a score range of 0-60, total treatment satisfaction at Week 4 (n=103) was 56.5. With a score range of 0-30, general satisfaction (clinical subscale) was 28.4 and lifestyle (ease subscale) was 28.1. With a score range of 0-60, total treatment satisfaction at Week 24 (n=98) was 57.9. With a score range of 0-30, general satisfaction (clinical subscale) was 29.0 and lifestyle (ease subscale) was 28.9.

Safety Stopping Rules

Five patients met safety stopping rule criteria; all had confirmed evidence of AST or ALT elevations≥2.5 times the ULN at the screening/baseline visit Three of these patients discontinued according to the protocol and the other 2 patients remained in the study based on clinical assessment by the investigator and agreement of the sponsor Transaminases appeared to normalize after screening/baseline in all 5 patients, indicating that treatment may have been beneficial for these patients Resistance Stopping Rules: No patients met resistance stopping rules.

In the first known phase 3 trial of an STR in a rapid initiation model of care, high proportions of patients using D/C/F/TAF achieved HIV-1 RNA<50 copies/mL and 91% (99/109) of patients continued treatment through the interim analysis at Week 24. No patients discontinued treatment due to receipt of baseline resistance reports and only 3 discontinued due to safety stopping rules. Some newly diagnosed patients may present with elevations in transaminases, which in this study appeared to normalize with initiation of ART; based on these early findings, such patients should be considered for inclusion in future rapid initiation studies. No patients had PDVF or discontinued due to lack of efficacy, and there was only 1 discontinuation due to AEs. At Weeks 4 and 24, the mean total HIVTSQs score approached the maximum score of 60, indicating high levels of patient satisfaction.

These findings, together with the demonstrated efficacy, high barrier to resistance, safety profile, and convenience of the D/C/F/TAF STR, suggest that D/C/F/TAF should be considered a preferred treatment option in a rapid initiation model of care.

Example 5

Darunavir ethanolate (D), cobicistat (C) on silicon dioxide, tenofovir alafenamide hemifumarate (TAF), emtricitabine (F), microcrystalline cellulose, and croscarmellose sodium were combined and mixed for between 5 and 20 minutes using a bin blender at about 12 rpm. (See Table, below). Magnesium stearate was added and the resulting combination was mixed using a bin blender at 12 rpm for about 2-4 minutes to form an initial blend.

The initial blend was compacted using a roller compactor (6.0-10.0 kN/cm, 1.5-3 mm roller gap). The resulting ribbons were milled using an oscillating mill and a 1.5 mm screen.

The resulting milled granules were combined with magnesium stearate and mixed using a bin blender at 12 rpm for about 2-4 minutes to form a final blend.

The final blend was compressed using a rotary tablet press. The film-coating suspension was prepared by adding the required quantity of purified water and film-coating powder to a suitable vessel. The water and film-coating powder were mixed until the powder is uniformly suspended. Tablets were loaded into a pan coater and preheated.

With the pan rotating, the required quantity of film-coating suspension is sprayed onto the tablets using an exhaust air temperature of about 44-52° C. Coated tablets were packaged into suitable packaging components. See Table 17.

TABLE 17

| D/C/F/TAF film coated tablet | % (w/w) | Amount (mg/dosage form) |
|---|---|---|
| Core Tablet | | |
| Darunavir ethanolate | 54.3 | 867 |
| Cobicistat on silicon dioxide carrier (1) | 18.1 | 288.5 |
| Emtricitabine | 12.5 | 200 |
| Tenofovir alafenamide hemifumarate | 0.7 | 11.2 |
| Microcrystalline cellulose | 7.0 | 112.2 |
| Croscarmellose sodium | 3.1 | 49.6 |
| Magnesium stearate | 1.4 | 21.7 |
| Coating | | |
| Coating powder yellow (2) | 2.9 | 46.5 |
| Purified water (3) | <16.5> | <263.5> |

(1) drug factor f = 1.9231 (from 52.0% w/w cobicistat on silicon dioxide
(2) Opadry II 85F120020 Yellow
(3) This material is a processing aid and is removed during processing

REFERENCES

Eron J, Orkin C, Gallant J, et al. Week 48 results of AMBER: a phase 3, randomised, double-blind trial in anti-retroviral treatment-naive HIV-1-infected adults to evaluate the efficacy and safety of the once-daily, single-tablet regimen of darunavr/cobicistat/emtricitabine/tenofovir alafenamide (D/C/F/TAF) versus darunavir/cobicistat plus emtricitabine/tenofovir disoproxil fumarate [oral abstract no. PS8/s]. In: 16th European AIDS Conference. 2017.

Mills A, Crofoot G, Jr., McDonald C, et al. Tenofovir alafenamide versus tenofovir disoproxil fumarate in the first protease inhibitor-based single-tablet regimen for initial HIV-1 therapy: a randomized phase 2 study. J Acquir Immune Defic Syndr. 2015; 69(4):439-45.

Orkin C, Molina J-M, Negredo E, et al. Efficacy and safety of switching from boosted protease inhibitors plus emtricitabine and tenofovir disoproxil fumarate regimens to single-tablet darunavir, cobicistat, emtricitabine, and tenofovir alafenamide at 48 weeks in adults with virologically suppressed HIV-1 (EMERALD): a phase 3, randomised, non-inferiority trial. Lancet HIV, 2017. doi: 10.1016/s2352-3018(17)30179-0.

What is claimed:

1. A method of treating a subject infected with an HIV virus comprising orally administering to the subject, once daily, a single unit dosage form comprising
   darunavir, or a hydrate or solvate thereof;
   cobicistat;
   emtricitabine; and
   tenofovir alafenamide, or a pharmaceutically acceptable salt thereof;
   wherein the subject is treatment experienced and was administered a first anti-retroviral regimen that has been discontinued; and
   wherein the subject exhibits a viral load of less than or equal to 50 copies of HIV-1 virus particles per mL of blood plasma (<50c/mL) after at least 24 weeks of the once-daily administration of the single unit dosage form.

2. The method of claim 1, wherein the single unit dosage form comprises darunavir ethanolate.

3. The method of claim 1, wherein the single unit dosage form comprises tenofovir alafenamide fumarate.

4. The method of claim 1, wherein the single unit dosage form comprises tenofovir alafenamide hemifumarate.

5. The method of claim 1, wherein the first anti-retroviral regimen comprises
   a boosted protease inhibitor;
   emtricitabine; and
   tenofovir, a tenofovir prodrug, a pharmaceutically acceptable salt of tenofovir, or a pharmaceutically acceptable salt of a tenofovir prodrug.

6. The method of claim 5, wherein the boosted protease inhibitor is
   darunavir, or a hydrate or solvate thereof, and ritonavir;
   darunavir, or a hydrate or solvate thereof, and cobicistat;
   atazanavir, or a pharmaceutically acceptable salt thereof, and ritonavir;
   atazanavir, or a pharmaceutically acceptable salt thereof, and cobicistat; or
   lopinavir and ritonavir.

7. The method of claim 1, wherein the first anti-retroviral regimen comprises tenofovir disoproxil fumarate.

8. The method of claim 1, wherein the single unit dosage form is administered with food.

9. The method of claim 1, wherein the subject is infected with HIV-1.

10. The method of claim 1, wherein the subject does not harbor any darunavir resistance-associated mutations in HIV-1 protease or a K65R mutation in HIV-1 reverse transcriptase.

11. The method of claim 1, wherein the subject harbors darunavir resistance-associated mutations in HIV-1 protease or a K65R mutation in HIV-1 reverse transcriptase.

12. The method of claim 1, wherein the subject's has hepatic impairment and the hepatic impairment is Child-Pugh Class A or Child Pugh Class B.

13. The method of claim 1, wherein the subject does not exhibit detectable amounts of hepatitis B virus prior to the administration of the single unit dosage form.

14. The method of claim 1, wherein the subject exhibits detectable amounts of hepatitis B virus prior to the administration of the single unit dosage form.

15. The method of claim 1, wherein the subject exhibits a viral load of less than or equal to 50 copies of HIV-1 virus particles per mL of blood plasma (<50c/mL) prior to the administration of the single unit dosage form.

16. The method of claim 1, wherein the single unit dosage form comprises about 800 mg of darunavir.

17. The method of claim 1, wherein the single unit dosage form comprises about 150 mg of cobicistat.

18. The method of claim 1, wherein the, single unit dosage form comprises about 200 mg of emtricitabine.

19. The method of claim 1, wherein the single unit dosage form comprises about 10 mg of tenofovir alafenamide.

20. The method of claim 1, wherein the single unit dosage form comprises about 11.2 mg of tenofovir alafenamide fumarate.

21. The method of claim 1, wherein the subject exhibits a viral load of less than or equal to 50 copies of HIV-1 virus particles per mL of blood plasma (<50c/mL) after at least 48 weeks of once daily administration of the second anti-retroviral regimen.

22. The method of claim 1, wherein the subject exhibits a viral load of less than or equal to 50 copies of HIV-1 virus particles per mL of blood plasma (<50c/mL) after at least 96 weeks of once daily administration of the single unit dosage form.

23. The method of claim 1, wherein the subject exhibits the same or an improved cluster of differentiation (CD) 4+ cell count after at least 24 weeks, at least 48 weeks, or at least 96 weeks, of once daily administration of the single unit dosage form, as compared to the subject's CD4+ count prior to the administration.

24. The method of claim 1, wherein the subject does not exhibit an emergent resistance-associated mutation in an HIV virus after at least 24 weeks, at least 48 weeks, or at least 96 weeks, of once daily administration of the single unit dosage form.

25. The method of claim 5, wherein the pharmaceutically acceptable salt of a tenofovir prodrug is tenofovir disoproxil or tenofovir disoproxil fumarate.

* * * * *